US012667418B1

(12) United States Patent
Zaidenberg et al.

(10) Patent No.: US 12,667,418 B1
(45) Date of Patent: Jun. 30, 2026

(54) SYSTEMS AND METHODS FOR PERFORMING ABLATION WITH A LEFT ATRIAL APPENDAGE IMPLANT DEVICE

(71) Applicant: BIOSENSE WEBSTER (ISRAEL) LTD., Yokneam (IL)

(72) Inventors: Tomer Zaidenberg, Herzlyia (IL); Eli Vaknin, Kiryat Bialik (IL); Adam Sapir, Malot (IL); Keren Bitton Worms, Haifa (IL); Alexander Vaynshtein, Yokneam (IL); Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

(21) Appl. No.: 19/214,299

(22) Filed: May 21, 2025

(51) Int. Cl.
    *A61B 18/14*     (2006.01)
    *A61B 17/12*     (2006.01)
    *A61B 18/00*     (2006.01)
    *A61B 18/16*     (2006.01)

(52) U.S. Cl.
    CPC .... *A61B 18/1492* (2013.01); *A61B 17/12122* (2013.01); *A61B 17/12172* (2013.01); *A61B 2017/1205* (2013.01); *A61B 2018/00267* (2013.01); *A61B 2018/00351* (2013.01); *A61B 2018/00375* (2013.01);
    (Continued)

(58) Field of Classification Search
    CPC .......... A61B 18/1492; A61B 17/12122; A61B 17/12172; A61B 2017/1205; A61B 2018/00267; A61B 2018/00351; A61B 2018/00577; A61B 2018/00613; A61B 2018/1405; A61B 2018/165
    See application file for complete search history.

(56) References Cited

U.S. PATENT DOCUMENTS

| 5,443,489 | A | 8/1995 | Ben-Haim |
| 5,558,091 | A | 9/1996 | Acker |
| 6,172,499 | B1 | 1/2001 | Ashe |
| (Continued) | | | |

FOREIGN PATENT DOCUMENTS

| CN | 212165884 U | 12/2020 |
| CN | 214017798 U | 8/2021 |
| (Continued) | | |

*Primary Examiner* — Linda C Dvorak
*Assistant Examiner* — Abigail Bock
(74) *Attorney, Agent, or Firm* — Clayton, McKay & Bailey, PC

(57) ABSTRACT

Described herein are examples of a left atrial appendage ("LAA") occlusion or elimination implant device further configured to ablate tissue located at an atrium of the heart or nearby veins and ostia. The implant device can be delivered to a patient's heart using a catheter system and includes a contact member comprising one or more electrodes. In use, the electrodes of the contact member can perform unipolar or bipolar ablation at an ablation site that is distinct from an ostium or interior of the LAA. The implant device can then be re-positioned at least partially within the LAA, and the contact member can be implanted to occlude or eliminate the LAA. The implant device can further include a securing element comprising one or more electrodes, the securing element configured to cooperate with the contact member in performing unipolar or bipolar ablation and/or occluding or eliminating the LAA.

20 Claims, 43 Drawing Sheets

(52) U.S. Cl.
CPC ............... *A61B 2018/00577* (2013.01); *A61B 2018/00613* (2013.01); *A61B 2018/1405* (2013.01); *A61B 2018/165* (2013.01)

(56) References Cited

U.S. PATENT DOCUMENTS

| | | | |
|---|---|---|---|
| 6,239,724 | B1 | 5/2001 | Doron |
| 6,332,089 | B1 | 12/2001 | Acker |
| 6,484,118 | B1 | 11/2002 | Govari |
| 6,618,612 | B1 | 9/2003 | Acker |
| 6,690,963 | B2 | 2/2004 | Ben-Haim |
| 6,788,967 | B2 | 9/2004 | Ben-Haim |
| 6,892,091 | B1 | 5/2005 | Ben-Haim |
| 7,536,218 | B2 | 5/2009 | Govari |
| 7,756,576 | B2 | 7/2010 | Levin |
| 7,848,787 | B2 | 12/2010 | Osadchy |
| 7,869,865 | B2 | 1/2011 | Govari |
| 8,456,182 | B2 | 6/2013 | Bar-tal |
| 11,712,247 | B2 | 8/2023 | O'Halloran |
| 2017/0100187 | A1* | 4/2017 | Basu .................. A61B 18/1492 |
| 2017/0281193 | A1 | 10/2017 | Asirvatham |
| 2020/0008870 | A1* | 1/2020 | Gruba .................. A61B 18/082 |
| 2021/0161592 | A1 | 6/2021 | Altmann |
| 2021/0162210 | A1 | 6/2021 | Altmann |
| 2021/0169550 | A1 | 6/2021 | Govari |
| 2021/0169567 | A1 | 6/2021 | Govari |
| 2021/0169568 | A1 | 6/2021 | Govari |
| 2021/0177503 | A1 | 6/2021 | Altmann |
| 2021/0186604 | A1 | 6/2021 | Altmann |
| 2021/0196372 | A1* | 7/2021 | Altmann ............ A61B 18/1492 |
| 2022/0079667 | A1 | 3/2022 | Gabay |
| 2022/0087741 | A1* | 3/2022 | Lashinski .......... A61B 18/1492 |

FOREIGN PATENT DOCUMENTS

| | | |
|---|---|---|
| CN | 215839285 U | 2/2022 |
| WO | WO2022171148 | 8/2022 |

* cited by examiner

510
Fully or partially deploy the implant device from the catheter

520
Position one or more electrodes in contact with tissue

530
Deliver ablative energy

540
Circumferential legion complete ?

No

550
Reposition electrodes of the implant device

Yes

560
Transition implant device for LAA closure or elimination

710 — Advance inplant device to LAA ostium

720 — Place contact member in contact with LAA wall or ostium

730 — Rotate contact member to constrict LAA ostium

740 — Advance security element into contact with tissue opposite the contact member 750 — perform optional ablation

8002

8002

8002

8002

SYSTEMS AND METHODS FOR PERFORMING ABLATION WITH A LEFT ATRIAL APPENDAGE IMPLANT DEVICE

FIELD OF THE DISCLOSURE

The present disclosure relates to devices, apparatuses, and methods for ablating cardiac tissue using an implant device adapted for closing or occluding a left atrial appendage.

BACKGROUND

Left atrial appendage (LAA) occlusion or closure has been typically performed in high-risk patients due to possible stroke risk. For example, LAA closure or elimination techniques are generally performed to block emboli from exiting the LAA. Typical surgical closure includes stitching the opening closed via left atrium entry. Other techniques include the application of external clamps such as ATRI-CLIP manufactured by Atricure where a Nitinol device is used to clamp the appendage without opening the left atrium to exclude the appendage from left atrium blood circulation.

As an alternative to closure or elimination techniques, LAA occlusion techniques have typically used a plug to close the appendage from the inside of the left atrium. Such plugs can be constructed, for example, from a laser cut Nitinol tube expanded to a semi-spherical shape. The portion exposed to the left atrium can be covered with a cover-such as a thin micron membrane made from polyethylene tere-phthalate. The membrane can act as a blood barrier to prevent flow from flowing through and between one or more struts of the plug. Typical sizes range between approximately 20 mm and 35 mm in diameter and approximately 20 mm and 40 mm in depth. The device can have anchors protruding from an outer surface of the device intended to engage the wall of the appendage and prevent movement post deployment. The device can be delivered via venous access through the groin and a transseptal crossing into the left atrium where a guide catheter and coaxial delivery catheter are positioned proximal to the left atrial appendage. The implant for appendage exclusion is typically positioned at the distal most portion of the delivery catheter. The device is typically positioned and deployed using fluoroscopy and echocardiography for guidance.

Conventional occlusion devices can include complicated pre-procedural sizing algorithms used to determine the appropriate device size, migration of the implant, leakage around or through the implant, and/or fracture of the implant, all which may exacerbate the thrombus and stroke problem the device was designed to reduce. A typical drug regimen associated with conventional LAA treatment devices includes warfarin anticoagulation for 45 days (approximately 6 weeks) followed by dual antiplatelet therapy (DAPT) for six months post-procedure and aspirin thereafter. Another procedure typically required with conventional LAA treatment devices includes a follow up transesophageal echogram at six weeks following the procedure. The incidence of device-related thrombus in patients with LAA imaging has been reported to be 7.2% per year.

Known devices and techniques for LAA occlusion or elimination lack additional functionality for reducing the complexity, instrumentation, and time required to perform other procedures that may be performed in conjunction with a LAA procedure. For example, patients requiring LAA occlusion or closure may also require treatment for cardiac arrhythmias. Cardiac arrhythmias, such as atrial fibrillation (AF), occur when regions of cardiac tissue abnormally conduct electric signals to adjacent tissue. This disrupts the normal cardiac cycle and causes asynchronous rhythm. Treatment of arrhythmias can include surgically disrupting the origin of the signals causing the arrhythmia and disrupting the conducting pathway for such signals. By selectively ablating cardiac tissue by application of energy via a catheter and one or more electrodes, it is possible to cease or modify the propagation of unwanted electrical signals from one portion of the heart to another.

What is needed, therefore, are devices and methods for simplifying cardiac procedures by reducing the time and instrumentation needed to perform cardiac surgical procedures, including ablation and LAA occlusion or elimination.

SUMMARY OF SOME EXEMPLIFYING ARRANGEMENTS

The systems, methods and devices of this disclosure each have several innovative aspects and implementations, no single one of which is solely responsible for the desirable attributes disclosed herein.

Disclosed herein are arrangements of a system for performing ablation and treating a left atrial appendage with an implant device. In some arrangements, a catheter can be configured to deploy the implant device, the implant device including a contact member comprising one or more electrodes. The electrodes can be configured or arranged for ablating tissue at a location distinct from the ostium and interior of the LAA, such as within an atrium of the heart, including but not limited to the roof, floor, or pulmonary veins thereof, or in the ventricle. In another aspect, the contact member can be further adapted to treat the LAA. For example, after performing an ablation at an ablation site, the contact member can be re-positioned at least partially within the LAA to occlude or eliminate the LAA. In some embodiments, the implant can further include a securing element configured for placement at least partially outside the LAA. In one aspect, the securing element can cooperate with the contact member to occlude or close the LAA.

In additional arrangements, the one or more electrodes of the contact member can be coupled to portions of the contact member, such as struts of the contact member. In alternative arrangements, the contact member can be energized such that the contact member itself can serve as an electrode. In further examples, the electrodes of the securing element can be coupled to a body portion of the securing element, such as arms or struts belonging to the securing element. Alternatively, like the contact member, the securing element can be energized such that the securing element itself can serve as an electrode. Any of the electrodes of the contact member or securing element, including the contact member or securing element themselves, can be used to perform unipolar ablation. In other embodiments, any pair of electrodes, again including the contact member and securing element themselves, can be used to perform bipolar ablation.

Also disclosed herein are arrangements of a method for performing cardiac ablation and treating a LAA that can include advancing an implant device comprising one or more electrodes to an ablation site located outside the LAA, ablating tissue at the ablation site using the one or more electrodes, and re-positioning the implant device at an implant site located at least partially within the LAA and/or the LAA ostium.

In additional arrangements, the ablation site can be selected from any one or more of a pulmonary vein ostia, a left atrial posterior wall, a left atrial roof, a mitral isthmus, a coronary sinus, and a right atrium or in the ventricle, such as but not limited to the inferior wall, anterior wall, lateral wall, epicardial surface, right ventricular outflow tract, left ventricular outflow tract, papillary muscles, septum, or substrate-based targets (e.g., scars). In some embodiments, the implant device can include a contact member comprising the one or more electrodes. Prior to ablating tissue at the ablation site, in some examples, the contact member can be deployed from a collapsed state restrained within a catheter delivery system to an expanded state when outside, and unrestrained by, the catheter. In further embodiments, the implant device can also include a securing element configured for placement at the implant site and at least partially outside the LAA, the securing element adapted for cooperation with the contact member to occlude or close the LAA. In some examples, like the contact member, the securing element is configured for deployment from a collapsed state restrained within the catheter delivery system to an expanded state when outside, and unrestrained by, the catheter. In another aspect, the securing element can comprise one or more electrodes. In such examples, the electrodes of the contact member and the electrodes of the securing element (or the contact member and securing element themselves) can be used to perform unipolar or bipolar ablation.

Also disclosed herein are arrangements of a system for occluding or closing a LAA. In some arrangements, the system can include an implant device configured for placement at least partially within the LAA, and a catheter configured to deploy the implant device. In some arrangements, the catheter can include an outer sheath coupled with a first connector, a first dial coupled with the outer sheath, an inner catheter member configured to rotate the implant when a distal end portion of the inner catheter member is engaged with the implant, and a second dial coupled with the inner catheter member. In one aspect, the first dial is configured to axially move the first connector and the outer sheath in a first axial direction from an initial axial position to a second axial position when the first dial is rotated in a first direction, and the second dial is configured to rotate the inner catheter member and the implant in a first rotational direction from an initial position to a second rotational position when the second dial is rotated in a first direction.

Any arrangements of the devices, systems, and methods disclosed herein can include, in additional arrangements, one or more of the following features, components, and/or details, in any combination with any of the other features, components, and/or details of any other arrangements disclosed herein: wherein the system is configured to cause a rotating portion of the implant to move from a first state to a second, expanded state and to move an outside surface of the rotating portion of the implant against an inner wall surface of the left atrial appendage; further including a second inner catheter member and a third dial coupled with the second inner catheter member, wherein the third dial is configured to rotate the second inner catheter member and to move a locking portion of the implant toward a rotating portion of the implant when the third dial is rotated in a first direction; wherein the locking portion comprises one or more arms extending away from a body portion of the implant and configured to penetrate into the tissue of the left atrial appendage that has constricted and gathered inwardly around an outside surface of a portion of the implant; wherein the locking portion comprises one or more arms extending away from a body portion of the locking portion, the locking portion being configured to move at least from a first state in which the one or more arms are collapsed and a second state in which the one or more arms are expanded such that an end portion of each of the one or more arms are spaced further apart from the body portion of the implant when the locking portion is in the second state than when the locking portion is in the first state; wherein the one or more arms of the locking portion are configured to extend toward the rotating portion of the implant when the locking portion is in the second state; further comprising a stop element configured to limit a range of movement of the first connector relative to the first dial so as to limit a range of movement of the outer sheath relative to the implant, wherein the stop element is removable and repositionable to adjust range of movement; further including a third inner catheter member and a fourth dial coupled with the third inner catheter member, wherein the fourth dial is configured to rotate the third inner catheter member and unthread the third inner catheter member from the implant to release the implant from the catheter at least when the fourth dial is rotated in a first direction; further including a second inner catheter member and a third dial coupled with the second inner catheter member, wherein the third dial is configured to rotate the second inner catheter member and to move a locking portion of the implant toward a rotating portion of the implant when the third dial is rotated in a first direction; further including a third inner catheter member and a fourth dial coupled with the third inner catheter member, wherein the fourth dial is configured to rotate the third inner catheter member and unthread the third inner catheter member from the implant to release the implant from the catheter at least when the fourth dial is rotated in a first direction, and a linking element comprising a sleeve configured to selectively key the third dial with the fourth dial so that fourth dial cannot be independently rotated relative to the third dial when the linking element is engaged with the fourth dial and the third dial; and/or further including a removable locking element configured to selectively prevent the linking element from becoming disengaged from the third dial and the fourth dial, wherein the locking element comprises a suture.

Additionally, any arrangements of the devices, systems, and methods disclosed herein can include, in additional arrangements, one or more of the following features, components, and/or details, in any combination with any of the other features, components, and/or details of any other arrangements disclosed herein: wherein the other sheath comprises an inner layer and an outer layer positioned over the inner layer along at least a portion of a length of the inner layer such that a distal end portion of the inner layer having a plurality of openings therein is not covered by the outer layer; wherein the plurality of openings comprise a plurality of angled slits formed in the inner layer of the outer sheath, wherein the plurality of angled slits are configured to increase a flexibility of the outer sheath and to permit a passage of a contrast media through the angled slits; further including a support stand for supporting the catheter and at least a guide catheter, wherein the support stand is configured to be positioned on a support surface, such as a bed or table, or on a patient's body; and/or wherein the support stand for supporting the catheter comprises a slot therein that is configured to receive a projection of the catheter, and wherein the catheter has a locking element configured to selectively secure the catheter in a desired position along the slot when the locking element is engaged.

Also disclosed herein are arrangements of a method of treating a left atrial appendage, that can include advancing an implant into the left atrial appendage, engaging an inner wall surface of the left atrial appendage with a portion of the implant, rotating the implant in a first direction from an initial position by a first predetermined angle, moving the implant in a proximal direction by a first predetermined distance, and rotating the implant in the first direction by a second predetermined angle.

Additionally, any arrangements of the devices, systems, and methods disclosed herein can include, in additional arrangements, one or more of the following features, components, and/or details, in any combination with any of the other features, components, and/or details of any other arrangements disclosed herein: further including moving the implant in the proximal direction by the first predetermined distance after rotating the implant in the first direction by the first predetermined angle and rotating the implant in the first direction by the second predetermined angle after moving the implant in the proximal direction by the first predetermined distance; further including moving the implant in the proximal direction by the first predetermined distance while simultaneously rotating the implant in the first direction by the first predetermined angle; further including preventing the implant from rotating back to the initial position; further including deploying a securing element to prevent the implant from rotating back to the initial position after rotating the implant in the first direction by the second predetermined angle; wherein rotating the implant in the first direction by the second predetermined angle comprises rotating the implant to a final rotational position, the method further comprising deploying a securing element to prevent the implant from rotating back to the initial position after rotating the implant to the final rotational position; wherein the first predetermined angle is greater than or equal to 90 degrees; wherein the first predetermined angle is greater than or equal to 180 degrees; wherein the first predetermined angle is from 200 degrees to 330 degrees; wherein the first predetermined distance is greater than or equal to 0.5 cm; wherein the first predetermined distance is from 0.25 cm to 1.75 cm; wherein the second predetermined angle is greater than or equal to 15 degrees; wherein the second predetermined angle is greater than or equal to 30 degrees; wherein the second predetermined angle is from 30 degrees to 90 degrees; further including enlarging the implant from a first state to a second state before rotating the implant in the first direction by the first predetermined angle, wherein at least a portion of the implant is enlarged in a radial direction when the implant is in the second state as compared to the first state; and/or further including preventing the implant from rotating back to the first rotational position.

Disclosed herein are arrangements of methods of treating a left atrial appendage. In some arrangements, the method can include twisting the left atrial appendage and/or securing the left atrial appendage in a twisted position. Any arrangements of the methods, devices and systems of treating a left atrial appendage disclosed herein can include, in additional arrangements, one or more of the following steps, features, components, and/or details, in any combination with any of the other steps, features, components, and/or details of any other arrangements disclosed herein: wherein twisting the left atrial appendage can include engaging a wall portion on an inside of the left atrial appendage with a contact member and rotating the contact member from a first rotational position (also referred to herein as a first position) to a second rotational position (also referred to herein as a second position) to twist the left atrial appendage; wherein engaging a wall portion on an inside of the left atrial appendage with a contact member can include advancing a deployment device into the left atrial appendage; wherein engaging a wall portion on an inside of the left atrial appendage can include engaging a wall portion on an inside of the left atrial appendage with one or more tissue anchors;

wherein the contact member can be a balloon; wherein the contact member can be positioned on an implant coupled with the deployment device; wherein the implant can be self-expanding, balloon expandable and/or mechanically expandable; further including applying a vacuum through the contact member to engage the left atrial appendage; wherein rotating a component of the deployment device rotates the contact member from the first rotational position to the second rotational position to twist the left atrial appendage; wherein rotating the contact member from the first rotational position to the second rotational position to twist the left atrial appendage can include rotating the contact member at least approximately 90° in either direction from the first rotational position; wherein rotating the contact member from the first rotational position to the second rotational position to twist the left atrial appendage can include rotating the contact member at least approximately 180° in either direction from the first rotational position; wherein rotating the contact member from the first rotational position to the second rotational position to twist the left atrial appendage can include rotating the contact member from approximately 90° to approximately 360° in either direction from the first rotational position; wherein rotating the deployment device can include exerting a torque on the deployment device between 0.25 in-oz of torque and 10 in-oz of torque; wherein the method further includes allowing the contact member to rotate from the second direction to a third rotational position that can be between the first rotational position and the second rotational position (for example and without limitation, as a result of the tissue relaxing); and/or wherein the contact member includes at least one vacuum port configured to communicate a suction force through the at least one vacuum port from a source of suction.

Further, any arrangements of the methods, devices and systems of treating a left atrial appendage disclosed herein can include, in additional arrangements, one or more of the following steps, features, components, and/or details, in any combination with any of the other steps, features, components, and/or details of any other arrangements disclosed herein: wherein twisting the left atrial appendage can include rotating a portion of the left atrial appendage about an axis from a first rotational position to a second rotational position to twist the left atrial appendage; wherein rotating a portion of the left atrial appendage about an axis from a first rotational position to a second rotational position to twist the left atrial appendage can include rotating the portion of the left atrial appendage at least approximately 90° in either direction from the first rotational position; wherein rotating a portion of the left atrial appendage about an axis from a first rotational position to a second rotational position to twist the left atrial appendage can include rotating the portion of the left atrial appendage at least approximately 180° in either direction from the first rotational position; wherein rotating a portion of the left atrial appendage about an axis from the first rotational position to the second rotational position to twist the left atrial appendage can include rotating the portion of the left atrial appendage from approximately 90° to approximately 360° in either direction from the first rotational position; wherein rotating a portion of the left atrial appendage about an axis from a first rotational position to a second rotational position to twist the left atrial appendage can include twisting the left atrial appendage until an ostium of the LAA can be substantially or completely closed; wherein securing the left atrial appendage in a twisted position can include engaging tissue of the heart that has been twisted; wherein engaging tissue of the heart that has been twisted can include engaging tissue wall with an anchor element; wherein the anchor element can include a suture; wherein securing the left atrial appendage in a twisted position can include securing a tissue of the heart outside of an occluded portion of the left atrial appendage with an anchor element; and/or wherein the anchor element can include a plurality of tissue anchors on at least one surface thereof configured to engage with the internal wall of the heart outside of the left atrial appendage.

Also disclosed herein are arrangements of a method of closing the ostium of a left atrial appendage. In some arrangements, the method can include twisting tissue of the heart to constrict the ostium of the left atrial appendage and/or securing tissue that has gathered as a result of twisting tissue of the heart in a gathered position. Any arrangements of the methods, devices and systems of closing the ostium of a left atrial appendage disclosed herein can include, in additional arrangements, one or more of the following steps, features, components, and/or details, in any combination with any of the other steps, features, components, and/or details of any other arrangements disclosed herein: wherein securing the tissue of the heart in the gathered position can include advancing a securing element into the gathered tissue; wherein the securing element can be a suture; and/or wherein the securing element can be a tissue anchor.

Disclosed herein are arrangements of devices and systems for treating an LAA that can include an implant comprising a contact member, and a securing element, wherein the contact member is configured to rotate at least in a first direction from a first rotational position to a second rotational position, wherein the contact member is configured to twist at least a portion of the LAA when the contact member is rotated from the first rotational position to the second rotational position, and wherein the securing element is configured to prevent a rotation of the implant in a second direction that is opposite to the first direction when the securing element is in an operable state. The contact member can be, in some arrangements, configured to move between a first state and a second state, wherein the contact member is larger or is expanded in the second state. Some arrangements of the contact member can be configured to move from the first state to the second state so that at least a portion of the contact member engages a wall portion of the LAA when the contact member is advanced into the LAA. In any arrangements disclosed herein wherein the contact member moves or expands from a first state to a second state, the contact member can be moved or expanded from the first state to the second state in the LA or in the LAA. Further, in any arrangements, the contact member can be configured to remain in a fixed state and/or size during the entire procedure, wherein the contact member can be extended past a distal end of the delivery catheter (or an outside tube of the delivery catheter can be withdrawn) and advanced into contact or engagement with a wall portion of the LAA, and then twisted. This can be done without changing a size of the contact member and/or without expanding the contact member.

Also disclosed herein are arrangements of devices and systems for treating an LAA can include an implant configured to move between a first state and a second state, a catheter configured to advance the implant into the LAA when the implant is in the first state and to cause the implant to move from the first state to the second state so that an outside surface of the implant moves against an inner wall surface of the LAA after the implant has been advanced into the LAA, wherein the catheter is configured to rotate the implant in a first direction from a first rotational position to a second rotational position so that the implant can twist at least a portion of the LAA when the implant is in the second state.

Also disclosed herein are arrangements of devices and systems for drawing a first tissue surface toward a second tissue surface, including a contact member configured to expand from a first state to a second state and a securing element configured to move from a first state to a second state, wherein the contact member can be configured to expand from the first state to the second state so that at least a portion of the contact member engages at least a distal portion of the first tissue surface and at least a distal portion of the second tissue surface, the contact member can be configured to rotate at least in a first direction from a first rotational position to a second rotational position, wherein the rotation of the contact member in the first direction causes at least a proximal portion of the first tissue surface to twist and to move toward a proximal portion of the second tissue surface, and wherein the securing element is configured to prevent a rotation of the implant in a second direction when the securing element is in an operable state and engaged with a tissue portion adjacent to and/or comprising the proximal portions of the first and second tissue surfaces, wherein the second direction is opposite to the first direction. Further, in any device and/or system arrangements disclosed herein, the device can be configured to occlude or close a cavity in a body having the first and second tissue surfaces, the first and second tissue surfaces can be tissue surfaces within any cavity within the body, and/or wherein the rotation of the contact member further causes the proximal portion of the second tissue surface to twist and to move toward the proximal portion of the first tissue surface.

Any arrangements of the devices and systems disclosed herein can include, in additional arrangements, one or more of the following features, components, and/or details, in any combination with any of the other features, components, and/or details of any other arrangements disclosed herein: wherein the implant is self-expandable such that the implant automatically expands from the first state to the second state when a restraint is removed from the implant; wherein the contact member is self-expandable such that at least a portion of the contact member automatically expands from the first state to the second state when a restraint is removed from the contact member; wherein the implant is substantially collapsed when the implant is in the first state and is expanded when the implant is in the second state such that a size of the implant is bigger when the implant is in the second state than when the implant is in the first state; wherein the contact member is biased to remain in the second state after deployment into the LAA; wherein the contact member is configured to be rotated in a clockwise or a counter-clockwise direction; wherein the device is configured to cause a tissue of the left atrium and/or the LAA to constrict around an outer surface of a body portion of the implant when the contact member is rotated to the second rotational position, and the securing element is configured to engage with the tissue that has constricted around the outer surface of the body portion of the implant to prevent rotation of the implant in the second direction; wherein the securing element has a plurality of tissue anchors configured to engage with an internal wall of the heart adjacent to the LAA; wherein the securing element has a helical shape and is configured to rotate about a body portion of the implant during the implantation procedures; wherein the implant is configured to rotate in a first direction from the first rotational position to the second rotational position; wherein the implant is configured to prevent rotation of the implant in a second direction after the implant has been fully deployed, wherein the second direction is opposite to the first direction; wherein the contact member has a plurality of tissue anchors on an outside surface thereof; wherein the plurality of tissue anchors on the outside surface of the contact member are configured to engage an inner wall surface of the LAA after the contact member has been moved to the second state; wherein the implant comprises a securing element configured to engage with a tissue portion of the heart adjacent to the LAA; wherein the second rotational position is at least one-quarter of a complete rotation relative to the first rotational position; wherein the second rotational position is at least one-half of a complete rotation relative to the first rotational position; and/or wherein the second rotational position is from approximately one-quarter of a complete rotation to one or more complete rotations relative to the first rotational position.

Further, any arrangements of the devices and systems disclosed herein can include, in additional arrangements, one or more of the following features, components, and/or details, in any combination with any of the other features, components, and/or details of any other arrangements disclosed herein: further comprising a catheter selectively coupled with the contact member and configured to exert a torque on the contact member to rotate the contact member from the first rotational position until a threshold predetermined torque level is reached; wherein a threshold predetermined torque level is from approximately 0.25 in-oz of torque to approximately 10 in-oz of torque; wherein a threshold predetermined torque level is from approximately 0.5 in-oz of torque to approximately 5 in-oz of torque; further comprising a retention element configured to bias the securing element toward a tissue wall of the LAA; further comprising a retention element configured to bias the securing element toward the contact member; further comprising a retention element configured to couple the securing element with the contact member; wherein the retention element comprises a threaded shaft; wherein the device is configured such that a rotation of the retention element in a first direction causes the securing element to move toward the contact member; wherein the contact member is configured to rotate at least in a first direction from a first rotational position to a second rotational position when a torque is applied to the contact member; wherein the device is configured such that the contact member can be removed from the LAA after the securing element has been deployed to the operable state of the securing element; wherein the device is configured such that the contact member can be removed from the LAA after the securing element has been deployed to the operable state of the securing element, and wherein the securing element is configured to prevent a rotation of the tissue of the left atrium and/or the LAA that has been constricted as a result of the rotation of the contact member from the first rotational position to the second rotational position; wherein only a portion of the securing element extends into the left atrium after deployment of the device, and all other portions of the device are internal to the LAA after deployment of the device; wherein only approximately 10% or less of an overall length of the deployed device extends into the left atrium after deployment of the device; wherein a proximal portion of the contact member is configured to bias any folds or overlapped tissue of the left atrial appendage that have formed around the contact member as a result of the rotation of the contact member in the left atrial appendage to slide off or move proximally away from the contact member, so that only a minimal amount of folds or overlapped tissue, if any, will be formed around the outside of the contact member; wherein the securing element is rotationally fixed to the contact member such that a rotation of the contact member will cause an equal and simultaneous rotation of the securing element; wherein the device is configured for use by a surgical robot device or system; a surgical robotic device, comprising one or more robotic arms and wherein the device of any arrangements disclosed herein is configured for use by the surgical robotic device; wherein the contact member and the securing element are integrally formed and/or monolithically formed; wherein the device is configured to cause a tissue of the left atrium and/or the LAA to constrict around an outer surface of a body portion of the implant when the contact member is rotated to the second rotational position, and the securing element is configured to compress the tissue that has constricted around the outer surface of the body portion of the implant between a distal surface of the securing element and the contact member to prevent rotation of the implant in the second direction.

Some arrangements of devices and systems for closing or occluding a left atrial appendage (LAA) disclosed herein can include an implant configured to move between a first state and a second state and a catheter configured to advance the implant into the left atrial appendage when the implant is in the first state, wherein the implant can be configured to move from the first state to the second state so that at least a portion of the implant engages a wall portion of the left atrial appendage after the implant has been advanced into the left atrial appendage, and wherein the implant can be configured to twist at least a portion of the left atrial appendage when the implant is rotated from a first rotational position to a second rotational position when the implant is in the second state. In any arrangements disclosed herein, the twisting movement or step can be accomplished by a torque catheter.

Any arrangements of the devices and systems disclosed herein can, in additional arrangements, include one or more of the following features or details, in any combination: wherein the implant is configured to automatically rotate from the first rotational position to the second rotational position after the implant is in the second state; wherein the implant can be configured to be triggered or activated to thereafter automatically rotate from the first rotational position to the second rotational position; wherein the device has a spring that is coupled with the implant, the spring being configured to automatically rotate the implant when the spring is released or activated; wherein the implant can be self-expandable such that the implant automatically expands from the first state to the second state when a restraint is removed from the implant; wherein the implant can be self-expandable such that at least a portion of the implant automatically expands from the first state to the second state when the implant is advanced past a distal end of an outer sleeve of the catheter; wherein the implant is substantially collapsed when the implant is in the first state and can be expanded when the implant is in the second state such that a size of the implant can be bigger when the implant is in the second state than when the implant is in the first state; wherein the implant can be biased to remain in the second state after deployment into the left atrial appendage; wherein the implant can be configured to be rotated in a clockwise or a counter-clockwise direction; wherein the implant can include a securing element configured to engage with an internal wall of the heart outside of the left atrial appendage; wherein the implant can include a securing element configured to engage with an internal wall of the heart outside of the left atrial appendage, wherein the securing element has a helical shape and is configured to rotate about a body portion of the implant during the implantation procedures; wherein the implant can include a corkscrew shaped securing element configured to engage with an internal wall of the heart outside of the left atrial appendage; wherein the implant can include a securing element having a corkscrew tissue anchor to engage the internal wall of the heart and/or LAA tissue; wherein the implant can include a securing element having a plurality of tissue anchors configured to engage with an internal wall of the heart adjacent to the left atrial appendage; wherein the implant can be configured to prevent the implant from rotating back to the first rotational position after the implant has been fully deployed; wherein the implant can be configured to rotate in a first direction from the first rotational position to the second rotational position, and the implant can be configured to prevent rotation of the implant in a second direction after the implant has been fully deployed, the second direction being opposite to the first direction.

Any arrangements of the devices and systems disclosed herein can, in additional arrangements, include one or more of the following features or details, in any combination: wherein the implant has a plurality of tissue anchors on an outside surface thereof; wherein the plurality of tissue anchors on the outside surface of the implant configured to engage an inner wall surface of the left atrial appendage after the implant has been moved to the second state; wherein the implant can include a securing element configured to engage with a tissue portion of the heart adjacent to the left atrial appendage; wherein the second rotational position can be at least one-quarter or approximately one-quarter of a complete rotation (i.e., 90° or approximately) 90° relative to the first rotational position; wherein the second rotational position can be at least one-half or approximately one-half of a complete rotation (i.e., 180° or approximately) 180° relative to the first rotational position; wherein the second rotational position can be from one-quarter or approximately one-quarter of a complete rotation (i.e., 90° or approximately) 90° to one or more or approximately one or more complete rotations (i.e., 360° or approximately 360° or more) relative to the first rotational position; wherein the catheter can be configured to exert a torque on the implant to rotate the implant from the first rotational position until a threshold predetermined torque level is reached; wherein a threshold predetermined torque level can be from 0.25 or approximately 0.25 in-oz of torque to 10 or approximately 10 in-oz of torque; and/or wherein a threshold predetermined torque level can be from 0.5 or approximately 0.5 in-oz of torque to 5 or approximately 5 in-oz of torque.

Any arrangements of the devices and systems disclosed herein can include an implant having a contact member configured to move between a first state and a second state and a catheter configured to advance the contact member into the LAA when the contact member is in the first state and to cause the contact member to move from the first state to the second state so that an outside surface of the expands against an inner wall surface of the LAA after the contact member has been advanced into the LAA, wherein the catheter is configured to exert a torque on the contact member when at least a portion of the catheter is rotated until a predetermine torque level is reached to rotate the contact member from a first rotational position to a second rotational position so that the contact member can twist at least a portion of the LAA.

Any arrangements of the devices and systems disclosed herein can include an expandable implant configured to move between a first state and a second state, a catheter configured to advance the implant into the left atrial appendage when the implant is in the first state and to cause the implant to move from the first state to the second state so that an outside surface of the implant expands against at least a portion of an inner wall surface of the left atrial appendage after the implant has been advanced into the left atrial appendage. In any arrangements of the device for closing or occluding an LAA disclosed herein, the catheter can be configured to exert a torque on the implant to rotate the implant from a first rotational position to a second rotational position so that the implant can twist at least a portion of the left atrial appendage until a predetermine torque level is reached, or in some arrangements, until the user decides to stop, whichever comes first.

Also disclosed herein are devices and systems for treating the LAA, which include a device configured to be inserted into the LAA and to engage the LAA tissue while the device is rotated to a rotated position to close the blood communication between the LAA and the left atrium. In any arrangements of the apparatus, the device can be configured to be selectively lockable in the rotated position to at least substantially maintain the device in the rotated position after implantation, the device can include a securing element configured to engage a tissue surface adjacent to the LAA to maintain the device in the rotated position after implantation, the device can be round, spherical, or disc shaped when the device is in a deployed state in the LAA, the device can be expandable from a first collapsed state to a second expanded state, and/or the device can be self-expanding from a first collapsed state to a second expanded state.

Also disclosed herein are arrangements of methods for treating the LAA, including engaging a tissue of the LAA, and rotating the tissue of the LAA to close or occlude a blood communication between the LAA and a left atrium. In any arrangements of the methods disclosed herein, rotating the tissue of the LAA to close or occlude the blood communication between the LAA and the left atrium can include rotating the tissue of the LAA to close or occlude the ostium of the LAA. Further, any arrangements of the methods disclosed herein can further include securing the LAA in a rotated position to hold the LAA in a closed or occluded state.

Any arrangements of a method of closing or occluding an LAA disclosed herein can include advancing a deployment device having an implant into the left atrial appendage, wherein the implant can be configured to be moved from a first state to a second state. In some arrangements, at least a portion of the implant can be enlarged in a radial direction when the implant is in the second state as compared to the first state. The method can further include moving the implant from the first state to the second state within the left atrial appendage so as to move at least a portion of an outside wall of the implant or one or more tissue anchors extending away from an outer surface of the implant against at least a portion of an inner wall surface of the left atrial appendage, rotating the implant from a first rotational position to a second rotational position to twist the left atrial appendage, and preventing the implant from rotating back to the first rotational position.

Any arrangements of methods of closing or occluding an LAA disclosed herein can, in some additional arrangements, include one or more of the following steps, in any combination and in any combination with any of the other steps, features, or other details of any other arrangements: wherein the implant is self-expanding and wherein moving the implant from the first state to the second state comprises advancing the implant out of a distal end of the deployment device; wherein engaging a wall portion on an inside of the LAA comprises engaging a wall portion on an inside of the LAA with one or more tissue anchors positioned on an outside surface of the implant; wherein preventing the implant from rotating back to the first rotational position comprises engaging a tissue wall with an anchor element to prevent relative movement between the implant and the tissue wall; wherein preventing the implant from rotating back to the first rotational position comprises engaging a tissue wall with an anchor element, and wherein the anchor element is configured to be secured to the implant to prevent a rotation between the implant and the anchor element; wherein preventing the implant from rotating back to the first rotational position comprises engaging a tissue wall of the heart with an anchor element, wherein the anchor element is rotationally fixed relative to the implant and configured to prevent the implant from rotating back to the first rotational position; wherein preventing the implant from rotating back to the first rotational position comprises engaging a tissue of the heart outside of the closed portion of the LAA with an anchor element, wherein the anchor element is rotationally fixed relative to the implant and configured to prevent the implant from rotating back to the first rotational position; wherein the anchor element comprises a plurality of tissue anchors on at least one surface thereof configured to engage with the internal wall of the heart outside of the LAA; wherein rotating the implant from the first rotational position to the second rotational position to twist the LAA comprises rotating the implant until an ostium of the LAA is substantially or completely closed; wherein rotating the implant from the first rotational position to the second rotational position to twist the LAA comprises rotating the implant at least approximately 90° in either direction from the first rotational position; wherein rotating the implant from the first rotational position to the second rotational position to twist the LAA comprises rotating the implant at least approximately 180° in either direction from the first rotational position; wherein rotating the implant from the first rotational position to the second rotational position to twist the LAA comprises rotating the implant from approximately 90° to approximately 360° in either direction from the first rotational position; wherein rotating the implant from the first rotational position to the second rotational position to twist the LAA comprises rotating the implant from approximately 90° to approximately 180° in either direction from the first rotational position; wherein rotating the implant from the first rotational position to the second rotational position to twist the LAA comprises exerting a torque on the implant to rotate the implant in either direction from the first rotational position until a threshold predetermined torque level is reached, holding the implant in the second rotational position, and securing the implant in approximately the second rotational position relative to a tissue surface surrounding the LAA; wherein a maximum predetermined torque level is from approximately 0.25 in-oz of torque to approximately 10 in-oz of torque; and/or wherein a maximum predetermined torque level is from approximately 0.5 in-oz of torque to approximately 5 in-oz of torque.

Any arrangements of the methods of closing or occluding an LAA disclosed herein can, in some additional arrangements, include one or more of the following steps, in any combination and in any combination with any of the other steps, features, or other details of any other arrangements: wherein the implant is self-expanding and wherein moving the implant from the first state to the second state can include advancing the implant out of a distal end of the deployment device; wherein engaging a wall portion on an inside of the left atrial appendage can include engaging at least a portion of a wall portion on an inside of the left atrial appendage or surrounding the left atrial appendage with one or more tissue anchors positioned on an outside surface of the implant; wherein preventing the implant from rotating back to the first rotational position can include engaging a tissue wall outside of the left atrial appendage with an anchor element; wherein the anchor element can be rotationally fixed to the implant to prevent relative movement between the anchor element and the implant; wherein preventing the implant from rotating back to the first rotational position can include engaging a tissue wall of the heart with an anchor element; wherein the anchor element can be rotationally fixed relative to the implant and configured to prevent the implant from rotating back to the first rotational position; wherein preventing the implant from rotating back to the first rotational position can include engaging an internal wall of the heart outside of the left atrial appendage with an anchor element; wherein the anchor element can be rotationally fixed relative to the implant and configured to prevent the implant from rotating back to the first rotational position; wherein the anchor element can include a plurality of tissue anchors on at least one surface thereof configured to engage with the internal wall of the heart outside of the left atrial appendage; and/or wherein rotating the implant from the first rotational position to the second rotational position to twist the left atrial appendage can include rotating the implant until an ostium of the LAA can be substantially or completely closed or occluded, or collapsed about an outer surface of the implant.

Any arrangements of the methods of closing or occluding an LAA disclosed herein can, in any additional arrangements, include one or more of the following steps, in any combination and in any combination with any of the other steps, features, or other details of any other arrangements: wherein rotating the implant from the first rotational position to the second rotational position to twist the left atrial appendage can include rotating the implant at least one-quarter or approximately one-quarter of a complete rotation (i.e., 90° or approximately) 90° relative to the first rotational position; wherein rotating the implant from the first rotational position to the second rotational position to twist the left atrial appendage can include rotating the implant at least one-half or approximately one-half of a complete rotation (i.e., 180° or approximately) 180° in either direction from the first rotational position; wherein rotating the implant from the first rotational position to the second rotational position to twist the left atrial appendage can include rotating the implant from one-quarter or approximately one-quarter of a complete rotation (i.e., 90° or approximately) 90° to one full turn or approximately one full turn (i.e., 360° or approximately 360°), or to more than one full turn (i.e., more than) 360° in either direction from the first rotational position; wherein rotating the implant from the first rotational position to the second rotational position to twist the left atrial appendage can include rotating the implant from one-quarter or approximately one-quarter of a complete rotation (i.e., 90° or approximately) 90° to one-half of a full turn or approximately one-half of a full turn (i.e., 180° or approximately) 180°, or to more than one full turn (i.e., more than 360°) in either direction from the first rotational position; wherein rotating the implant from the first rotational position to the second rotational position to twist the left atrial appendage can include exerting a torque on the implant to rotate the implant in either direction from the first rotational position until a threshold predetermined torque level is reached; wherein rotating the implant from the first rotational position to the second rotational position to twist the left atrial appendage can include holding the implant in the second rotational position; wherein rotating the implant from the first rotational position to the second rotational position to twist the left atrial appendage can include securing the implant in approximately the second rotational position relative to a tissue surface surrounding the left atrial appendage; wherein a maximum predetermined torque level can be from approximately 0.25 in-oz of torque to approximately 10 in-oz of torque; and/or wherein a maximum predetermined torque level can be from approximately 0.5 in-oz of torque to approximately 5 in-oz of torque.

Some arrangements of an implant for deployment within a cavity or vessel disclosed herein include an expandable body, a plurality of tissue anchors on an outside surface of the expandable body configured to engage with an inner wall surface of the cavity or vessel, and an anchor element coupled with the expandable body configured to engage with a tissue surface adjacent to the inner wall surface of the cavity or vessel.

Any arrangements of the devices and systems disclosed herein can include an expandable implant having a plurality of tissue anchors on an outside surface thereof, the expandable implant being configured to move between a first state in which the implant is substantially collapsed and a second state in which at least a portion of the implant is expanded, and a catheter configured to advance the implant into the left atrial appendage when the implant is in the first state and to cause the implant to move from the first state to the second state so that at least some of the plurality of tissue anchors engage an inner wall surface of the left atrial appendage after the implant has been advanced into the left atrial appendage. In some arrangements, the catheter can be configured to rotate the implant in a first direction from a first rotational position to a second rotational position so that the implant can twist the wall of the left atrial appendage.

Some arrangements of the devices and systems for closing or occluding an LAA disclosed herein can include an implant configured to move between a first state and a second state, and a catheter configured to advance the implant into the left atrial appendage when the implant is in the first state and to cause the implant to move from the first state to the second state so that an outside surface of the implant moves against an inner wall surface of the left atrial appendage after the implant has been advanced into the left atrial appendage. In some arrangements, the catheter can be configured to rotate the implant in a first direction from a first rotational position to a second rotational position so that the implant can twist at least a portion of the left atrial appendage when the implant is in the second state.

Any arrangements of the methods of treating the left atrial appendage disclosed herein can include engaging a tissue of the left atrial appendage and rotating the tissue of the left atrial appendage to close or significantly close, or inhibit or substantially inhibit, a blood communication between the left atrial appendage and a left atrium. Any arrangements of the method(s) disclosed herein can include, in additional arrangements, one or more of the following features, components, steps, and/or details, in any combination with any of the other features, components, steps, and/or details of any other treatment method arrangements disclosed herein: further including rotating the tissue of the left atrial appendage to close the blood communication between the left atrial appendage and the left atrium can include rotating the tissue of the left atrial appendage to close the ostium of the left atrial appendage, and/or further including securing the left atrial appendage in a rotated position to hold the left atrial appendage in a closed state.

Some arrangements of apparatuses for treating the left atrial appendage disclosed herein can include a device configured to be inserted into the left atrial appendage and to engage the left atrial appendage tissue while the device is rotated to a rotated position to close the blood communication between the left atrial appendage and the left atrium. In some arrangements, the device can be configured to be locked in the rotated position to maintain the device in the rotated position after implantation, wherein the device can include a securing element configured to engage a tissue surface adjacent to the left atrial appendage to maintain the device in the rotated position after implantation, wherein the device can be round, spherical, or disc shaped when the device is in a deployed state in the left atrial appendage, wherein the device can be expandable from a first collapsed state to a second expanded state, and/or wherein the device can be self-expanding from a first collapsed state to a second expanded state.

Disclosed herein are arrangements of devices for treating a left atrial appendage that include an implant having a contact member and a catheter configured to advance the contact member into the left atrial appendage and to cause the contact member to move against an inner wall surface of the left atrial appendage, wherein the catheter is configured to exert a torque on the contact member when at least a portion of the catheter is rotated until a predetermine torque level is reached to rotate the contact member from a first rotational position to a second rotational position so that the contact member can twist at least a portion of the left atrial appendage. In any arrangements disclosed herein, the contact member can be configured to be moved against the inner wall surface of the left atrial appendage without changing a state or shape of the contact member, and/or the contact member can be configured to be movable or expandable from a first state to a second state.

Disclosed herein are arrangements of devices for reducing an opening of the left atrial appendage that include a contact member and a securing element, wherein the contact member is configured to engage a tissue surface of the left atrial appendage, the contact member is configured to rotate at least a portion of the left atrial appendage in a first direction from a first rotational position to a second rotational position and to cause the opening of the left atrial appendage to reduce in size from a first size to a second size, and/or the securing element is configured to engage with at least a portion of tissue adjacent to the opening of the left atrial appendage and to prevent the opening of the left atrial appendage from expanding to the first size. In any arrangements disclosed herein, the contact member can be configured to engage a tissue surface on an outside surface of the left atrial appendage. Further, in any arrangements disclosed herein, the contact member can be configured to engage the tissue surface of the left atrial appendage without changing a state or shape of the contact member.

Any arrangements of the devices disclosed herein can include, in additional arrangements, one or more of the following features, components, and/or details, in any combination with any of the other features, components, and/or details of any other arrangements disclosed herein: wherein the device further includes a delivery catheter; wherein the device further includes an implant of any of the implant arrangements disclosed herein that is advanceable through the delivery catheter when the implant is in a first state; wherein the implant includes a first stage portion and a second stage portion that are each independently deployable to at least a second operable or deployed state; wherein the first stage portion is configured to be at least partially deployed before a second stage portion is deployed; wherein the first stage portion is configured to be positioned near a distal end portion of the LAA; wherein the second stage portion is configured to constrict an opening of the LAA when the second stage portion is in the second state; wherein second stage portion is configured to close the opening of the LAA when the second stage portion is in the second state; wherein second stage portion is configured to fold one or more tissue portions surrounding or adjacent to the opening of the LAA when the second stage portion is in the second state; wherein the second stage portion is configured to twist one or more portions of tissue surrounding the opening of the LAA to constrict or close the opening of the LAA when the second stage portion is in a second state; wherein the second stage portion comprises a means for constricting or closing the opening of the LAA; wherein the second stage portion comprises a hinge mechanism for constricting or closing the opening of the LAA; further including at least one of a passive activation mechanism and an active activation mechanism to activate the hinge mechanism; and/or wherein at least one of the first stage portion and the second stage portion is self-expanding.

Disclosed herein are additional arrangements of treatment methods that include advancing a deployment device having an implant into the left atrial appendage, moving at least a portion of an outside surface of the implant or one or more tissue anchors extending away from an outer surface of the implant against an inner wall surface of the left atrial appendage, rotating the implant from a first rotational position to a second rotational position to twist the left atrial appendage, and preventing the implant from rotating back to the first rotational position. In any arrangements, the method can include moving at least a portion of an outside surface of the implant or one or more tissue anchors extending away from an outer surface of the implant against an inner wall surface of the left atrial appendage without changing a shape or size of the implant, and/or moving the implant from a first state to a second state, and wherein at least a portion of the implant is enlarged in a radial direction when the implant is in the second state as compared to the first state.

Disclosed herein are additional arrangements of devices and systems for closing an LAA that can include a clamp device having a first member and a second member and be configured to move between a closed position and an open position, a first guide device configured to be advanceable into the LAA, and a second guide device configured to be advanceable into a pericardial space outside of the LAA and moved so that an end portion of the second guide device is in approximate axial alignment with an end portion of the first guide device. In any arrangements disclosed herein, at least one of the first and second members of the clamp device can be substantially rigid; the clamp device can have an opening sized so that the clamp device can be passed over the LAA when the clamp device is in the open position; and/or at least one of the first and second members of the clamp device can be configured to substantially flatten and close a portion of the LAA when the clamp device is moved to the closed position. In any additional arrangements disclosed herein, the clamp device can include only the first member and the second member. In additional arrangements, the clamp device can further include a third member and a fourth member connected together in an end to end arrangement and defining an opening in the clamp device that is sized and configured to pass over an outside surface of the LAA. In any additional arrangements disclosed herein, the device can further include a delivery catheter having an outer sheath and a guide lumen, the guide lumen configured to receive and track over the second guide device. Additionally, the first member of the clamp device can be rigid and the second member of the clamp device can comprise a suture.

Disclosed herein are additional arrangements of methods of closing or occluding an LAA. In any arrangements disclosed herein, the method can include advancing a first guide device into the LAA, advancing a second guide device into a pericardial space outside of the LAA, approximately aligning an end portion of the second guide device with an end portion of the first guide device, advancing a delivery catheter over the second guide device, advancing a clamp device having a first member and a second member from the delivery catheter, opening the clamp device from a closed position to an open position, advancing the clamp device over an outside surface of the LAA toward a neck portion of the LAA, and/or substantially flattening and closing the neck portion of the LAA by closing the clamp device from the open position to the closed position.

Any arrangements of the methods of closing or occluding the LAA can include, in additional arrangements, one or more of the following features, components, steps, and/or details, in any combination with any of the other features, components, steps, and/or details of any other arrangements disclosed herein: wherein moving the clamp device from the closed position to the open position comprises advancing the clamp device past a distal end of the delivery catheter so that the clamp device can automatically move to the open position; wherein the delivery catheter has a guide lumen, the guide lumen being configured to receive and track over the second guide device; wherein the delivery catheter has an outer sheath; wherein at least one of the first and second members of the clamp device is substantially rigid; wherein at least one of the first and second members of the clamp device has a substantially planar contact surface, the contact surface being the surface configured to contact an outside surface of the LAA; wherein the delivery catheter has an outer sheath; wherein the clamp device comprises a least four substantially rigid members connected together in an end to end arrangement and defining an opening in the clamp device that is sized and configured to pass over an outside surface of the LAA; and/or wherein the clamp device comprises at least one rigid member and at least one flexible member interconnected with the at least one rigid member.

Additionally, any implant and/or device or system arrangements disclosed herein can be adapted and/or used for treatment of any tissue condition in a body that is desired to be occluded, restricted, or closed. For example and without limitation, some arrangements of the devices and systems for treating a tissue condition disclosed herein can include an implant comprising a contact member that can be (but is not required to be) configured to move between a first state and a second state and a securing element, wherein the contact member can be configured to move from the first state to the second state so that at least a portion of the contact member engages a wall portion of the tissue condition after the contact member has been advanced into the tissue condition, the contact member can be configured to rotate at least in a first direction from a first rotational position to a second rotational position, the contact member can be configured to twist at least a portion of the tissue of the tissue condition in the first direction when the contact member is rotated from the first rotational position to the second rotational position, and/or the securing element can be configured to prevent a rotation of at least a portion of the tissue of the tissue condition in a second direction when the securing element is in an operable state, wherein the second direction is opposite to the first direction. In any arrangements, the tissue condition can be a cavity, a chamber, an opening, a passageway, a tear in the tissue, two adjacent or adjoining tissue surfaces, or otherwise.

Further, some arrangements of the devices and systems for treating a tissue condition disclosed herein can include an implant having a contact member that can be (but is not required to be) configured to move between a first state and a second state, a catheter configured to advance the contact member into the tissue condition when the contact member is in the first state and to cause the contact member to move from the first state to the second state so that an outside surface of the contact member engages at least one wall surface of the tissue condition after the contact member has been advanced into or adjacent to the tissue condition, wherein the catheter is configured to exert a torque on the contact member when at least a portion of the catheter is rotated until a predetermine torque level is reached to rotate the contact member from a first rotational position to a second rotational position so that the contact member can twist at least a portion of the tissue condition. In any arrangements, the tissue condition can be a cavity, a chamber, an opening, a passageway, a tear in the tissue, two adjacent or adjoining tissue surfaces, or otherwise.

Further, some arrangements of the devices and systems for treating a tissue condition disclosed herein can include a method of treating a tissue condition, comprising advancing a deployment device having an implant into or adjacent to the tissue condition, wherein the implant can be (but is not required to be) configured to be moved from a first state to a second state, and wherein at least a portion of the implant can be enlarged in a radial direction when the implant is in the second state as compared to the first state, moving the implant from the first state to the second state within the tissue condition so as to move at least a portion of an outside surface of the implant or one or more tissue anchors extending away from an outer surface of the implant against at least one wall surface of the tissue condition, rotating the implant from a first rotational position to a second rotational position to twist the tissue condition, and/or preventing the implant from rotating back to the first rotational position.

Additionally, any implant and/or device or system arrangements disclosed herein can be adapted and/or used for treatment of any tissue condition in a body that is desired to be occluded, reshaped, restricted, or closed. For example and without limitation, some arrangements of the devices and systems for treating a tissue condition disclosed herein can include an implant comprising a contact member that is configured to engage a wall portion of the tissue condition after the contact member has been advanced into the tissue condition, the contact member can be configured to rotate at least in a first direction from a first rotational position to a second rotational position, the contact member can be configured to twist at least a portion of the tissue of the tissue condition in the first direction when the contact member is rotated from the first rotational position to the second rotational position, and/or the securing element can be configured to prevent a rotation of at least a portion of the tissue of the tissue condition in a second direction when the securing element is in an operable state, wherein the second direction is opposite to the first direction. In any arrangements, the tissue condition can be a cavity, a chamber, an opening, a passageway, a tear in the tissue, two adjacent or adjoining tissue surfaces, or otherwise.

Further, some arrangements of the devices and systems for treating a tissue condition disclosed herein can include an implant having a contact member, a catheter configured to advance the contact member into the tissue condition so that the contact member engages at least one wall surface of the tissue condition after the contact member has been advanced into or adjacent to the tissue condition, wherein the catheter is configured to exert a torque on the contact member when at least a portion of the catheter is rotated until a predetermine torque level is reached to rotate the contact member from a first rotational position to a second rotational position so that the contact member can twist at least a portion of the tissue condition. In any arrangements, the tissue condition can be a cavity, a chamber, an opening, a passageway, a tear in the tissue, two adjacent or adjoining tissue surfaces, or otherwise.

Further, some arrangements of the devices and systems for treating a tissue condition disclosed herein can include a method of treating a tissue condition, comprising advancing a deployment device having an implant into or adjacent to the tissue condition, and wherein at least a portion of the implant engages a wall surface of the tissue condition, rotating the implant from a first rotational position to a second rotational position to twist the tissue condition, and/or preventing the implant from rotating back to the first rotational position.

Disclosed herein are arrangements of a device for treating a left atrial appendage that can include an implant that can have a contact member configured to engage an inside tissue surface of the left atrial appendage and configured to rotate in at least a first direction from a first position to at least a second position so as to twist the left atrial appendage when the contact member is engaged with an inside tissue surface of the left atrial appendage, and a securing element configured to move between a first position in which the securing element is decoupled from the contact member and a second position in which the securing element is coupled with the contact member. In some arrangements, the contact member can be configured to rotate at least in the first direction from the first position to the second position when a torque is applied to the contact member.

Any arrangements of the methods, devices and systems for treating a left atrial appendage disclosed herein can include, in additional arrangements, one or more of the following steps, features, components, and/or details, in any combination with any of the other steps, features, components, and/or details of any other arrangements disclosed herein: wherein the contact member can be configured to rotate at least in the first direction from a first position to at least a second position to twist the left atrial appendage and reduce a size of an ostium of the left atrial appendage from a first size to a second size when the contact member is engaged with an inside tissue surface or the left atrial appendage; wherein the implant can be configured to inhibit the ostium of the left atrial appendage from enlarging back to the first size; wherein the device can be configured such that the contact member can be removed from the left atrial appendage after the securing element has been deployed to the operable state of the securing element; wherein the device can be configured such that the contact member can be removed from the left atrial appendage after the securing element has been deployed to the operable state of the securing element, and wherein the securing element can be configured to prevent a rotation of the tissue of the left atrium and/or the left atrial appendage that has been constricted as a result of the rotation of the contact member from the first position to the second position; wherein the contact member can be configured to move between a first state and a second state, wherein an outside dimension of the contact member can be greater in the second state than in the first state; wherein the contact member can be biased to remain in the second state after deployment into the left atrial appendage; wherein the contact member can be configured to have an approximately fixed and unchangeable size and shape; wherein the contact member can be self-expandable such that the contact member will automatically expand from the first state to the second state when a restraint is removed from the implant without further intervention from a user; wherein the contact member can be configured to automatically move from the first state to the second state when a restraint is removed from the contact member, and wherein the contact member can be configured to engage a wall portion of the left atrial appendage when the contact member is in the second state and advanced into the left atrial appendage; wherein the contact member can have a plurality of tissue anchors on an outer surface thereof; and/or wherein the plurality of tissue anchors on or adjacent to the outer surface of the contact member are configured to engage an inner wall surface of the left atrial appendage after the contact member has been moved to the second state.

Any arrangements of the methods, devices and systems for treating a left atrial appendage disclosed herein can include, in additional arrangements, one or more of the following steps, features, components, and/or details, in any combination with any of the other steps, features, components, and/or details of any other arrangements disclosed herein: wherein the device can be configured to cause a tissue of the left atrium and/or the left atrial appendage to constrict around an outer surface of a body portion of the implant when the contact member is rotated to the second position; wherein the securing element can be configured to engage with the tissue that has constricted around the outer surface of the body portion of the implant to prevent rotation of the implant in a second direction that is opposite to the first direction; wherein, in an operable position, the securing element can be configured to at least inhibit the contact member from rotating back to the first position; wherein the securing element can be configured to prevent a rotation of at least a portion of the left atrial appendage in a second direction when the securing element is implanted in a tissue surface surrounding an ostium of the left atrial appendage, wherein the second direction is opposite to the first direction; wherein the securing element can be configured to at least expand from a first state to a second state, wherein an outside dimension of the securing element can be greater in the second state than in the first state; wherein the securing element can include a plurality of arms; wherein the securing element can have a plurality of struts and a plurality of interconnections between adjacent struts of the plurality of struts; wherein at least an end portion of each of the plurality of arms of the securing element point generally away from the contact member when the securing element is in the first state and point generally toward the contact member when the securing element is in the second state; including a restraint configured to be movable in an axial direction relative to at least a portion of the securing element from a first position in which the plurality of arms of the securing element are restrained by the restraint to a second position in which the plurality of arms of the securing element are not restrained by the restraint;

Any arrangements of the methods, devices and systems for treating a left atrial appendage disclosed herein can include, in additional arrangements, one or more of the following steps, features, components, and/or details, in any combination with any of the other steps, features, components, and/or details of any other arrangements disclosed herein: including a restraint configured to be movable in an axial direction relative to at least a portion of the securing element between a first position in which the plurality of arms of the securing element are restrained by the restraint and a second position in which the plurality of arms of the securing element are not restrained by the restraint, wherein the second axial position can be closer to the first portion of the implant than the first axial position; wherein the restraint can be configured to be movable in an axial direction relative to at least a portion of the securing element from the second position in which the plurality of arms of the securing element are not restrained by the restraint to the first position in which the plurality of arms of the securing element are restrained by the restraint to facilitate repositioning and/or removal of the implant; including a threaded member configured such that rotating the threaded member will cause the restraint to move from the first position to the second position; wherein the restraint can be rotatable relative to the threaded member so that the restraint is not forced to rotate as the threaded member is rotated; wherein the securing element can have a helical shape and can be configured to rotate about a body portion of the implant during the implantation procedure; wherein only a portion of the securing element extends into the left atrium after deployment of the device, and all other portions of the device are internal to the left atrial appendage after deployment of the device; wherein the securing element can be movable between a first state in which the securing element can spin freely relative to the contact member and a second state in which the securing element can be rotationally locked to the contact member; wherein one of the securing element and the contact member can have recesses and the other of the securing element and the contact member can have protrusions configured to selectively engage with the recesses such that the protrusions are spaced apart from the recesses when the securing element is in the first state and the protrusions are engaged with the recesses when the securing element is in the second state; further including a retention element configured to selectively couple the securing element to the contact member at any of a range of selectable distances when the securing element is in the second position; wherein the retention element can have a threaded shaft configured to threadedly engage with the contact member, the threaded shaft being coupled with the securing element; wherein the retention element can be adjustable so as to move the securing element between at least a first position and a second position, wherein the securing element can be closer to the contact member when the retention element is in the second position as compared to when the retention element is in the first position; wherein the retention element can have a threaded member, wherein a rotation of the threaded member in a first direction causes the securing element to move toward the contact member and a rotation of the threaded member in a second direction causes the securing element to move away from the contact member; wherein the retention element can be configured to slide at least in an axial direction over an inner core component of a delivery catheter; wherein the second position can be at least one-quarter of a complete rotation relative to the first position; wherein the second position can be at least one-half of a complete rotation relative to the first position; wherein the second position can be from approximately one-quarter of a complete rotation to one or more complete rotations relative to the first position; including a catheter selectively coupled with the contact member and configured to exert a torque on the contact member to rotate the contact member from the first position until a threshold predetermined torque level is reached; wherein a threshold predetermined torque level can be from approximately 0.25 in-oz of torque to approximately 10 in-oz of torque; and/or wherein a threshold predetermined torque level can be from approximately 0.5 in-oz of torque to approximately 5 in-oz of torque; and/or wherein only approximately 10% or less of an overall length of the deployed device extends into the left atrium after deployment of the device.

Also disclosed herein are arrangements of a method of treating a left atrial appendage that can include advancing a deployment device having an implant into the left atrium, moving at least a portion of an outer surface of a first portion of the implant and/or one or more tissue anchors on or adjacent to the outer surface of the first portion of the implant against an inner wall surface of the left atrial appendage, and rotating the first portion of the implant from a first position to a second position to twist the left atrial appendage from a first position to a second position, and moving a second portion of the implant from a first state in which the second portion of the implant spins freely relative to the first portion of the implant to a second state in which the second portion of the implant can be rotationally locked to the first portion of the implant. Any arrangements of the methods, devices and systems for treating a left atrial appendage disclosed herein can include, in additional arrangements, one or more of the following steps, features, components, and/or details, in any combination with any of the other steps, features, components, and/or details of any other arrangements disclosed herein: wherein the second portion of the implant can be spaced apart from the first portion of the implant when the second portion of the implant is in the first state and the second portion of the implant is engaged with the first portion of the implant when the second portion of the implant is in the second state; including rotating the first portion of the implant until at least a portion of the left atrial appendage constricts around a portion of the implant; including rotating the first portion of the implant until an ostium of the left atrial appendage constricts around a portion of the implant; wherein the method can have engaging with the second portion of the implant a tissue that has constricted as a result of the rotation of the first portion of the implant; and/or wherein moving the second portion of the implant from the first state to the second state causes the second portion of the implant to inhibit a rotation of the left atrial appendage toward the first position of the left atrial appendage.

Also disclosed herein are arrangements of a device for treating a left atrial appendage that can include an implant device that can include a first implant member configured to engage an inside tissue surface of a first portion of the left atrial appendage and a second implant member configured to engage an inside tissue surface of a second portion of the left atrial appendage spaced apart from the first portion of the left atrial appendage. In some arrangements, the device can be configured to rotate the first implant member in a first direction. In some arrangements, the device can be configured to rotate the second implant member in a second direction that is opposite to the first direction.

Any arrangements of the methods, devices and systems for treating a left atrial appendage disclosed herein can include, in additional arrangements, one or more of the following steps, features, components, and/or details, in any combination with any of the other steps, features, components, and/or details of any other arrangements disclosed herein: further including a first core member coupled with the first implant member and configured to cause a rotation of the first implant member when the first core member is rotated; wherein the first implant member can be selectively removably coupled with the first core member so that the first implant member can remain in the left atrial appendage after the first core member has been withdrawn; further including a second core member coupled with the second implant member and configured to cause a rotation of the second implant member when the second core member is rotated; wherein the second implant member can be selectively removably coupled with the second core member so that the second implant member can remain in the left atrial appendage after the second core member has been withdrawn; and/or further including a securing element configured to inhibit a rotation of the first implant member and/or the second implant member in an operable state.

Disclosed herein are arrangements of a device for treating a left atrial appendage that can include an implant device that can include a first implant member configured to engage an inside tissue surface of a first portion of the left atrial appendage and a second implant member configured to engage an inside tissue surface of a second portion of the left atrial appendage spaced apart from the first portion of the left atrial appendage. In some arrangements, the device can be configured to rotate the first implant member in a first direction. Further, in some arrangements, the device can be configured to also rotate the second implant member in the first direction. Any arrangements of the methods, devices and systems for treating a left atrial appendage disclosed herein can include, in additional arrangements, one or more of the following steps, features, components, and/or details, in any combination with any of the other steps, features, components, and/or details of any other arrangements disclosed herein: further including a first core member coupled with the first implant member and configured to cause a rotation of the first implant member when the first core member is rotated; wherein the first implant member can be selectively removably coupled with the first core member so that the first implant member can remain in the left atrial appendage after the first core member has been withdrawn; further including a second core member coupled with the second implant member and configured to cause a rotation of the second implant member when the second core member is rotated; wherein the second implant member can be selectively removably coupled with the second core member so that the second implant member can remain in the left atrial appendage after the second core member has been withdrawn; and/or further including a securing element configured to inhibit a rotation of the first implant member and/or the second implant member in an operable state.

Disclosed herein are arrangements of a device for treating a left atrial appendage that can include an implant that can include a contact member and a securing element coupled with or couplable with the contact member, the securing element including a plurality of struts and a plurality of interconnections between adjacent struts of the plurality of struts. In some arrangements, the contact member can be configured to rotate at least in a first direction from a first rotational position to a second rotational position to twist at least a portion of the left atrial appendage in the first direction when the contact member is rotated from the first rotational position to the second rotational position. Any arrangements of the methods, devices and systems for treating a left atrial appendage disclosed herein can include, in additional arrangements, one or more of the following steps, features, components, and/or details, in any combination with any of the other steps, features, components, and/or details of any other arrangements disclosed herein: wherein the contact member can be configured to configured to move at least from a first state to a second state so that at least a portion of the contact member can expand radially to engage a wall portion inside the left atrial appendage; wherein the plurality of interconnections provide a point of connection between the adjacent struts of the plurality of struts; wherein the plurality of struts can have a plurality of pairs of struts, wherein each of the pairs of struts can have two struts that are interconnected at a distal end portion of the struts; wherein the plurality of struts can have a first strut, a second strut, and a third strut, the second strut can be positioned between the first strut and the third strut and the second strut can be interconnected with the first strut at a distal end of the first and second struts; wherein the second strut can be interconnected with the third strut at a middle portion of the second and third struts; wherein the implant further can have a retention element coupled with the securing element, the retention element configured to move the securing element in an axial direction toward or away from the contact member or to hold the securing element in a stationary position relative to the contact member; wherein the securing element can be configured to prevent a rotation of at least a portion of the left atrial appendage in a second direction when the securing element is in an operable state, wherein the second direction is opposite to the first direction; wherein the contact member can be self-expandable such that at least a portion of the contact member automatically expands from the first state to the second state when a restraint is removed from the contact member; wherein the implant can be substantially collapsed when the implant is in the first state and is expanded when the implant is in the second state such that a size of the implant can be bigger when the implant is in the second state than when the implant is in the first state; wherein the contact member can be biased to remain in the second state after deployment into the left atrial appendage; wherein the contact member can be configured to be rotated in a clockwise or a counter-clockwise direction; wherein the device can be configured to cause a tissue of the left atrium and/or the left atrial appendage to constrict around an outer surface of a body portion of the implant when the contact member is rotated to the second rotational position, and the securing element is configured to engage with the tissue that has constricted around the outer surface of the body portion of the implant to prevent rotation of the implant in the second direction; wherein the securing element can have a plurality of tissue anchors configured to engage with an internal wall of the heart adjacent to the left atrial appendage; wherein the securing element can have a helical shape and can be configured to rotate about a body portion of the implant during the implantation procedures; wherein the implant can be configured to rotate in a first direction from the first rotational position to the second rotational position; and/or wherein the implant can be configured to prevent rotation of the implant in a second direction after the implant has been fully deployed, wherein the second direction is opposite to the first direction.

Any arrangements of the methods, devices and systems for treating a left atrial appendage disclosed herein can include, in additional arrangements, one or more of the following steps, features, components, and/or details, in any combination with any of the other steps, features, components, and/or details of any other arrangements disclosed herein: wherein the contact member can have a plurality of tissue anchors on an outside surface thereof; wherein the plurality of tissue anchors on the outside surface of the contact member are configured to engage an inner wall surface of the left atrial appendage after the contact member has been moved to the second state; wherein the tissue anchors of the contact member have a proximal facing surface that is angled toward a proximal end of the contact member by 5°; wherein the tissue anchors wherein the tissue anchors of the contact member have a proximal facing surface that is angled toward a proximal end of the contact member at an angle from 2° to 10°; wherein the implant can have a securing element configured to engage with a tissue portion of the heart adjacent to the left atrial appendage; wherein the second rotational position can be at least one-quarter of a complete rotation relative to the first rotational position; wherein the second rotational position can be at least one-half of a complete rotation relative to the first rotational position; wherein the second rotational position can be from approximately one-quarter of a complete rotation to one or more complete rotations relative to the first rotational position; including a catheter selectively coupled with the contact member and configured to exert a torque on the contact member to rotate the contact member from the first rotational position until a threshold predetermined torque level is reached; wherein a threshold predetermined torque level can be from approximately 0.25 in-oz of torque to approximately 10 in-oz of torque; wherein a threshold predetermined torque level can be from approximately 0.5 in-oz of torque to approximately 5 in-oz of torque; including a retention element configured to bias the securing element toward a tissue wall of the LAA; including a retention element configured to bias the securing element toward the contact member; including a retention element configured to couple the securing element with the contact member; wherein the retention element can have a threaded shaft; wherein the device can be configured such that a rotation of the retention element in a first direction causes the securing element to move toward the contact member; wherein the contact member can be configured to rotate at least in a first direction from a first rotational position to a second rotational position when a torque is applied to the contact member; wherein the device can be configured such that the contact member can be removed from the left atrial appendage after the securing element has been deployed to the operable state of the securing element; wherein the device can be configured such that the contact member can be removed from the left atrial appendage after the securing element has been deployed to the operable state of the securing element, and wherein the securing element can be configured to prevent a rotation of the tissue of the left atrium and/or the left atrial appendage that has been constricted as a result of the rotation of the contact member from the first rotational position to the second rotational position; wherein only a portion of the securing element extends into the left atrium after deployment of the device, and all other portions of the device are internal to the left atrial appendage after deployment of the device; wherein only approximately 10% or less of an overall length of the deployed device extends into the left atrium after deployment of the device; wherein the device can be configured for use by a surgical robot device or system; wherein the contact member and the securing element are integrally and/or monolithically formed; and/or wherein the device can be configured to cause a tissue of the left atrium and/or the left atrial appendage to constrict around an outer surface of a body portion of the implant when the contact member is rotated to the second rotational position, and the securing element can be configured to compress the tissue that has constricted around the outer surface of the body portion of the implant between a distal surface of the securing element and the contact member to prevent rotation of the implant in the second direction.

Some arrangements enclosed herein include a surgical robotic device that can include one or more robotic arms and the device of any of the arrangements disclosed herein, wherein the device can be configured for use by the surgical robotic device.

Some arrangements of methods of treating a left atrial appendage disclosed herein can include rotating the left atrial appendage and securing the left atrial appendage in a rotated position. Any arrangements of the methods of treating, closing, or occluding the LAA can include, in additional arrangements, one or more of the following features, components, steps, and/or details, in any combination with any of the other features, components, steps, and/or details of any other arrangements disclosed herein: wherein rotating the left atrial appendage comprises rotating the left atrial appendage to deform or occlude the left atrial appendage; wherein securing the left atrial appendage in a rotated position comprises securing the left atrial appendage in a rotated position in which the left atrial appendage is reduced in volume; wherein securing the left atrial appendage in a rotated position comprises securing the left atrial appendage in a rotated position in which the left atrial appendage is deformed or occluded; wherein rotating the left atrial appendage comprises bending or contorting the left atrial appendage; wherein securing the left atrial appendage in a rotated position comprises securing the left atrial appendage in a position in which a blood communication between the left atrial appendage and a left atrium is inhibited, eliminated, or substantially eliminated; wherein rotating the left atrial appendage comprises engaging a wall portion on an inside of the left atrial appendage and/or an ostium of the left atrial appendage with a contact member and rotating the contact member; wherein the contact member is positioned on an implant coupled to the delivery system; wherein the contact member is self-expanding, balloon expandable, mechanically expanded, and/or a balloon; wherein rotating the left atrial appendage comprises engaging a wall portion on an inside of the left atrial appendage with one or more tissue anchors, one or more tissue grippers, and/or one or more other tissue holding features; wherein rotating the left atrial appendage comprises advancing a device into the left atrial appendage and rotating at least a component of the device to rotate the left atrial appendage; wherein rotating at least a component of the device comprises rotating at least the component of the device from approximately 90° to approximately 360° in either direction from an initial position; wherein rotating the left atrial appendage comprises rotating a portion of the left atrial appendage about an axis to twist the left atrial appendage; wherein rotating a portion of the left atrial appendage about one or more axes from an initial position comprises rotating the portion of the left atrial appendage from approximately 90° to approximately 360° in either direction from the initial position; wherein rotating a portion of the left atrial appendage comprises rotating the left atrial appendage until an opening of the left atrial appendage is substantially or completely closed; wherein rotating a portion of the left atrial appendage comprises rotating the left atrial appendage until a blood communication between the left atrial appendage and a left atrium is inhibited; wherein rotating a portion of the left atrial appendage comprises rotating the left atrial appendage until a communication of blood or other matter between the left appendage and the left atrium is eliminated or substantially eliminated; wherein securing the left atrial appendage in a rotated position comprises engaging tissue of the heart that has been twisted; wherein engaging tissue of the heart that has been twisted comprises engaging tissue wall with an anchor element or gripping element; wherein securing the left atrial appendage in a rotated position comprises securing a tissue of the heart outside of an occluded portion of the left atrial appendage with an anchor element; wherein securing the left atrial appendage in a rotated position comprises securing a tissue of an occluded portion of the left atrial appendage with an anchor element; and/or wherein the anchor element comprises a plurality of tissue grippers on at least one surface thereof configured to engage with the internal wall of the heart outside of the left atrial appendage.

Some arrangements of the method of reducing an ostium of a left atrial appendage disclosed herein can include twisting tissue of the heart to constrict the ostium of the left atrial appendage and securing tissue that has deformed or constricted as a result of twisting tissue of the heart. Any arrangements of the methods of treating, closing, or occluding the LAA can include, in additional arrangements, one or more of the following features, components, steps, and/or details, in any combination with any of the other features, components, steps, and/or details of any other arrangements disclosed herein: wherein securing the tissue that has deformed or constricted comprises advancing a securing element into the tissue that has deformed or constricted as a result of twisting tissue of the heart; wherein the securing element comprises a tissue anchor or tissue gripper; wherein securing the tissue that has deformed or constricted as a result of twisting tissue of the heart comprises advancing a securing element into the tissue that has deformed or constricted to compress the tissue that has deformed or constricted; and/or wherein securing tissue that has deformed or constricted as a result of twisting tissue of the heart comprises advancing one or more sutures or one or more staples into the tissue that has deformed or constricted as a result of twisting tissue of the heart.

Some arrangements of the method of treating a left atrial appendage disclosed herein can include twisting the left atrial appendage such that the left atrial appendage becomes reduced in volume and securing the left atrial appendage in a reduced volume configuration. In some arrangements, securing the left atrial appendage in a reduced volume configuration can include occluding the left atrial appendage with an implant that is smaller in size than a size of the inside of the left atrial appendage. In some arrangements, the method of treating the left atrial appendage can include unsecuring and untwisting the left atrial appendage.

Additional features, functionalities, and applications of the disclosed technology are discussed herein in more detail.

DETAILED DESCRIPTION OF THE PREFERRED ARRANGEMENT

Figure 1:
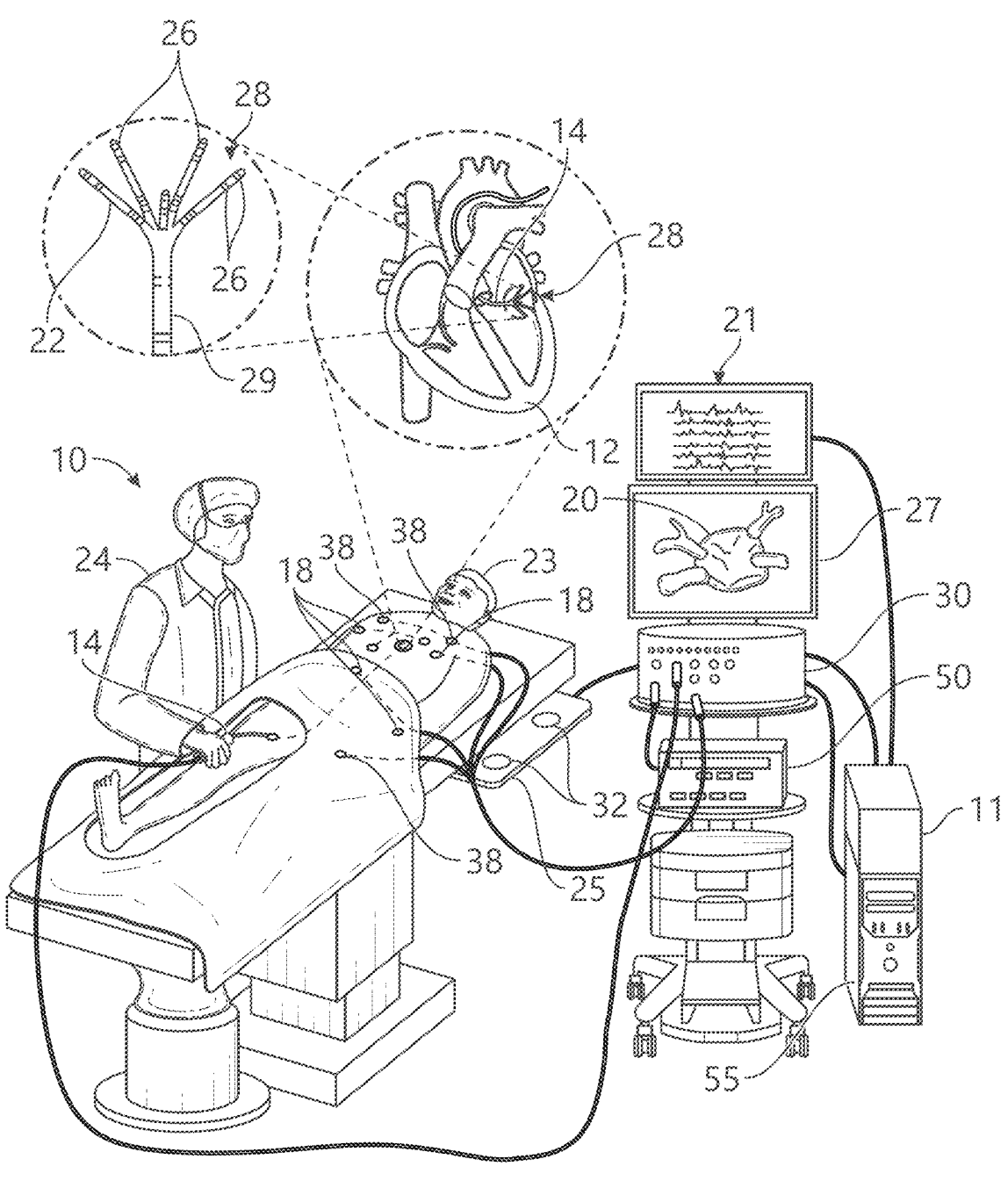
FIG. 1 shows an example of an electrophysiology (EP) mapping and ablation system.

The following detailed description should be read with reference to the drawings, in which like elements in different drawings are identically numbered. The drawings, which are not necessarily to scale, depict selected examples and are not intended to limit the scope of the disclosure. The detailed description illustrates by way of example, not by way of limitation, the principles of the disclosure. This description will clearly enable one skilled in the art to make and use the invention, and describes several examples, adaptations, variations, alternatives and uses of the invention, including what is presently believed to be the best mode of carrying out the invention.

Described herein are novel devices, systems, and methods for ablating myocardial tissue using an implant device adapted for closing or occluding a left atrial appendage (LAA). Some arrangements of the novel devices, systems, and methods for closing or occluding an LAA disclosed herein include a percutaneous transcatheter device intended to reduce the risk of thromboembolism from the LAA in patients with non-valvular atrial fibrillation (NVAF) who are at increased risk for stroke and systemic embolism and are recommended for anticoagulation therapy.

Some arrangements comprise a method that includes advancing a delivery system to the right or left atrium, or a ventricle, of the heart, advancing and deploying an expandable element or contact member of the implant device (which can be, in some arrangements, covered with barbs, texture, or other tissue engaging features or, alternatively, can be smooth) and which can have a generally spherical or orb shaped shape. In one aspect, the contact member can comprise one or more electrodes configured for engaging myocardial tissue. The electrodes can be energized to perform ablation of cardiac tissue at an ablation site. In some embodiments, the device may be used to perform ablation in a ventricle, typically prior to advancing the device into the left atrium for atrial ablation and/or LAA elimination. In ventricular applications, the ablation may be performed at sites associated with ventricular arrhythmias before the device is repositioned in the atrium for subsequent treatment.

As discussed herein, the term "ablate" or "ablation", as it relates to the devices and corresponding systems of this disclosure, refers to components and structural features configured to reduce or prevent the generation of erratic cardiac signals in the cells by utilizing thermal or non-thermal energy. In some embodiments, the devices and systems of this disclosure use a non-thermal energy, such as irreversible electroporation (IRE), referred throughout this disclosure interchangeably as pulsed electric field (PEF) and pulsed field ablation (PFA). In other embodiments, thermal energy, such as radio frequency (RF) or cryoablation, can be used. Optionally, the electrodes may be configured to gather intracardiac electrograms for diagnosis, cardiac electroanatomical mapping and/or assessing the impact of ablation on the signals' propagation in or around the targeted tissue. In addition, temperature measurements during ablation may provide data enabling the efficacy of the ablation. Typically, for an ablation procedure using a thermal technique, the electropotentials and the temperatures are measured before, during, and after the actual ablation. It is further within the scope of the present disclosure to also use the electrodes of the implant device to perform combinations of different ablation techniques (e.g., IRE and RF ablation) sequentially (e.g., certain electrodes in IRE mode and other electrodes in RF mode) or simultaneously (e.g., groups of electrodes in IRE mode and other electrodes in RF mode).

As discussed herein, the terms "bipolar" and "unipolar" when used to refer to ablation schemes describe ablation schemes which differ with respect to electrical current path and electric field distribution. "Bipolar" refers to ablation schemes utilizing a current path between two electrodes that are both positioned at a treatment site; current density and electric flux density is typically approximately equal at each of the two electrodes. "Unipolar" refers to ablation schemes utilizing a current path between two electrodes where one electrode including a high current density and high electric flux density is positioned at a treatment site, and a second electrode (sometimes referred to as a "grounding electrode" or "grounding pad") including comparatively lower current density and lower electric flux density is positioned remotely from the treatment site.

As discussed herein, the terms "biphasic pulse" and "monophasic pulse" refer to respective electrical signals. "Biphasic pulse" refers to an electrical signal including a positive-voltage phase pulse (referred to herein as "positive phase") and a negative-voltage phase pulse (referred to herein as "negative phase"). "Monophasic pulse" refers to an electrical signal including only a positive or only a negative phase. Preferably, a system providing the biphasic pulse is configured to prevent application of a direct current voltage (DC) to a patient. For instance, the average voltage of the biphasic pulse can be zero volts with respect to ground or other common reference voltage. Additionally, or alternatively, the system can include a capacitor or other protective component. Where voltage amplitude of the biphasic and/or monophasic pulse is described herein, it is understood that the expressed voltage amplitude is an absolute value of the approximate peak amplitude of each of the positive-voltage phase and/or the negative-voltage phase. Each phase of the biphasic and monophasic pulse preferably has a square shape including an essentially constant voltage amplitude during a majority of the phase duration. Phases of the biphasic pulse are separated in time by an interphase delay. The interphase delay duration is preferably less than or approximately equal to the duration of a phase of the biphasic pulse. The interphase delay duration is more preferably about 25% of the duration of the phase of the biphasic pulse.

Ablating or ablation as it relates to the devices and corresponding systems of this disclosure is used throughout this disclosure in reference to ablation of cardiac tissue for certain conditions including, but not limited to, arrhythmias, atrial flutter ablation, pulmonary vein isolation, supraventricular tachycardia ablation, and ventricular tachycardia ablation. The term "ablate" or "ablation" also includes known methods, devices, and systems to achieve various forms of bodily tissue ablation as understood by a person skilled in the relevant art.

To ablate using non-thermal IRE/PFA, biphasic voltage pulses are applied to disrupt cellular structures of the myocardium. The biphasic pulses are non-sinusoidal and can be tuned to target cells based on electrophysiology of the cells. In contrast, to ablate using RF, a sinusoidal voltage waveform is applied to produce heat at the treatment area, heating all cells in the treatment area. PFA therefore has the capability to spare adjacent heat sensitive structures or tissues which would be of benefit in the reduction of possible complications known with ablation or isolation modalities. Additionally, or alternatively, monophasic pulses can be utilized.

Electroporation can be induced by applying a pulsed electric field across biological cells to cause reversable (temporary) or irreversible (permanent) creation of pores in the cell membrane. The cells have a transmembrane electrostatic potential that is increased above a resting potential upon application of the pulsed electric field. While the transmembrane electrostatic potential remains below a threshold potential, the electroporation is reversible, meaning the pores can close when the applied pulse electric field is removed, and the cells can self-repair and survive. If the transmembrane electrostatic potential increases beyond the threshold potential, the electroporation is irreversible, and the cells become permanently permeable. As a result, the cells die due to a loss of homeostasis and typically die by programmed cell death or apoptosis, which is believed to leave less scar tissue as compared to other ablation modalities. Generally, cells of differing types have differing threshold potential. For instance, heart cells have a threshold potential of approximately 500 V/cm, whereas for bone it is 3000 V/cm. These differences in threshold potential allow IRE to selectively target tissue based on threshold potential.

This disclosure describes systems and methods for applying electrical signals from catheter electrodes positioned in the vicinity of myocardial tissue, preferably by applying a pulsed electric field effective to induce electroporation in the myocardial tissue. The systems and methods can be effective to ablate targeted tissue by inducing irreversible electroporation. In some examples, the systems and methods can be effective to induce reversible electroporation as part of a diagnostic procedure. Reversible electroporation occurs when the voltage applied with the electrodes is below the electric field threshold of the target tissue allowing cells to repair. Reversible electroporation does not kill the cells but allows a physician to see the effect of reversible electroporation on electrical activation signals in the vicinity of the target location. Example systems and methods for reversible electroporation are disclosed in U.S. Patent Publication 2021/0162210, the entirety of which is incorporated herein by reference.

The pulsed electric field, and its effectiveness to induce reversible and/or irreversible electroporation, can be affected by physical parameters of the system and biphasic pulse parameters of the electrical signal. Physical parameters can include electrode contact area, electrode spacing, electrode geometry, etc. Examples presented herein generally include physical parameters adapted to effectively induce reversible and/or irreversible electroporation. Biphasic pulse parameters of the electrical signal can include voltage amplitude, pulse duration, pulse interphase delay, inter-pulse delay, total application time, delivered energy, etc. In some examples, parameters of the electrical signal can be adjusted to induce both reversible and irreversible electroporation given the same physical parameters. Examples of various systems and methods of ablation including IRE are presented in U.S. Patent Publications 2021/0161592A1, 2021/0169550A1, 2021/0169567A1, 2021/0169568A1, 2021/0177503A1, 2021/0186604A1, and 2021/0196372A1, the entireties of each of which are incorporated herein by reference.

In another aspect, following use of one or more electrodes of the contact member for performing ablation at an ablation site, the contact member can be further advanced and deployed into the left atrial appendage, allowing the contact member to engage distally and/or radially with inner wall surfaces of the LAA, and applying a rotation to an inner catheter member connected to the contact member to twist the LAA to close and/or occlude the LAA at or near the ostium. By closing the LAA, some arrangements disclosed herein can effectively eliminate or significantly or nearly completely eliminate a communication of blood or other matter between the left atrium and the LAA. Any methods of deployment disclosed herein can also include deployment of a securing element (which is also referred to herein as a locking element or anchoring element) that is configured to inhibit or prevent the unwinding of the expandable element relative to the LAA and the LA ostial tissue, thereby inhibiting or preventing the untwisting of the LAA.

The devices, systems, and methods disclosed herein can be used, or can be adapted, for other applications within the body or on the surface of the body of any human, animal, reptile, or other living being. Other applications include, without limitation, closing openings in other tissues aside from the LAA, occluding or closing openings, passageways, and/or chambers within the heart or other organs, occluding or closing holes or other slits or openings in vessels and passageways, and/or treating other conditions.

The clinical benefit of some arrangements is a resultant implant which can perform ablation of cardiac tissue in the heart and, once implanted, is not in direct blood contact with the left atrial blood or flow except a possible portion of the securing feature. The securing element of any arrangements can be configured to limit the exposure of the securing element to the blood within the left atrium (i.e., to limit the amount of the securing element that projects into the left atrium). In some arrangements, during implantation, the entire implant can be surrounded by tissue of the LAA tissue so that no portion, or only a minimal portion (for example, less than 10% of the surface area, or less than 40% of the surface area) of the implant is exposed to blood flow within the left atrium. This can have clinical benefits to the patient as there should be no post drug regiment required. Any of the devices used in any of the methods described here may be advanced under any of a variety of visualization techniques, e.g., fluoroscopic visualization, ultrasound, etc.

For any of the arrangements disclosed herein, access to the LAA can be gained by any number of suitable means or access points. For example and without limitation, access to the LAA for some arrangements can be gained by entering through the venous system via femoral vein and a transseptal puncture into the left atrium. Imaging could use both fluoroscopy and echo (TEE, ICE or transthoracic) to image the size, position, and location of the LAA for entry of the prosthesis or device for occlusion. FIGS. 2A-2D show a portion of an example of a path from an access site to the LAA.

Entering through the venous system via femoral vein and a transseptal puncture into the left atrium, access to the LAA for any of the arrangements of the devices, systems, and methods disclosed herein can be gained. Imaging could use both fluoroscopy and echo (TEE, ICE or transthoracic), the size, position, and location of the LAA for entry of the prosthesis for closure. FIGS. 2A-2D show this example of a path from the access site to the LAA. Other access sites for any of the arrangements of the devices, systems, and methods disclosed herein can include access through the internal jugular (IJ) vein, as shown in FIG. 2E.

Further, any device, system, and method arrangements disclosed herein can be delivered to the LA/LAA or include delivery to the LA/LAA via a transfemoral arterial pathway. In some arrangements, the transfemoral arterial pathway can include advancing the delivery device through the femoral artery, up the aorta, down the aortic valve, up the mitral valve, and into the LAA. Similarly, any device, system, and method arrangements disclosed herein can be delivered to the LA/LAA or include delivery to the LA/LAA via a transradial pathway, which can include access through a radial artery in the wrist, for example and without limitation. This access pathway is also referred to as transradial access, the transradial approach, or transradial angioplasty.

The contact member of any arrangements disclosed herein can have an expandable atraumatic shape with tissue gripping features located on the outer edges of the shape, coupled to a securing and or ratcheting feature which can hold the initial or final closed position of the implant. The contact member of any arrangements disclosed herein can be configured to grip the internal tissue of the LAA with radial force as well. In some arrangements a vacuum or suction can be provided by the catheter or any component thereof to draw a tissue portion of the LAA or atrium toward the implant. The contact member of any arrangements disclosed herein can have an atraumatic shape that can be spherical, dome shaped, basket shaped, balloon shaped, or comprise a coil of wire in the shape of a disk, can have expanded cut pattern in the shape of a stent, or anything else which can have rounded edges. In some examples, the contact member can comprise one or more struts or splines extending along the contact member's longitudinal axis, the struts configured to bow radially outward from the longitudinal axis when the contact member is transitioned from a collapsed form inside a catheter to an expanded form outside the catheter. In further embodiments, each of the plurality of struts can include a material selected from a group consisting of nitinol, cobalt chromium, stainless steel, titanium, and combinations hereof.

One or more electrodes can be coupled to each strut or the outer edges of the contact member for ablating myocardial tissue. Each electrode can include a material selected from stainless steel, cobalt chromium, gold, platinum, palladium, iridium, titanium, silver, tungsten, ruthenium, ruthenium oxide, carbon-based materials (such as graphite, carbon nanotubes, or diamond-like carbon), conductive polymers (such as PEDOT) and alloys hereof. In some embodiments, the electrodes can be configured to deliver electrical pulses for irreversible electroporation. The pulses can include a peak voltage of at least 900 volts (V), and in some cases, may exceed 12,000V depending on the waveform, pulse duration, and treatment application. The contact member can further include an electrically insulative jacket disposed between each of the electrodes and the strut or structure to which the electrode is coupled, thereby electrically isolating the electrode from the strut or structure. The contact member can also include a wire disposed inside the insulative jacket for electrically connecting each electrode, through the catheter, to an external power source. To safely transmit high-voltage pulses required for PFA, the wire can be a multi-strand or solid-core conductor made of silver-plated copper, gold-plated copper, or a high-conductivity alloy, encased in a high-dielectric-strength insulation such as polytetrafluoroethylene (PTFE), perfluoroalkoxy (PFA), or cross-linked polyethylene (XLPE). The catheter shaft can include multiple lumens to separate and shield high-voltage wires, preventing unintended electrical discharge or crosstalk. Additional shielding layers, such as a braided or coiled metal mesh (e.g., stainless steel or platinum-iridium), can be incorporated to provide electromagnetic interference (EMI) protection and mechanical reinforcement. To minimize resistive losses and maintain waveform fidelity, the wiring can be routed through a dedicated high-voltage lumen within the catheter shaft, with attention to reducing sharp bends that may degrade insulation integrity.

Any electrodes coupled to the contact member can be used to perform unipolar ablation in conjunction with an external grounding electrode or grounding pad. Alternatively, any electrode of the contact member can be used to perform bipolar ablation in conjunction with any other electrode of the contact member or any electrode of a securing element of the implant (described below). In other embodiments, the contact member itself can be energized and serve as an electrode. In such embodiments, the contact member can be used to perform unipolar ablation in conjunction with an external grounding electrode or grounding pad. Alternatively, or additionally, the contact member can be used to perform bipolar ablation in conjunction with an electrode located on the securing element of the implant or in conjunction with the securing element in embodiments in which the securing element itself can be energized and serve as an electrode.

In some arrangements, the barbs (which can be tissue anchors) on the struts or outer edges or surface of the contact member can comprise metal hooks, plastic cleats, rough texture of some material or surface features, a coating or activated adhesive which grips the inside surface of the LAA. Additionally, in any arrangements disclosed herein, the tissue anchors can be positioned on or adjacent to an end portion of the implant to engage with an end portion of the LAA. In any arrangements, the barbs can be directional allowing for tissue engagement in one rotational direction and a disengagement in the opposite rotational direction for a possible repositioning, resizing, or removal from the LAA.

The rotation used to twist closed or occlude (completely or substantially) the LAA for any arrangements disclosed herein may be as little as a quarter of a turn (i.e., revolution), a half turn, a complete turn, up to as much as multiple turns for deeper or longer LAAs. The securing feature or element (also referred to herein as an anchoring element) in any arrangements disclosed herein can have a single arm or multiple arms which can be connected to the implant body that is positioned and rotated within the closed or substantially closed LAA. The securing feature or element can also be configured to engage tissue adjacent to the ostium of the LAA. In any arrangements, the securing element can have multiple arms or members, can have an annular ring, can have a disk, or any other suitable shaped surface anchor configured to couple non-twisted tissue to the twisted implant. In some arrangements, the securing element can also have a small diameter ring which can be configured to clamp to or engage with the tissue which contacts to the center hub of the implant (adjacent to the ostium of the LAA) or it can also have a clip which folds and clips the implant to the side of the wall of the left atrium (LA).

In some arrangements disclosed herein, the device can be configured to restrict an opening of the LAA by reducing a cross-sectional area of the opening of the LAA by at least 95%, or by at least 90%, or by from at least approximately 80% to approximately 100% as compared to a cross-sectional area of the opening of the LAA before the device was implanted (including a blockage effect from the device). Further, in some arrangements, the method can include rotating the implant from the first rotational position to the second rotational position to twist the LAA until an ostium of the LAA is at least 95% blocked and/or restricted, or at least 90% blocked and/or restricted, or at least 80% blocked and/or restricted, or from approximately 70% blocked and/or restricted to approximately 100% blocked and/or restricted. Additionally, any arrangements disclosed herein can include implanting two or more implants of any of the implant arrangements disclosed herein in the LAA. For example and without limitation, any of the implant arrangements disclosed herein can be configured to be deployed or implanted in the LAA to improve the occlusion of implants already implanted in the LAA, including any implants that fit within any of the foregoing ranges of less than complete occlusion. In some arrangements, one or more additional implants or devices can be implanted adjacent to, over, around, or otherwise with an existing implant to improve a level of occlusion of the LAA.

Alternatively, in any arrangements disclosed herein, the securing element can be configured to merely compress the tissue of the left atrium and/or the left atrial appendage that has constricted around an outer surface of the contact member of the implant between a distal surface of the securing element and the contact member to prevent rotation of the implant in the second direction, i.e., after the contact member has been rotated to the second rotational position, without penetrating into such tissue. For example and without limitation, in any arrangements disclosed herein, the securing element can have a body portion that is smooth and nonobtrusive or nonpenetrating, e.g., so that the securing element does not have any tissue penetrating features on it that extend toward the tissue surfaces. In other arrangements, the arms (or, at least, the portions of the arms that extend in the axial direction when the securing element is in the second state) or other tissue penetrating portions of the securing element can be short, such as from approximately 1 mm to approximately 5 mm in length, or from approximately 1 mm to approximately 3 mm in length, or from approximately 1 mm to approximately 2 mm in length, or of any values or ranges of values between any of the foregoing ranges.

In some embodiments, the securing element comprises one or more electrodes for ablating myocardial tissue. For example, one or more electrodes can be coupled to each arm or other structural portion of the securing element. The arms or other structural portions of the securing element can include a material selected from a group consisting of nitinol, cobalt chromium, stainless steel, titanium, and combinations hereof.

Each electrode coupled to the securing element may include a material selected from stainless steel, cobalt chromium, gold, platinum, palladium, iridium, titanium, silver, tungsten, ruthenium, ruthenium oxide, carbon-based materials (such as graphite, carbon nanotubes, or diamond-like carbon), conductive polymers (such as PEDOT) and alloys hereof. The electrodes can be configured to deliver electrical pulses for irreversible electroporation. The pulses can include a peak voltage of at least 900 volts (V) or as much as 12000V or more. The securing element can further include an electrically insulative jacket disposed between each of the electrodes and the arm or structure to which the electrode is coupled, thereby electrically isolating the electrode from the arm or structure. The securing element can also include a wire disposed inside the insulative jacket for electrically connecting each electrode, through the catheter, to an external power source.

In such embodiments, any of the electrodes coupled to the securing element can be used to perform unipolar ablation in conjunction with an external grounding electrode or grounding pad. Alternatively, any electrode of the securing element can be used to perform bipolar ablation in conjunction with any other electrode of the securing element or any electrode of the contact member of the implant. In other embodiments, the securing element itself can be energized and serve as an electrode. In such embodiments, the securing element can be used to perform unipolar ablation in conjunction with an external grounding electrode or grounding pad. Alternatively, or additionally, the securing element can be used to perform bipolar ablation in conjunction with an electrode located on the contact member of the implant or in conjunction with the contact member in embodiments in which the contact member itself can be energized and serve as an electrode.

Reference is made to FIG. 1 showing an example catheter-based electrophysiology mapping and ablation system 10. System 10 can include multiple catheters, which can be percutaneously inserted by physician 24 through the patient's vascular system into a chamber or vascular structure of a heart 12. Typically, a delivery sheath catheter can be inserted into the left or right atrium near a desired location in heart 12. Thereafter, a plurality of catheters can be inserted into the delivery sheath catheter so as to arrive at the desired location. The plurality of catheters may include catheters dedicated for sensing Intracardiac Electrogram (IEGM) signals, catheters dedicated for ablating, and/or catheters dedicated for both sensing and ablating. An example catheter 14 that is configured for sensing IEGM is illustrated in FIG. 1. Physician 24 can bring a distal tip 28 of catheter 14 into contact with the heart wall for sensing a target site in heart 12. For ablation, as an example, physician 24 can similarly bring a distal end of an ablation catheter to a target site for ablating.

Catheter 14 is an exemplary catheter that includes one and preferably multiple electrodes 26 optionally distributed over a plurality of splines 22 at distal tip 28 and configured to sense the IEGM signals. Catheter 14 may additionally include a position sensor 29 embedded in or near distal tip 28 for tracking position and orientation of distal tip 28. Optionally and preferably, position sensor 29 is a magnetic based position sensor including three magnetic coils for sensing three-dimensional (3D) position and orientation.

Magnetic based position sensor 29 may be operated together with a location pad 25 including a plurality of magnetic coils 32 configured to generate magnetic fields in a predefined working volume. Real time position of distal tip 28 of catheter 14 may be tracked based on magnetic fields generated with location pad 25 and sensed by magnetic based position sensor 29. Details of the magnetic based position sensing technology are described in U.S. Pat. Nos. 5,5391,199; 5,443,489; 5,558,091; 6,172,499; 6,239,724; 6,332,089; 6,484,118; 6,618,612; 6,690,963; 6,788,967; and 6,892,091.

System 10 can include one or more electrode patches 38 positioned for skin contact on patient 23 to establish location reference for location pad 25 as well as impedance-based tracking of electrodes 26. For impedance-based tracking, electrical current can be directed toward electrodes 26 and sensed at electrode skin patches 38 so that the location of each electrode can be triangulated via the electrode patches 38. Details of the impedance-based location tracking technology are described in U.S. Pat. Nos. 7,536,218; 7,756,576; 7,848,787; 7,869,865; and 8,456,182.

A recorder 11 can display electrograms 21 captured with body surface ECG electrodes 18 and intracardiac electrograms (IEGM) captured with electrodes 26 of catheter 14. Recorder 11 may include pacing capability for pacing the heart rhythm and/or may be electrically connected to a standalone pacer.

System 10 may include an ablation energy generator 50 that can be adapted to conduct ablative energy to one or more of electrodes at a distal tip of a catheter configured for ablating. Energy produced by ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

Patient interface unit (PIU) 30 is an interface configured to establish electrical communication between catheters, electrophysiological equipment, power supply and a workstation 55 for controlling operation of system 10. Electrophysiological equipment of system 10 may include for example, multiple catheters, location pad 25, body surface ECG electrodes 18, electrode patches 38, ablation energy generator 50, and recorder 11. Optionally and preferably, PIU 30 can additionally include processing capability for implementing real-time computations of location of the catheters and for performing ECG calculations.

Workstation 55 can include memory, processor unit with memory or storage with appropriate operating software loaded therein, and user interface capability. Workstation 55 may provide multiple functions, optionally including (1) modeling the endocardial anatomy in three-dimensions (3D) and rendering the model or anatomical map 20 for display on a display device 27, (2) displaying on display device 27 activation sequences (or other data) compiled from recorded electrograms 21 in representative visual indicia or imagery superimposed on the rendered anatomical map 20, (3) displaying real-time location and orientation of multiple catheters within the heart chamber, and (4) displaying on display device 27 sites of interest such as places where ablation energy has been applied. One commercial product embodying elements of the system 10 is available as the CARTO™ 3 System, available from Biosense Webster, Inc., 31A Technology Drive, Irvine, CA 92618.

Figure 2A:
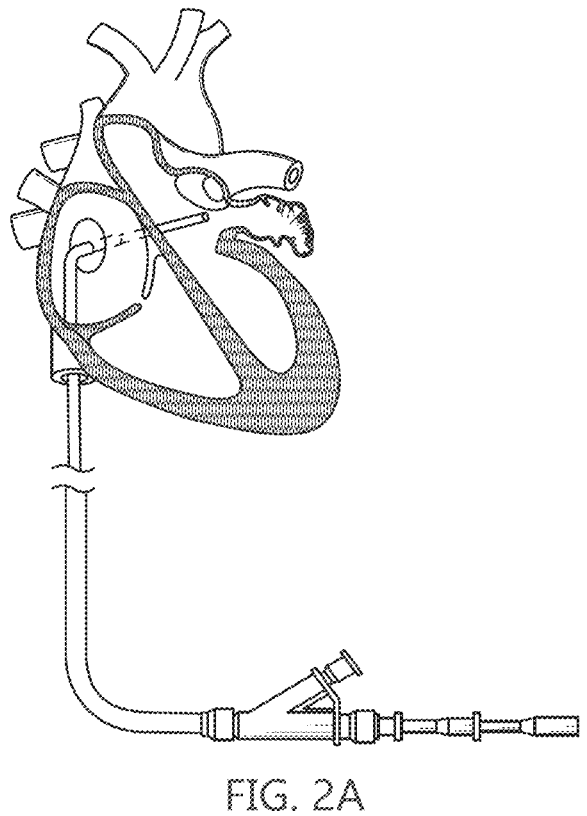
FIG. 2A illustrates a path through the venous system via femoral vein and a transseptal puncture into the left atrium that can be used to access the left atrial appendage (LAA).
Figure 2B:
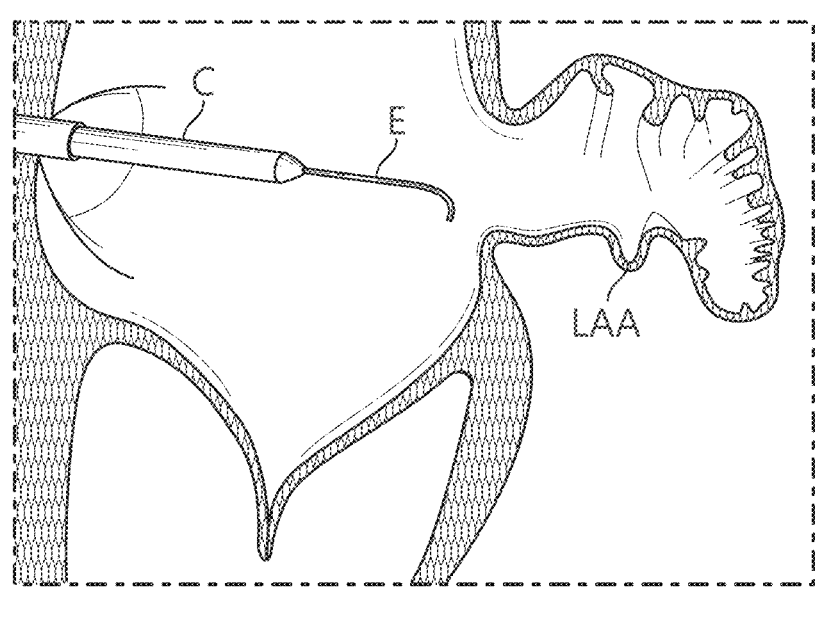
FIG. 2B shows a section view of a left atrium, showing a guidewire advancing toward the LAA.
Figure 2C:
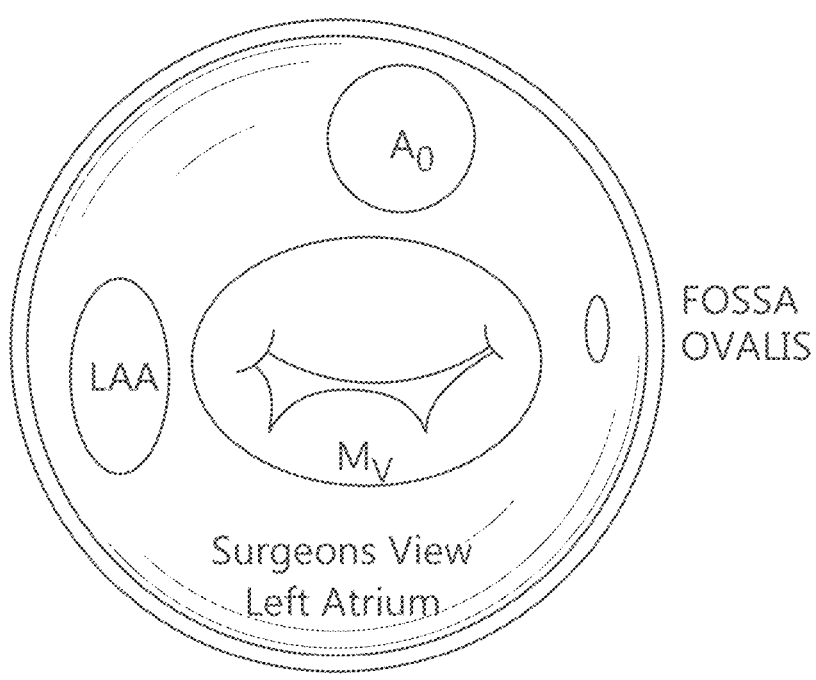
FIG. 2C shows a surgeon's left view of the left atrium.
Figure 2D:
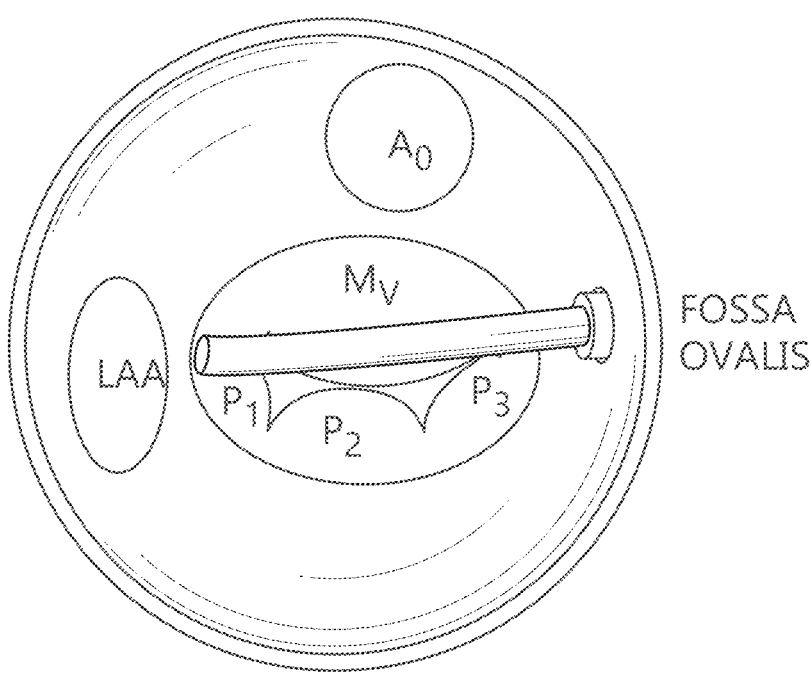
FIG. 2D shows a surgeon's left view of the left atrium, showing a delivery device advancing toward the LAA.
Figure 2E:
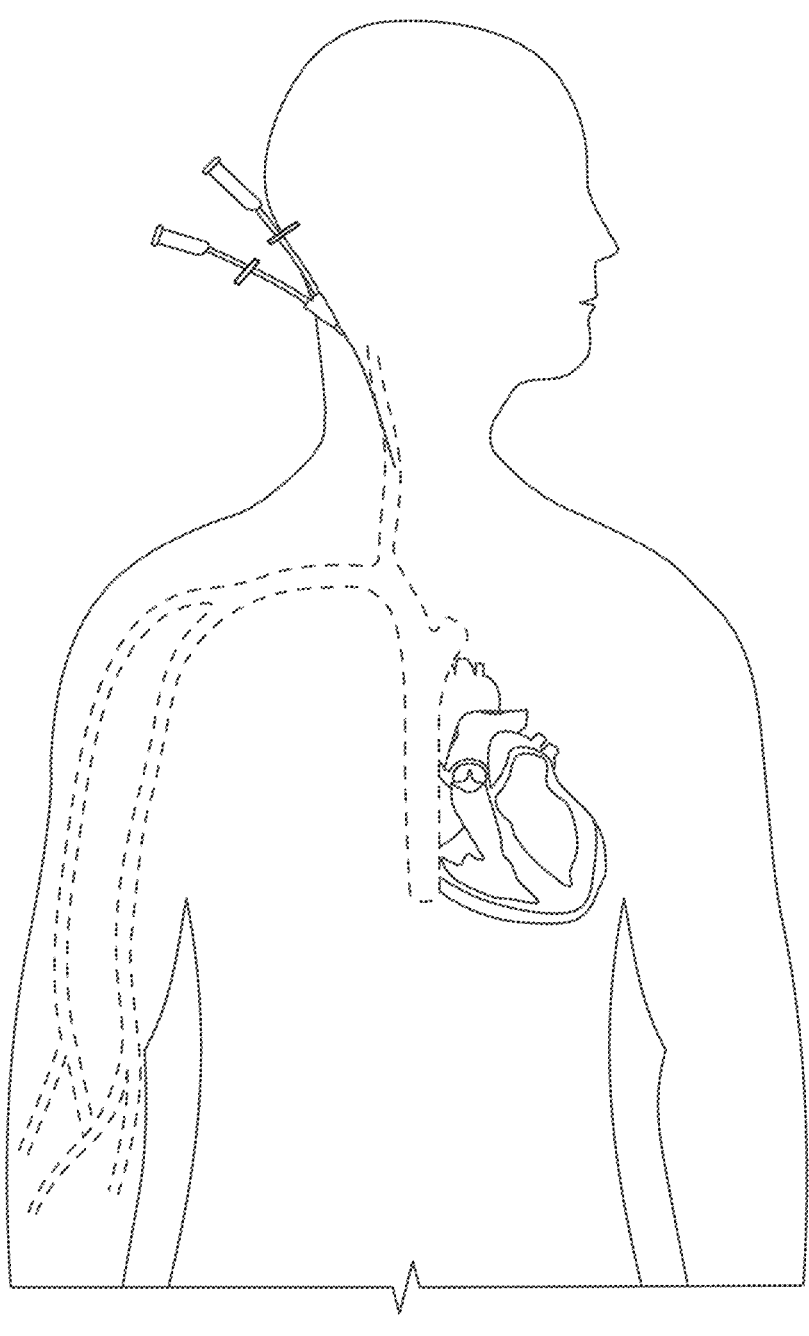
FIG. 2E shows an example of a delivery device being advanced toward the heart of a patient through an access point in the internal jugular vein.

FIGS. 2A and 2B show a section view of a heart, showing a guidewire E advancing from a catheter C toward the left atrial appendage LAA. As depicted, catheter C can enter the heart through the venous system via the femoral vein and advance to the left atrium through a transseptal puncture, though this is just one suitable method and path for accessing the LAA and other suitable methods and paths are possible. Further details regarding the delivery of catheter C to the ventricle, right atrium, left atrium, LAA, and other regions of the heart and adjacent veins are provided beginning with the description of FIG. 13A below.

Figure 3A:
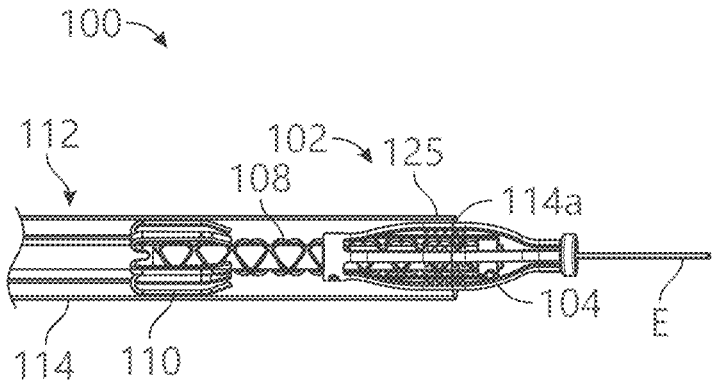
FIG. 3A shows an example of a treatment device housed in a catheter located in the right atrium, left atrium, or LAA.
Figure 3B:
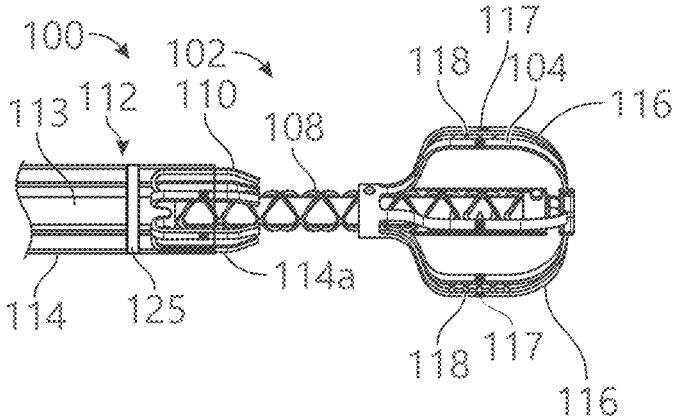
FIG. 3B shows an example of the treatment device at least partially deployed from the catheter and in an expanded state.

FIGS. 3A and 3B show an arrangement of a treatment device 100 for ablating myocardial tissue and occluding or closing the opening of the LAA. In any arrangements of the treatment device, including the arrangement of the treatment device 100, the system can have an implant device 102 having a contact member 104 (also referred to in any arrangements disclosed herein as a contact element, a first portion of the implant, or an expandable implant member), a securing member or securing element 110 (also referred to in any arrangements herein as a securing member or a second portion of the implant), and a retention element 108 (also referred to as a retention member). The implant device 102 can be configured to be advanced through a catheter 112 into the ventricle, right atrium, left atrium, or LAA. The arrangement of the implant device 102 shown in FIG. 3A is shown in a collapsed state and restrained within an outer sleeve 114 of the catheter 112. As shown, the implant device 102 can be advanced distally out of the catheter 112 past a distal end 114a of the outer sleeve 114 by advancing a portion of or member of the catheter, such as without limitation a core member 113 of the catheter 112, so that the contact member 104 of the implant device 102 can be deployed within the right atrium, left atrium, or LAA.

Alternatively, the catheter 112 having the implant device 102 therein can be advanced into a desired position within the ventricle, right atrium, left atrium, or LAA and, while holding the implant device 102 in a stationary axial position by maintaining the core member 113 of the catheter 112 in a stationary axial position, the outer sleeve 114 of the catheter 112 can be retracted or withdrawn so as to expose and/or unrestrain the contact member 104 of the implant device 102. In any arrangements disclosed herein, the contact member 104 can be self-expanding in a radial direction so that, when a restraint is removed from the contact member 104, the contact member 104 can expand automatically. In other arrangements, the contact member 104 can be mechanically expandable, such as by a balloon expander Alternatively, in any arrangements disclosed herein, the contact member can be configured to remain in a first state within the catheter, during the entire treatment procedure, and/or thereafter. For example and without limitation, in any arrangements disclosed herein, the contact member can be configured such that the contact member is deployed from the catheter and advanced into contact with a tissue surface of an inside wall of the heart, all without changing the state of the contact member.

In any arrangements disclosed herein, including the arrangement illustrated in FIG. 3B, the contact member 104 can have a plurality of arms or struts 116 that can extend along the longitudinal axis of contact member 104 and are each configured to self-expand in a radial direction when a restraint has been removed from an outside surface of the contact member 104. For example without limitation, any arrangements of the contact member disclosed herein can have six struts 116, or between six and ten struts, or from less than six to more than ten struts. In some examples, the struts can comprise a material selected from a group consisting of nitinol, cobalt chromium, stainless steel, titanium, and combinations hereof.

In one aspect, the size of the expanded contact member 104 can be any suitable size for positioning the contact member at an ablation site and performing ablation, as well as performing the occlusion or elimination of the AAF described herein. In some embodiments, the outer diameter of contact member 104, in a radial direction, can be between approximately 12 mm and 16 mm, or in some embodiments approximately 18 mm. In other embodiments, the outer diameter of contact member 104, in the radial direction, can be any other suitable size, including less than 12 mm or greater than 16 mm.

In another aspect, one or more electrodes 117 can be coupled to one or more of struts 116 or the outer edges of contact member 104 for ablating tissue. In some examples, electrodes 117 can comprise a material selected from stainless steel, cobalt chromium, gold, platinum, palladium, and alloys hereof. Electrodes 117 can be coupled to struts 116 using any suitable technique, including but not limited to soldering or welding the electrodes to the struts, using an adhesive to secure the electrodes to the struts, and/or pressure fitting the electrodes to the struts by passing a strut through an opening in an electrode body.

In one aspect, the electrodes can be configured to deliver electrical pulses for irreversible electroporation, including a peak voltage of at least 900 volts (V) and in some embodiment as much as 12000V. The contact member can further include an electrically insulative jacket (not depicted) disposed between each electrode 117 and its respective strut 116, thereby electrically isolating the electrode from the strut. Contact member 104 can also include a wire disposed inside each insulative jacket for electrically connecting each electrode 117, through the catheter 112, to an external power source (not depicted). In alternative embodiments, core member 113 or outer sleeve 114 of catheter 112 can comprise conductive elements for transferring electrical signals to and from electrodes 122 along catheter 112.

To perform an ablation, such as PFA, a medical professional can manipulate a delivery system to position contact member 104 within an atrium of the heart such that electrodes 117 engage cardiac tissue at a desired location or locations. Upon positioning contact member 104 so that electrodes 117 engage cardiac tissue, the medical professional can activate treatment device 100 such that electrical pulses are delivered by electrodes 117 to perform the ablation. In some embodiments, contact member 104 can be used to ablate tissue at a number of locations within or proximate the heart, including but not limited to the pulmonary vein ostia, the left atrial posterior wall, the left atrial roof, the mitral isthmus, the coronary sinus, or the right atrium or in the ventricle, such as but not limited to the inferior wall, anterior wall, lateral wall, epicardial surface, right ventricular outflow tract, left ventricular outflow tract, papillary muscles, septum, or substrate-based targets (e.g., scars). More details regarding the delivery system and how a medical professional can position contact member 104 at a desired location within the heart are described below, beginning at FIG. 13A.

In some examples, contact member 104 can be used to perform unipolar ablation by delivering biphasic or monophasic pulses between any of electrodes 117 and a body surface electrode affixed to a patient's skin, typically using adhesive patches (sometimes referred to as a grounding electrode or grounding pad). Alternatively, contact member 104 can be used to perform bipolar ablation by delivering biphasic or monophasic pulses between any pair of electrodes 117 or between any electrode 117 of contact member 104 and any electrode 122 of securing element 110 (further described below).

In other embodiments, contact member 104 itself can be energized and serve as an electrode. In some such embodiments, contact member 104 itself can be used to perform unipolar ablation in cooperation with a body surface electrode. In other embodiments, contact member 104 can be used to perform bipolar ablation in conjunction with an electrode 122 coupled to securing element 110 of treatment device 100 or in conjunction with securing element 110 in embodiments in which securing element 110 itself can be energized and serve as an electrode.

In further embodiments, and in addition to using electrodes 117 of contact member 104 for ablation, electrodes 117 can be utilized to monitor or record ECG signals by detecting and transmitting the electrical activity of a patient's heart. In such embodiments, electrodes 117 can be used to identify abnormal electrical signals within the heart, among other things. In other embodiments, electrodes 117 can be used to detect the location of the distal end of catheter 112 within a patient's heart vascular system, and create an electroanatomical map of patient's heart.

For example, the position of the distal end of catheter 112 in the patient's body can be calculated based on electromagnetic position sensor(s), e.g., sensor 125, which may be single-axis or triple-axis magnetic sensors, configured to detect magnetic field strength and orientation to determine the three-dimensional location and orientation of the catheter. In some embodiments a single magnetic location sensor 125 may be positioned at the distal tip of catheter 112, while in other embodiments, multiple sensors (not shown) may be spaced along the catheter shaft to improve location accuracy and track bending or deflection of the catheter. The magnetic location sensor(s) output signals when in the presence of a generated magnetic field. Location coordinates can additionally, or alternatively, be based on impedances and/or currents measured between electrodes 117 and one or more body surface electrodes. By tracking the location of electrical signals emitted from electrodes 117 relative to the body surface electrodes, the position of electrodes 117 within the patient's body can be determined. Such a determination is typically performed after a calibration process relating the impedances or currents to known locations of the distal end of catheter 112 has been performed.

Based on signals received from magnetic sensor 125, electrodes 117 and/or the body surface electrodes, an electroanatomical map of the patient's vascular system can be generated that also shows the location of the distal end 36 of catheter 112. During a procedure, the map can be presented to a medical professional on a display, and data representing the electroanatomical map can be stored for later use.

Figure 4:
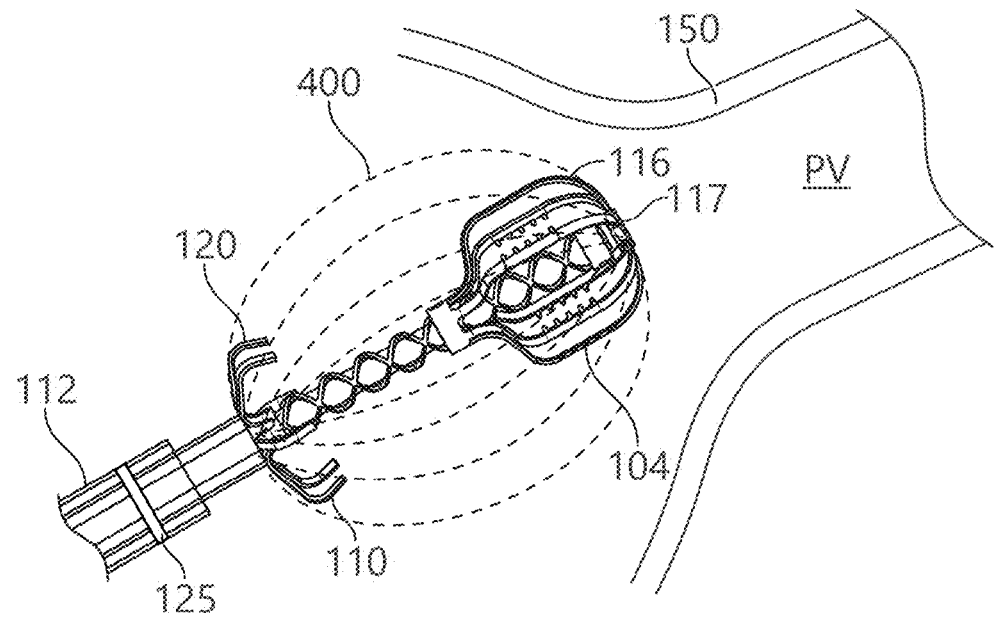
FIG. 4 shows an example of the treatment device fully deployed from the catheter and in an expanded state.

FIG. 4 illustrates implant device 102 after contact member 104 and securing element 110 are deployed from catheter 112 and one or both of contact member 104 and securing element 110 can be used to ablate tissue at any suitable location within or proximate the heart, including but not limited to the pulmonary vein ostia, the left atrial posterior wall, the left atrial roof, the mitral isthmus, the coronary sinus, or the right atrium or in the ventricle, such as but not limited to the inferior wall, anterior wall, lateral wall, epicardial surface, right ventricular outflow tract, left ventricular outflow tract, papillary muscles, septum, or substrate-based targets (e.g., scars). When deployed in its fully expanded state, the implant's electrodes can be positioned to ensure effective contact with cardiac tissue.

In some embodiments, and as just one example, implant device 102 may be configured for focal ablation, enabling precise delivery of ablative energy to targeted cardiac tissue. Implant device 102 can include at least one distal electrode 117 positioned at or near the tip or distal end of contact member 104, which in some embodiments may be used for unipolar ablation in conjunction with a body surface electrode placed on the patient's skin. In this configuration, high-frequency energy can be delivered through distal electrode 117, allowing focused tissue ablation at the implant's contact site. In an alternative embodiment, contact member 104 itself (i.e., as a whole) can be energized and serve as an electrode.

Alternatively, two or more electrodes may be positioned on implant device 102 to enable bipolar ablation, where energy is passed between the electrodes, creating a localized and controlled ablation zone. For example, a proximal electrode 122 can be positioned at a proximal or base end of securing element 110. In such embodiments, energy can be delivered from one of distal electrode 117 or proximal electrode 122 to the other to perform bipolar ablation. In another embodiment, each of contact member 104 and securing element 110 themselves (i.e., as respective wholes) can serve as an electrode configured for transmitting energy from one to another. In either case, the transmission of energy between contact member 104 and securing element 110 can generate a bipolar ablative energy field 400 as, for example, depicted by the dotted lines in FIG. 4.

In another aspect, the placement of electrodes can vary depending on procedural needs. In some embodiments, focal ablation can be performed while implant device 102 remains at least partially within the sheath and in a collapsed state, such as when contact member 104 is fully deployed from catheter 112 but securing element 110 remains collapsed within the catheter (as depicted in FIG. 3B). The sheath may also include an electrically insulative liner to prevent unintended energy transmission. In such embodiments, unipolar ablation can be performed using an electrode 117 of contact member 104 in conjunction with a body surface electrode placed on the patient's skin. Alternatively, bipolar ablation can be performed using a pair of spaced apart electrodes 117, both of which can be positioned on contact member 104 such as, for example, the arrangement depicted in FIG. 3B. In other embodiments, the electrodes may be activated for focal ablation after the implant has been fully expanded. Regardless of whether contact member 104 itself serves as an electrode or one or more discrete electrodes are positioned on contact member 104, and similarly whether securing element 110 itself serves as an electrode or one or more discrete electrodes are positioned on securing element 110, and regardless of whether implant device 102 is to be used to perform unipolar ablation or bipolar ablation, whether as part of a focal ablation or another suitable ablation technique, implant device 102 can deliver the desired ablative energy to cardiac tissue with which it is in contact with before transitioning to its use for LAA elimination or closure.

As just one example of such configurations, and as depicted in FIG. 4, implant device 102 can be used to perform a pulmonary vein isolation procedure before transitioning to its use for LAA elimination or closure. Pulmonary vein isolation is typically used to treat atrial fibrillation (AF), and the goal is to electrically isolate the pulmonary veins which are frequently the source of ectopic electrical signals that can trigger AF. This can be accomplished, in some examples, by delivering ablative energy to create a circumferential lesion around the pulmonary vein ostia, isolating the pulmonary vein from the rest of the left atrium.

As depicted in FIG. 4, contact member 104 and securing element 110 can be fully deployed from catheter 112 at a location at or near the ostia 150 of a pulmonary vein. In some examples, each of contact member 104 and securing element 110 themselves can serve as an electrode. In other examples, one or both of contact member 104 and securing element 110 can comprise one or more electrodes such as, for example, a distal electrode 117 located on contact member 104 and a proximal electrode 122 located on securing element 110. In either case, contact member 104 and securing element 110 can be used in conjunction with one another to perform bipolar ablation as part of a pulmonary vein isolation procedure.

In one aspect, contact member 104 can be advanced into ostia 150 to make contact with the surrounding tissue. In some embodiments, the outer diameter of contact member 104 can be substantially the same as the inner diameter of ostia 150. In such examples, pairs of electrodes positioned on contact member 104 can be used (either simultaneously or sequentially) to create a circumferential lesion within ostia 150 and/or the pulmonary vein without relocating contact member 104 between pulses. In other embodiments, the outer diameter of contact member 104 can be smaller than the inner diameter of ostia 150 such that the entire outer circumference of contact member 104 cannot be in contact with the interior of the pulmonary vein or ostia 150 along its entire interior circumference. In such examples, pairs of electrodes positioned on contact member 104 and in contact with tissue within ostia 150 or the pulmonary vein can be used to ablate a portion of a desired circumferential lesion before contact member 140 is relocated to another position within the ostia or pulmonary vein and another ablation is performed. This process can continue, in some examples, until the plurality of ablations form a circumferential lesion around the pulmonary vein and the isolation procedure is completed.

In alternative embodiments, securing element 110 (and/or any electrodes positioned thereon) can be used in conjunction with any electrodes of contact member 104 to similarly perform bipolar ablations. For example, both contact member 104 and securing element 110 can be positioned in contact with ostia 150 or the pulmonary vein. Where implant device 102 is sized such that both contact member 104 and securing element 110 are in contact with tissue around the entire interior circumference of the pulmonary vein or ostia 150, the electrodes can be used to create a circumferential lesion around the pulmonary vein without relocating implant device 102 between ablation pulses. Alternatively, where contact member 104 and securing element 110 are smaller in circumference than the pulmonary vein, they can be used in conjunction with one another to ablate a first portion of the desired circumferential lesion before being relocated one or more times to ablate other portions of the desired circumferential lesion and the isolation procedure is completed.

In still further embodiments, either of contact member 104 or securing element 110 can be used in conjunction with a body surface electrode placed on the patient's skin to perform the isolation procedure using unipolar ablation. Again, depending on the relative size of contact member 104 or securing element 110 compared to ostia 150 or the interior circumference of the pulmonary vein, such a unipolar isolation procedure can be performed while maintaining implant device 102 in one location, or a number of ablations can be performed sequentially, each directed at a portion of the desired circumferential lesion as the implant device is relocated around the interior circumference of the pulmonary vein or ostia until the procedure is complete.

Figure 5:
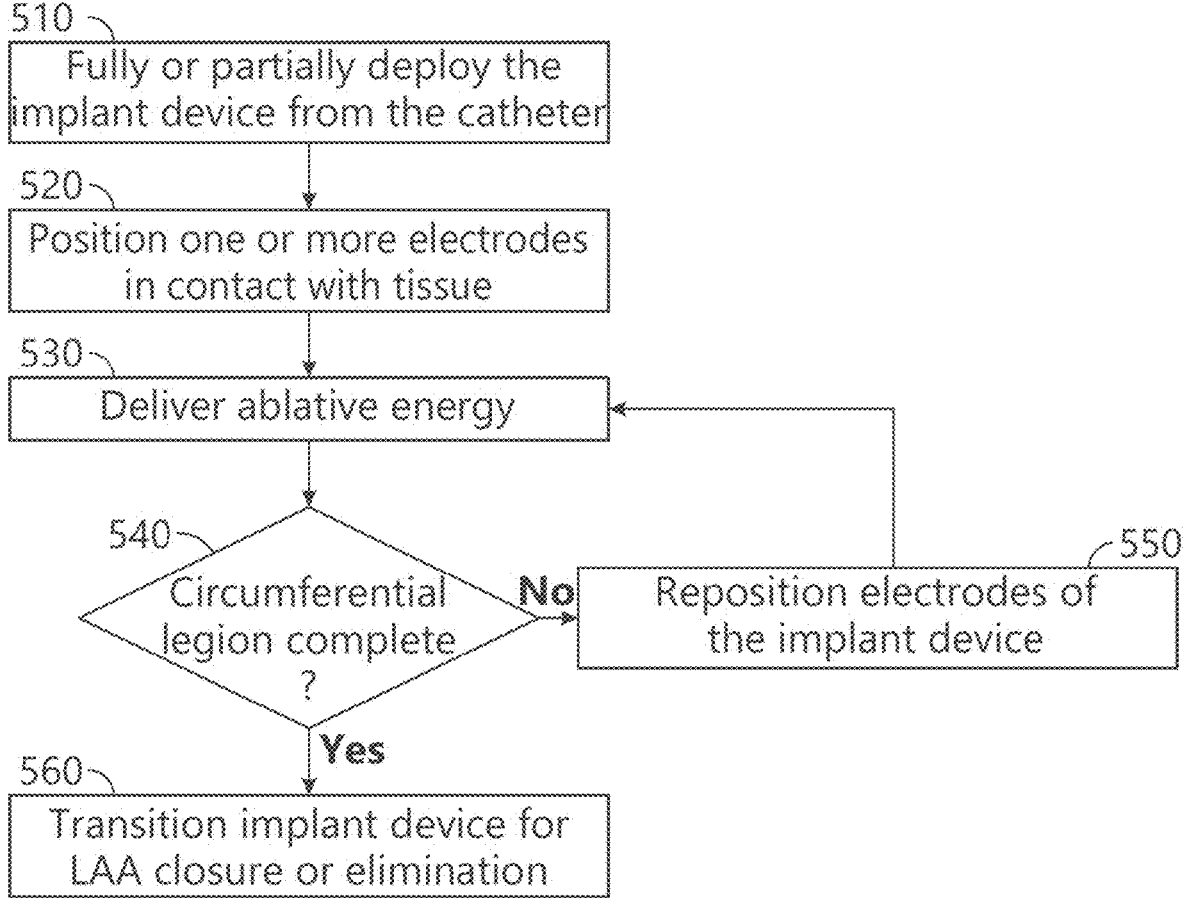
FIG. 5 shows a flowchart describing an ablation procedure at a location distinct from the ostium or interior of the LAA.

FIG. 5 depicts a flowchart for performing a pulmonary vein isolation procedure using implant device 102. At step 510, implant device 102 is either fully or partially deployed at a location at or near an ostia of a pulmonary vein. Regardless of whether unipolar or bipolar ablation is to be used, at step 520, one or more electrodes are positioned in contact with the pulmonary vein or ostia tissue. At step 530, ablative energy can then be delivered to the one or more electrodes for creating a circumferential lesion around the interior of the pulmonary vein or ostia, thereby isolating the pulmonary vein.

At step 540, it is determined whether the circumferential lesion is complete. In some embodiments, where the outer circumference of the deployed implant device 102 is substantially the same as the interior circumference of the pulmonary vein, the circumferential lesion can be formed without needing to relocate implant device 102 during the procedure. In such embodiments, the process can advance to step 560. In other embodiments, where the deployed implant device 102 is sized such that it cannot be in contact with the pulmonary vein around its entire interior circumference, implant device 102 can be repositioned at step 550 such that it is in contact with another portion of the pulmonary vein at a location making up another part of a desired circumferential lesion. This process can be repeated as many times as necessary to create the desired circumferential lesion needed to isolate the pulmonary vein.

At step 560, once the circumferential lesion and the isolation procedure are complete, the implant device can be repositioned from the pulmonary vein to a location at or near the LAA where it can be used to perform a LAA elimination or closure procedure, as described in more detail below. The method described relative to FIG. 5 for performing pulmonary vein isolation utilizing device and system herein is intended solely as an exemplary and explanatory illustration. It should not be construed as a limitation on the claims appended hereto. The devices encompassed by these claims may be employed for a variety of other cardiac ablation procedures. Such procedures may include, but are not limited to, ablation at one or more sites selected from the left atrial posterior wall, left atrial roof, mitral isthmus, coronary sinus, right atrium, and various ventricular regions.

Figure 6A:
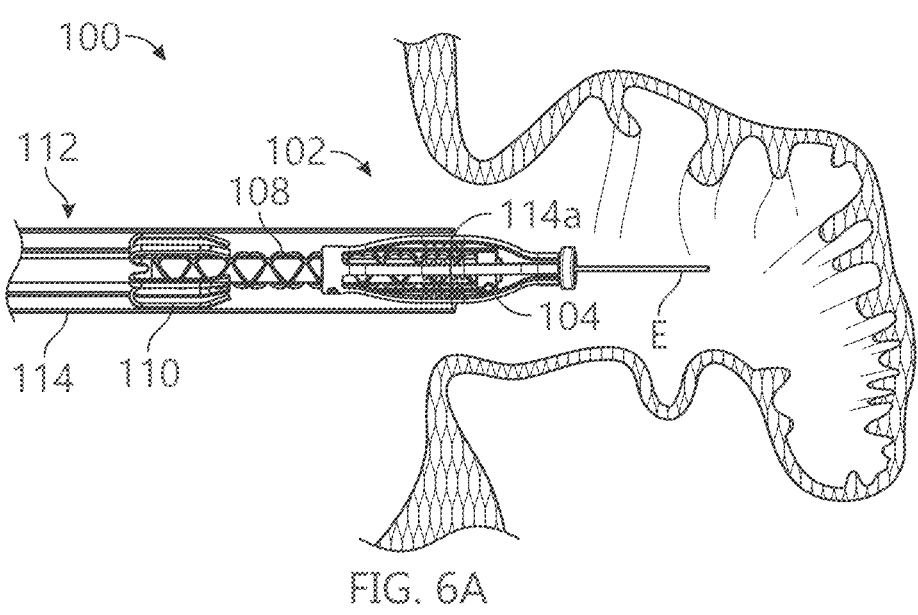
FIG. 6A shows an arrangement of the treatment device having an implant device being advanced through a catheter into the LAA, the implant device being in a collapsed state and restrained within an outer tube of the catheter.

After performing any ablation, ECG detection, or mapping procedures, implant device can be advanced to the LAA or just outside the ostium or opening of the LAA. FIG. 6A shows an arrangement of a treatment device 100 located just outside or partially within the LAA but still in a collapsed state and restrained within an outer sleeve 114 of the catheter 112. This may be the case, for example, where no ablation has been performed using electrodes 117 of contact member 104. In such embodiments, contact member 104 can be deployed from outer sleeve 114 in similar manners as those described above with respect to FIGS. 3A and 3B so as to expand and be positioned against inside surface or wall of the LAA. In alternative embodiments, where ablation is performed with either a fully deployed implant device 102 (i.e., both contact member 104 and securing element 110 are deployed from catheter 112) or a partially deployed implant device 102 (i.e., contact member 104 can be deployed while securing element 110 remains collapsed within catheter 112), implant device 102 may appear as depicted in FIG. 3B or FIG. 4, respectively, at the time that it is advanced to the LAA or just outside the ostium or opening of the LAA.

Figure 6B:
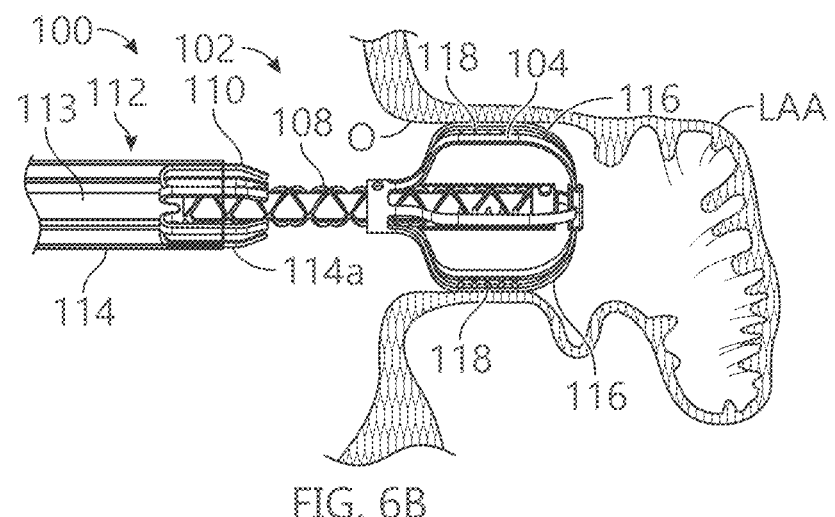
FIG. 6B shows the arrangement of the treatment device of FIG. 3A, showing the contact member being expanded within the LAA.

FIG. 6B illustrates the contact member 104 after it has been expanded and advanced against an inside wall of the LAA distal to the ostium of the LAA. In some embodiments, contact member 104 can be expanded elsewhere in the heart (i.e., at a location distinct from the ostium or interior of the LAA, such as a location within the right atrium or left atrium) for performing ablation prior to being repositioned near the LAA. In other embodiments, contact member 104 can be deployed from catheter 112 just outside or partially within the LAA, and advanced into contact with a tissue surface of an inside wall of the LAA. Alternatively, in any arrangements disclosed herein, contact member 104 can be advanced into the pericardial space around an outside of the LAA to engage an outside surface of the LAA.

In any arrangements disclosed herein, after contact member 104 is advanced into contact with a wall of the LAA or the ostium of the LAA, contact member 104 can be configured to rotate and twist the LAA so as to cause a neck or a portion of the LAA adjacent to the opening of the LAA to constrict and substantially or fully close about an outside surface of a portion of the implant device, thereby causing the opening of the LAA to be closed or eliminated.

Further, in any arrangements, the contact member 104 can have a plurality of teeth, cleats, barbs, nubs, texture, studs, anchors or other tissue engaging features 118 or other similar features configured to penetrate or engage the tissue of the LAA that are configured to penetrate into a tissue within the LAA when the contact member 104 is advanced against the tissue of the LAA and/or when the contact member 104 is rotated or twisted within the LAA. Note that teeth, cleats, barbs, nubs, texture, studs, anchors and other tissue engaging features or features configured to grip or engage the tissue when torque is applied to the expanded contact member will be collectively referred to herein as tissue anchors, which use of this term is meant to describe and include any of the foregoing features individually and/or any combination of these features.

The tissue anchors 118 can be integrally formed with the struts, on the struts, added to the struts, or otherwise coupled with or supported by the struts. The tissue anchors 118 can be circumferentially facing (as shown), can be radially facing so as to penetrate or engage the tissue at an orthogonal angle relative to the tissue surface of the LAA, at an angle relative to the line that is tangential to the outer surface of the contact member 104, or otherwise. In some embodiments, circumferentially facing tissue anchors 118, or tissue anchors extending at a relatively small angle relative to the line that is tangential to the outer surface of the contact member 104 (e.g., fifteen degrees) are well suited for procedures that use the contact member 104 (or one or more electrodes positioned thereon) for delivering ablation prior to transitioning the implant device 102 for closing or eliminating the LAA. For example, where tissue anchors 118 extend circumferentially or at a small angle relative to the tangent, rather than extending orthogonally from the outer surface of contact member 104, the outer surface of contact member 104 can be positioned against tissue at any suitable location at or near the patient's heart without risk of tearing, perforating, or otherwise damaging the tissue. In such arrangements, tissue anchors 118 only engage tissue that is in contact with the outer wall of contact member 104 when contact member 104 is rotated in the direction that the tissue anchors 118 extend.

In some arrangements, each strut 116 can support a plurality of tapered tissue anchors facing in a circumferential direction, as illustrated in FIG. 6B. All of the tissue anchors can face in a similar orientation relative to each of the struts 116, such as in the circumferential direction relative to each strut 116. In the illustrated arrangement, each strut 116 has five tissue anchors 118. In this arrangement, when the contact member 104 is rotated in a first direction (indicated by arrow A1 in FIG. 6C, which can be in the clockwise or the counterclockwise direction), one or more or all of the struts 116 and one or more or all of the tissue anchors 118 can engage the tissue of the LAA and cause the LAA to twist or rotate in the first direction A1. The twisting or rotation of the LAA in the first direction from a first rotational position to a second rotational position results in the opening or ostium O of the LAA constricting in a radial direction (represented or identified by arrows A2 in FIG. 6C) so that the opening O of the LAA is caused to move or constrict around an outside surface of a proximal portion 104a of the contact member 104. An operator can twist or rotate the contact member 104 by twisting or rotating the core member 113 of the catheter 112. The tightening or constriction of the opening O of the LAA around an outside surface of the proximal portion 104a of the contact member 104 or other portion of the implant device can result in the occlusion, or substantial occlusion, or substantial closing off of the interior portion of the LAA from the remaining chambers within the heart, thereby substantially reducing the health risks associated with an open LAA.

In some arrangements, as in the illustrated arrangement, the securing element 110 can be maintained in a collapsed or first state such as by being restrained by the outer sleeve 114 of the catheter 112 while the contact member 104 is being deployed and rotated to prevent the securing element 110 from contacting tissue within the heart and potentially lacerating or otherwise damaging such tissue. A catheter tube member 115 (e.g., an intermediary sleeve or tube) can be coupled with the securing element 110 and can be used to manipulate and control a position and/or an orientation of the securing element 110, including holding a proximal end portion 110' of the securing element in a fixed axial position while a distally directed force is exerted on the contact member 104 to maintain the retention element in the first, extended state. In any implant device arrangements disclosed herein, the securing element (including, for example and without limitation, securing element 110) can be keyed, indexed, or otherwise rotationally fixed to the contact member (including, for example and without limitation, contact member 104) so that the securing element cannot rotate relative to the contact member and the contact member cannot rotate relative to the securing element. In this configuration, the securing element can prevent or substantially prevent or inhibit the contact member and the LAA from rotating back toward the first rotational position.

Figure 6C:
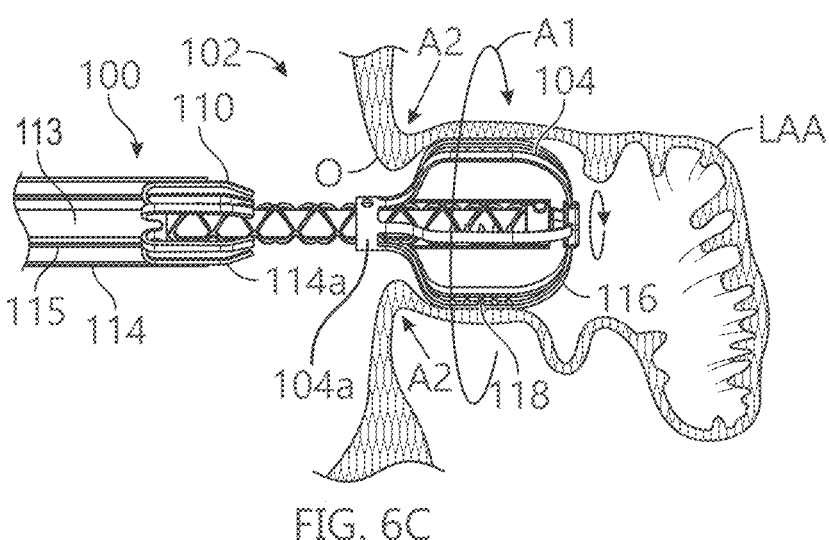
FIG. 6C shows the arrangement of the treatment device of FIG. 3A, showing the contact member being rotated to twist the LAA and cause a neck or opening of the LAA to constrict around a portion of the implant device.
Figure 6D:
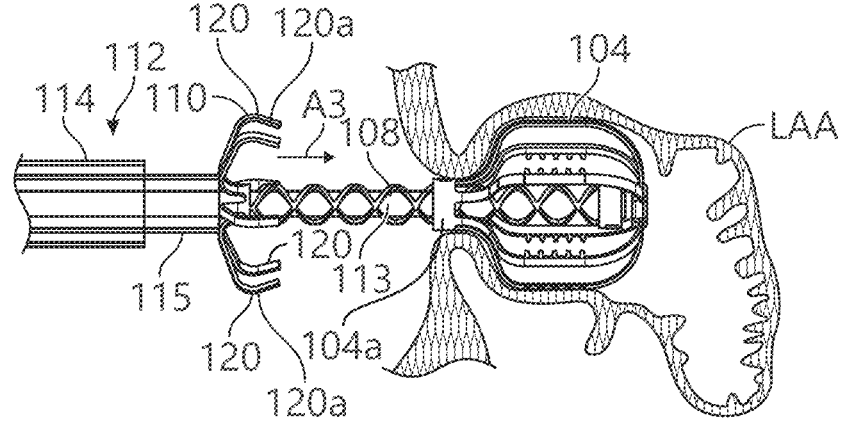
FIG. 6D shows the arrangement of the treatment device of FIG. 3A, showing the securing element of the arrangement of the implant device being advanced toward the contact member of the implant device.
Figure 6E:
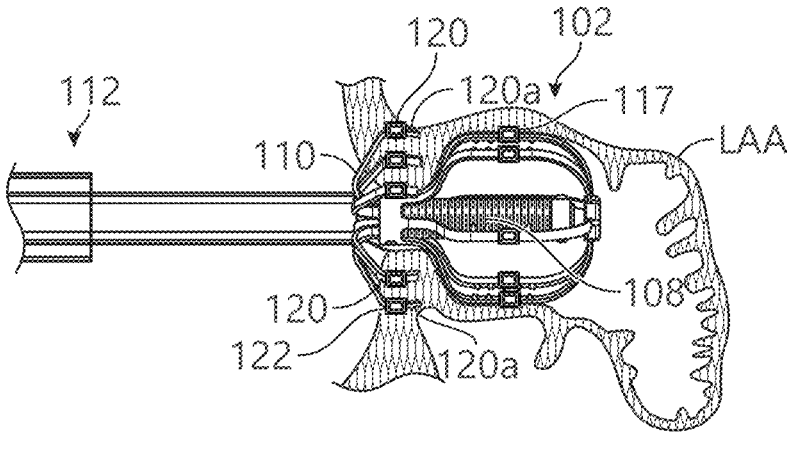
FIG. 6E shows the securing element of the treatment device of FIG. 3A engaged with the patient's tissue that has constricted as a result of the twisting of the LAA.

With reference to FIG. 6D, with the contact member 104 having been rotated to the second rotational position and maintained in the second rotational position such that the opening O of the LAA remains constricted around a proximal portion 104*a* of the contact member 104 or other portion of the implant device and the LAA is generally occluded from the remainder of the heart chambers, the catheter tube member 115 can then be advanced in a distal direction (represented by arrow A3 as shown in FIG. 6D) or the outer sleeve 114 can be withdrawn in a proximal direction so that the securing element of 110 can be exposed so that it can self-expand from a first, collapsed state (as shown in FIG. 6C) to a second, expanded or open state (as shown in FIG. 6D). In the second state, a plurality of struts or members 120 of the securing element 110 can expand in a generally radial direction so as to open up to a larger overall diameter or profile. Additionally, because each of the one or more members 120 of the securing element 110 can have end portions 120*a* that extend in a generally distal axial direction (but can be slightly angled inwardly), as the securing element 110 is advanced in the axial direction, the distal end portions 120*a* of each of the one or more members 120 can penetrate into and/or engage with a tissue portion of the heart, as shown in FIG. 6E. The tissue portion that the one or more members 120 can penetrate into or engage with can include portions of the tissue comprising the left atrium and/or portions of the tissue comprising the LAA. As mentioned above, the contact member 104 can be held in generally a stationary axial position using the core member 113 while the securing element 110 is advanced distally toward the contact member 104. The retention element 108 can thereafter be unrestrained so that it can maintain the securing element 110 in the second rotational position wherein the securing element 110 is engaged with the tissue of the heart, as shown in FIG. 6E. In some arrangements, the securing element can be biased toward a smaller size in the axial direction, such as with a spring member or similar. For example, the retention element 108 can be formed by laser cutting openings within a cylindrical tube, such as a hypo tube made of an elastic material, such as Nitinol.

In another aspect, one or more electrodes 122 can be coupled to one or more of the struts 120 of the securing element 110. Electrodes 122 can be coupled to struts 120, for example, using any of the techniques described above for coupling electrodes 117 to struts 116 of contact member 104, or any other suitable technique. In some examples, electrodes 122 can comprise a material selected from stainless steel, cobalt chromium, gold, platinum, palladium, iridium, titanium, silver, tungsten, ruthenium, ruthenium oxide, carbon-based materials (such as graphite, carbon nanotubes, or diamond-like carbon), conductive polymers (such as PEDOT) and alloys hereof. The electrodes can be configured to deliver electrical pulses for irreversible electroporation, including a peak voltage of at least 900 volts (V) or as much as 12000V or more. The securing element can further include an electrically insulative jacket (not depicted) disposed between each electrode 122 and its respective strut 120, thereby electrically isolating the electrode from the strut. Securing element 110 can also include a wire disposed inside each insulative jacket for electrically connecting each electrode 122, through the catheter 112, to an external power source, such as a generator, i.e., an RF or PFA generator (not depicted). In alternative embodiments, core member 113 or outer sleeve 114 of catheter 112 can comprise conductive elements for transferring electrical signals to and from electrodes 122 along catheter 112.

In any arrangements of the methods and devices disclosed herein, electrodes 122 of securing element 110 can be used to perform ablations similar to those described above with respect to electrodes 117 of contact member 104. For example, upon positioning securing element 110 so that it is engaged with tissue proximate the LAA as depicted in FIG. 6E, electrical pulses can be delivered by electrodes 122 to perform ablation. In other embodiments, securing element 110 can be expanded prior to the advancing of contact member 104 into (or partially into) the LAA and electrodes 122 can be used to perform ablation in a location distinct from the LAA, such as the right atrium or anywhere in the left atrium.

In one aspect, electrodes 122 of securing element 110 can be used to perform unipolar ablation by delivering biphasic or monophasic pulses between any of electrodes 122 and a body surface electrode affixed to a patient's skin or a grounding electrode. Alternatively, securing element 110 can be used to perform bipolar ablation by delivering biphasic pulses between any pair of electrodes 122 or between any electrode 122 of securing element 110 and any electrode 117 of contact member 104.

Alternatively, securing element 110 itself can be energized and serve as an electrode. In some such embodiments, securing element 110 can be used to perform unipolar ablation in cooperation with a body surface electrode. In other embodiments, securing element 110 can be used to perform bipolar ablation in conjunction with an electrode 117 of contact member 104 or in conjunction with contact member 104 in embodiments in which contact member 104 itself can be energized and serve as an electrode.

Figure 6F:
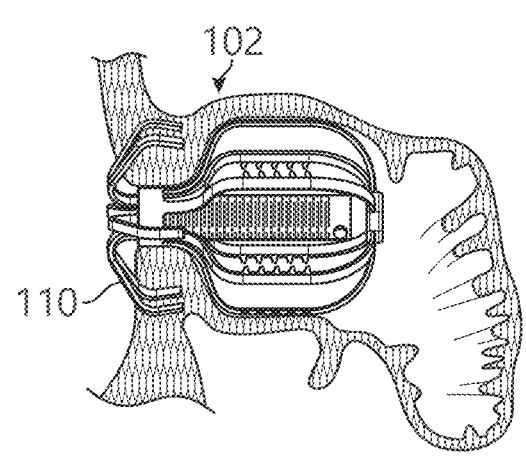
FIG. 6F shows the implant device of FIG. 3A disengaged and removed from the catheter.

With reference to FIG. 6F, after securing element 110 is engaged with the tissue of the heart, the implant device 102 can be disengaged from the catheter 112 and the catheter 112 can be retracted and removed from the patient's body. With the securing element 110 engaged with the patient's tissue, as illustrated in FIG. 6F, the LAA is prevented or, at least, inhibited or biased from rotating to the first rotational position, which is the untwisted or relaxed position. In this configuration, the implant device 102 can secure and maintain the LAA in a substantially or completely occluded or substantially or completely closed state.

Figure 6G:
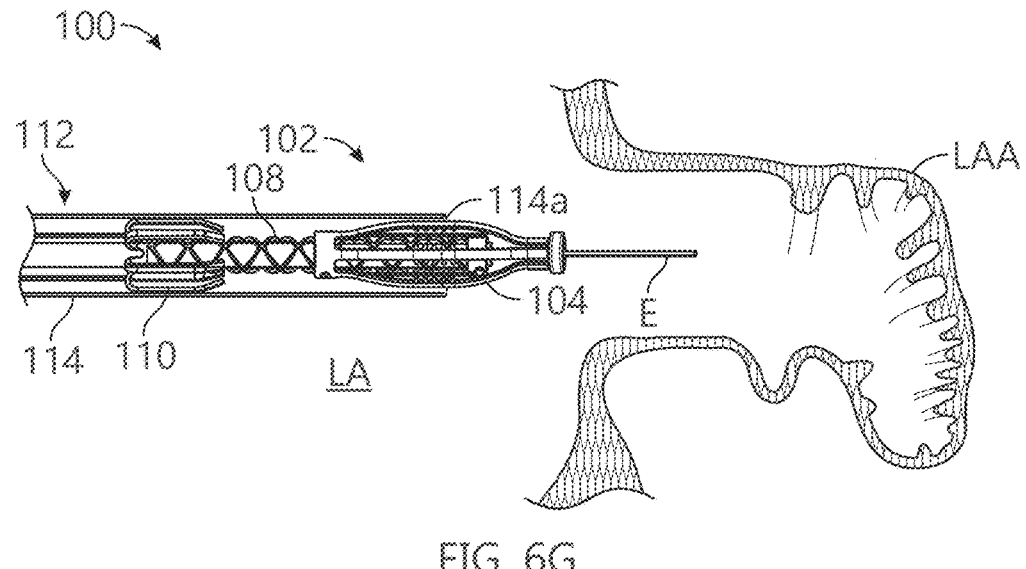
FIG. 6G shows the arrangement of treatment device of FIG. 3A advanced to the left atrium (LA), the implant device being in a collapsed state and restrained within an outer tube of the catheter.
Figure 6H:
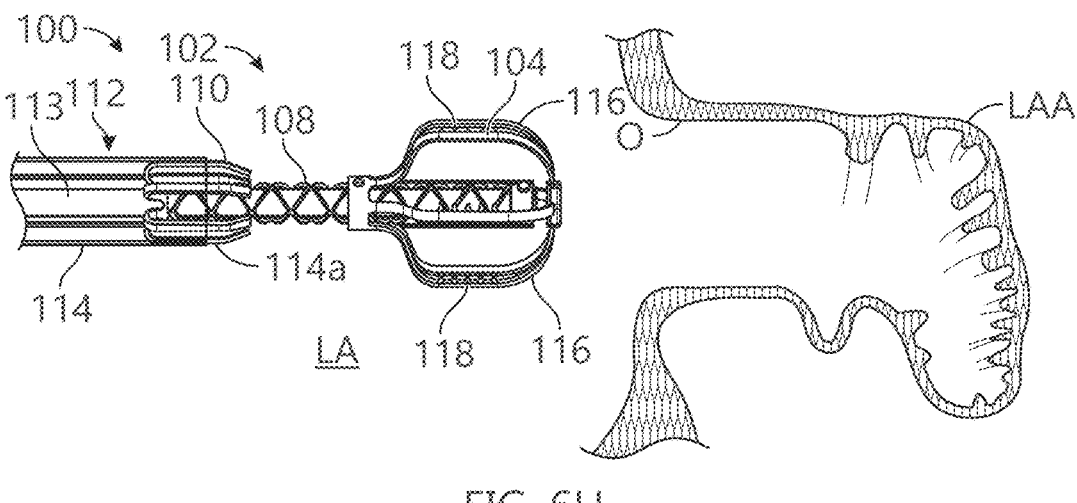
FIG. 6H shows the arrangement of the treatment device of FIG. 3A, showing the contact member being expanded within the LA before being advanced into the LAA.
Figure 6I:
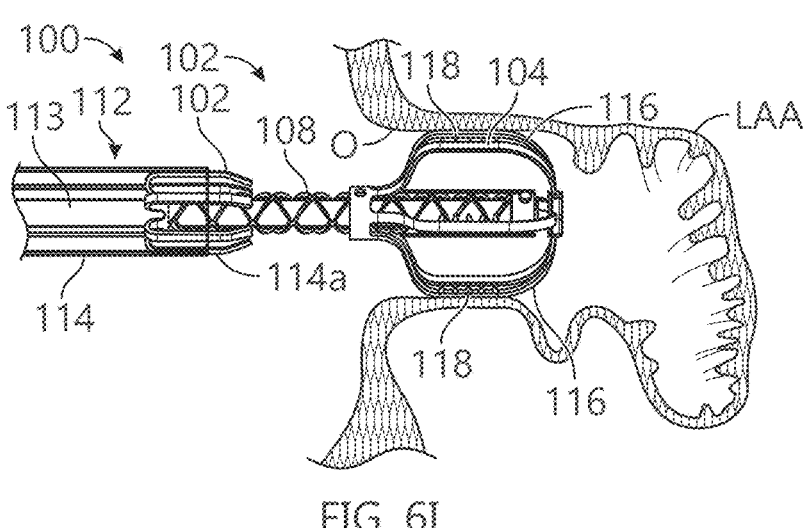
FIG. 6I shows the arrangement of the treatment device of FIG. 3A, showing the contact member being advanced into the LAA after the contact member has been expanded.
Figure 6J:
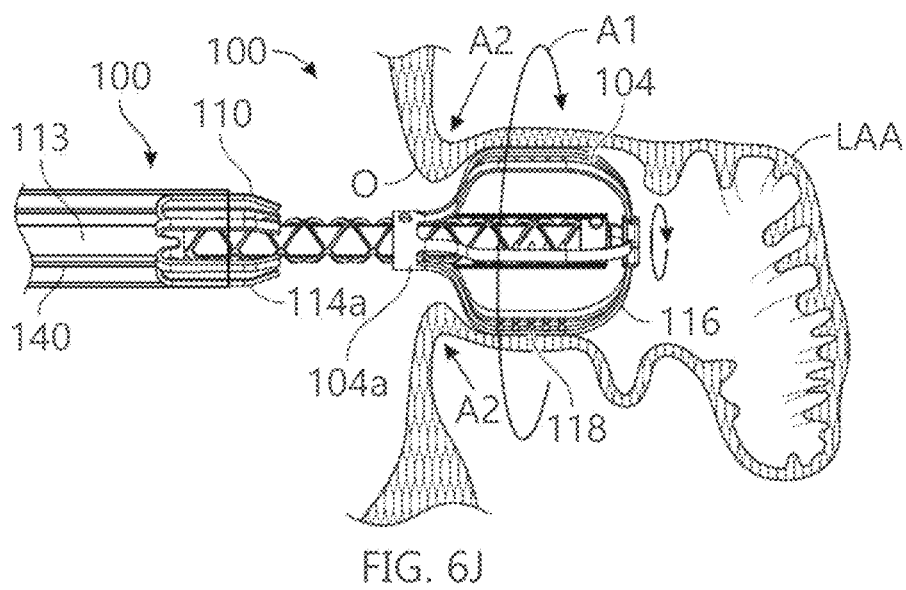
FIG. 6J shows the arrangement of the treatment device of FIG. 3A, showing the contact member being rotated to twist the LAA and cause a neck or opening of the LAA to constrict around a portion of the implant device.

Note that, in any arrangements of the methods and devices disclosed herein, including without limitation any of the methods of treating an LAA, the contact member can be partially or completely expanded in the left atrium (LA) before being advanced into the LAA. For example and without limitation, FIG. 6G shows the arrangement of treatment device 100 of FIG. 6A advanced the left atrium (LA), the implant device 102 being in a collapsed state and restrained within an outer sleeve (e.g., a tube or sheath) of the catheter. FIG. 6H shows the contact member 104 being partially or completely expanded (or partially or completely moved to the second state) within the LA before being advanced into the LAA. As shown in FIG. 6I, the contact member 104 and other components of the treatment device 100 can be advanced into the LAA when the contact member is in an expanded or second state, or when the contact member is partially in an expanded state or is between the first state and the second state. As shown in FIG. 6J, the contact member can be rotated to twist the LAA and cause a neck or opening of the LAA to constrict around a portion of the implant device, just as described above. Other steps to complete the treatment can be as described above and in other methods disclosed herein. Note that, as mentioned above, any of the treatment device arrangements disclosed herein can be configured so that the contact member can be partially or completely expanded in the LA before the contact member is advanced into the LAA. Similarly, in any of the arrangements of the methods disclosed herein (for example and without limitation, the arrangements of treating and/or occluding the LAA), the contact member can be partially or completely expanded in the LA before the contact member is advanced into the LAA. In certain arrangements, the contact member is not further expanded once positioned within the LAA and, in certain arrangements, the contact member can be further expanded or constricted once positioned within the LAA. In certain arrangements, the contact member could be constricted in the LA before entering the LAA and then could remain in a constricted position within the LAA or could be further expanded or constricted once positioned within the LAA.

As noted above, the contact member can be rotated to twist the LAA so as to cause a neck or a portion of the LAA adjacent to the opening of the LAA to constrict and substantially or fully close about an outside surface of a portion of the implant device, thereby causing the opening of the LAA to be occluded. In the illustrated arrangement, the contact member 104 can be rotated about its longitudinal axis to cause the twisting of the LAA. In certain arrangements, the longitudinal axis that the contact member is rotated about can correspond to or be closely aligned with an insertion axis of the securing element 110 as it is advanced towards the contact member 104. Additionally, any of the arrangements of the methods and devices disclosed herein can be configured such that the implant or contact member can be advanced from the delivery catheter and engage a wall of the LAA without the implant or contact member completely or partially expanding, changing size, changing shape, or moving to or toward a second state. For example, in some arrangements, the implant or contact member can be configured to engage and, upon rotation of the implant or contact member, rotate the LAA without the implant or contact member completely or partially expanding, changing size, changing shape, or moving to or toward a second state.

Figure 6K:
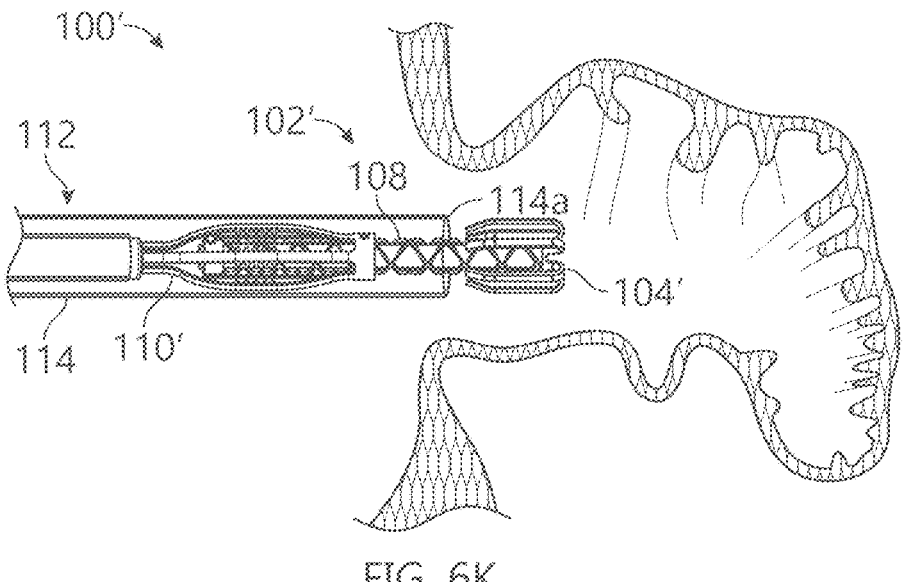
FIG. 6K shows another arrangement of treatment device having an implant device being advanced through a catheter into the LAA, the implant device being in a collapsed state and restrained within an outer tube of the catheter.
Figure 6L:
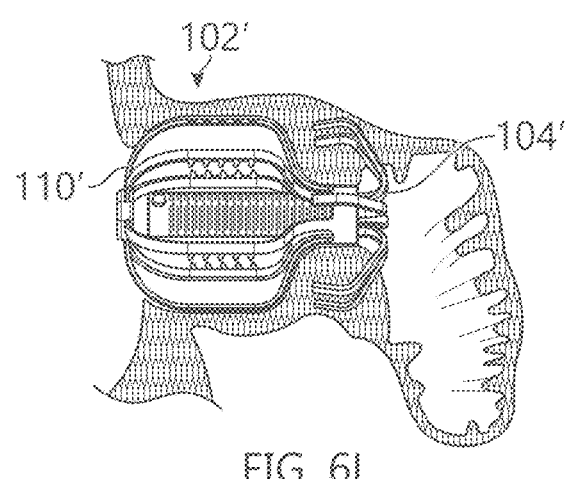
FIG. 6L shows the arrangement of the implant device of FIG. 3K engaged with the patient's tissue that has constricted as a result of the twisting of the LAA.

FIG. 6K shows another arrangement of treatment device 100' having an implant device 102' being advanced through a catheter into the LAA, the implant device 102' being in a collapsed state and restrained within an outer sleeve 114 of the catheter. FIG. 6L shows the arrangement of the implant device 102' of FIG. 6K engaged with the patient's tissue that has constricted as a result of the twisting of the LAA. In any arrangements, the implant device 102' can have a contact member 104', a securing element 110', and a retention element 108' extending between the contact member 104' and the securing element 110'. In some arrangements, the implant device 102' can be flipped as compared to the implant device 102 described above.

In some arrangements, the contact member 104' can be configured to treat the LAA the same as any other arrangements of the contact members disclosed herein. For example and without limitation, the contact member 104' can be configured to engage a tissue portion inside the LAA and twist the LAA so as to cause a portion of tissue of the LAA to constrict inwardly, just as other arrangements of the contact members disclosed herein. In the illustrated arrangement, the contact member 104' can have the same or a similar structure, functionality, components, and/or other details as any of the arrangements of the securing elements disclosed herein, for example and without limitation, the arrangements of the securing elements 110 disclosed herein, while being configured for engaging the tissue inside the LAA and twisting the LAA to constrict and/or occlude the ostium of the LAA.

Further, in some arrangements, the securing element 110' can be configured to treat the LAA the same as any other arrangements of the securing elements disclosed herein. For example and without limitation, the securing element 110' can be configured to engage the tissue that has constricted as a result of the twisting of the LAA so as to inhibit the constricted tissue from untwisting and/or so as to inhibit the constricted opening of the LAA from expanding. In the illustrated arrangement, the securing element 110' can have the same or a similar structure and functionality as any of the arrangements of the contact members disclosed herein, for example and without limitation, the arrangements of the contact members 104 disclosed herein.

In other arrangements, the implant device 110' can have a contact member that is similar to the arrangements of the contact member 104 disclosed herein or other arrangements of contact members disclosed herein (with the exception of the arrangements of the contact member 104') along with the arrangements of the securing element 110' disclosed herein, or a securing element that has a structure that is the same or similar to any other arrangements of contact members disclosed herein (with the exception of the arrangements of the contact member 104'). Alternatively, in other arrangements, the implant device 110' can have a contact member 104' as disclosed herein and can have a securing element that is similar to any of the other securing elements shown herein, such as any of the arrangements of the securing element 110 disclosed herein.

Any of the components of any of the implant arrangements disclosed herein can be made from Nitinol or any other elastic or super elastic material, including any other shape memory materials, or any mechanically expandable material such as stainless steel or otherwise. In any arrangements disclosed herein, the contact member (such as contact member 104) can have a spherical, cylindrical, or other shape, such as the shape of an elongated bullet, a stent, a mushroom, or other non-round or non-cylindrical shape or any of the shapes described or shown with respect to any of the arrangements disclosed herein. In any arrangements disclosed herein, the contact member may comprise a series of interconnected struts (that can, but are not required to, form a diamond shaped pattern across all or a portion of the surface of the contact member), or may be made from a series of ribs or paddles which form the expandable device.

Figure 7:
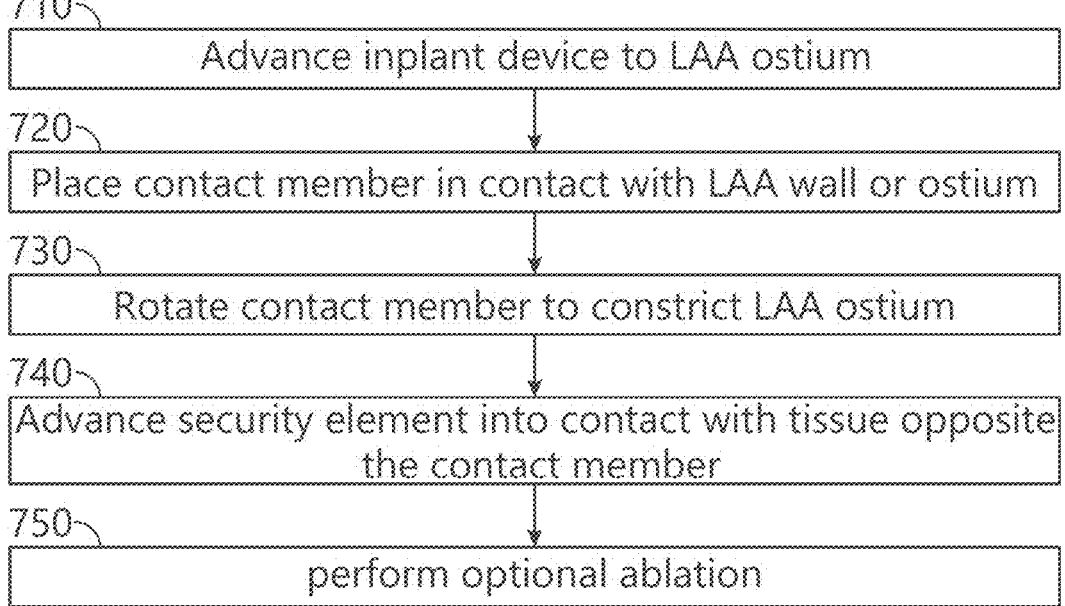
FIG. 7 shows a flowchart describing a LAA occlusion, closure, or elimination procedure using the implant device.

FIG. 7 depicts a flowchart for one embodiment of a method for closing or eliminating the LAA using the aforementioned devices and techniques. In one aspect, at step 710, the implant device 102 can be advanced to the LAA ostium upon completion of any ablation, ECG detection, or mapping procedures performed elsewhere in or around the heart.

In some embodiments, the implant device 102 may be in a fully deployed state (i.e., the contact member 104 and securing element 110 are both deployed from catheter 112) or a partially deployed state (i.e., the contact member 104 is deployed from catheter 112 but the securing element 110 is not) when the implant device 102 is positioned at or near the LAA. In other embodiments, the 102 implant device may be in a non-deployed state (i.e., the contact member 104 and securing element 110 are both still constrained within catheter 112) when the implant device 102 is positioned at or near the LAA, and the contact member 104 can be deployed at that time. Regardless, at step 720, the outer surface of the contact member can be placed in contact with a portion of the LAA interior wall or ostium.

In another aspect, the contact member 104 can then be rotated such that the tissue anchors 118 of the contact member 104 engage with the LAA or ostium tissue at step 730. In this manner, as the contact member 104 rotates about its central axis, the LAA ostium is constricted and/or closed about the rotational axis of the implant device 102.

At step 740, once the LAA ostium is sufficiently constricted or closed, the securing element 110 can be advanced distally until it engages with tissue opposite the contact member 104 (as depicted in, for example, FIGS. 6E or 6F). In some embodiments, such as where the electrodes 122 of the securing element 110 were used in conjunction with a prior ablation, ECG detection, or mapping procedure elsewhere in the heart, the securing element 110 may already be deployed from catheter 112 prior to the implant device 102 being advanced to the LAA. In such cases, the securing element 110 may need only be advanced distally toward the contact member 104. In other embodiments, the securing element 110 may be deployed from catheter 112 and expanded at step 740 prior to advancing the securing element 110 distally toward the contact member 104.

Once the securing element 110 is advanced against the tissue opposite the contact member 104 and the constricted tissue between the securing element 110 and the contact member 104 is effectively retained and locked in place, at step 750 further ablative procedures may be performed to, for example, isolate the LAA tissue. In some embodiments, any one of electrodes 117 of the contact member 104 (or the contact member itself where it, as a whole, serves as an electrode) or electrodes 122 of the securing element 110 (or the securing element itself where it, as a whole, serves as an electrode) can be used in conjunction with a body surface electrode placed on the patient's skin to perform unipolar ablation. Alternatively, any pair of electrodes, including any of electrodes 117 of the contact member 104 (or the contact member itself where it, as a whole, serves as an electrode) and electrodes 122 of the securing element 110 (or the securing element itself where it, as a whole, serves as an electrode) can be used in conjunction with one another to perform bipolar ablation.

Figure 8A:
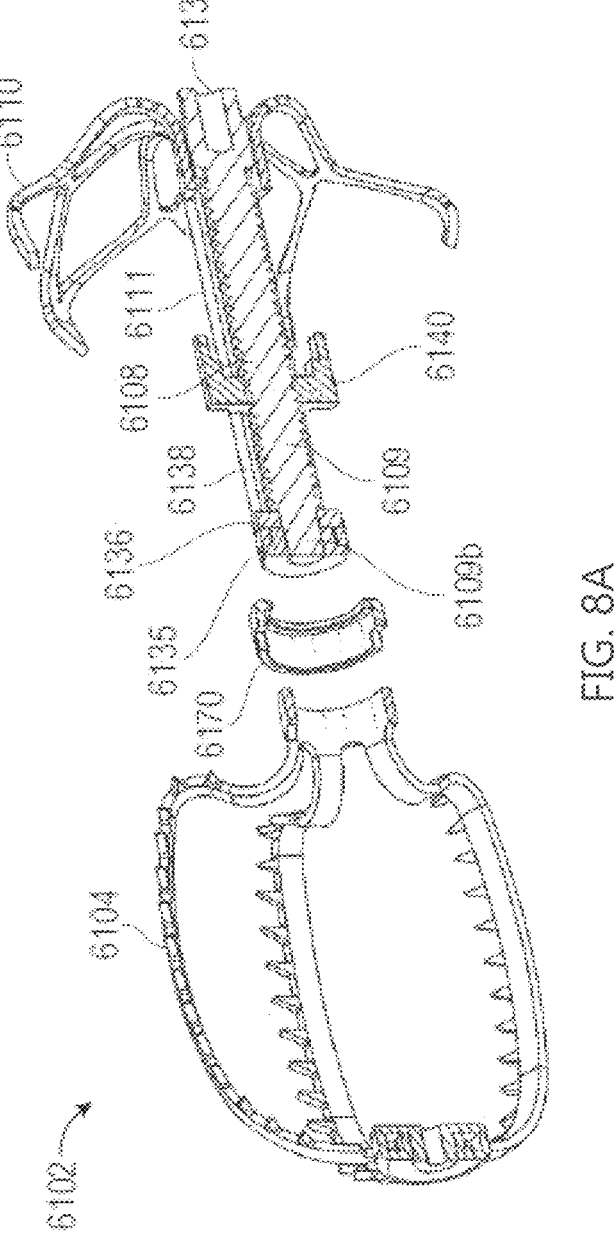
FIGS. 8A-8C show another arrangement of a treatment device for closing or occluding an LAA.
Figure 8B:
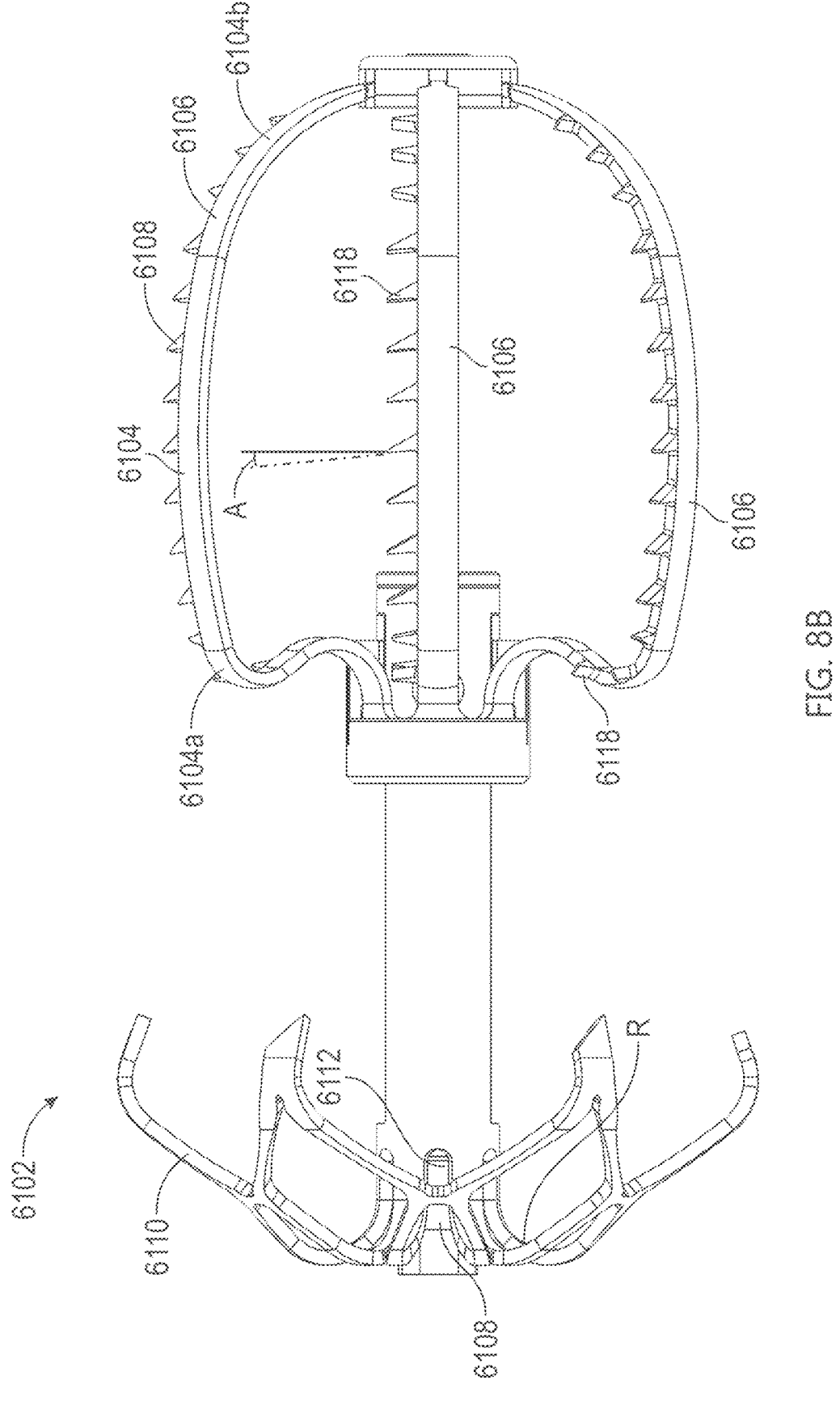
Figure 8C:
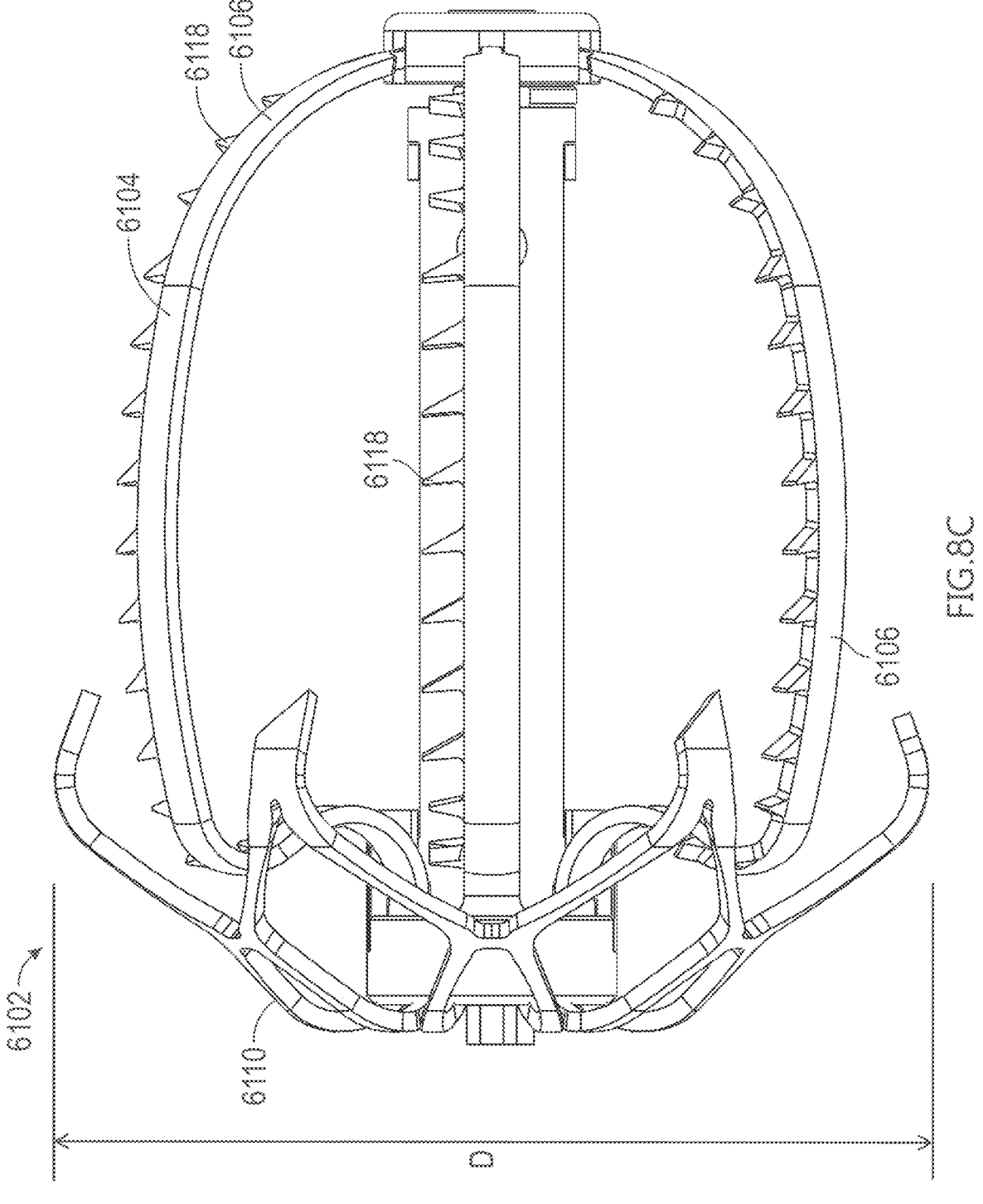

FIGS. 8A-8C show another arrangement of a treatment device 6100 having an implant device 6102 having a contact member 6104, and retention element 6108, and securing element 6110. In any arrangements disclosed herein, the implant device 6102 can have any of the components, features, or other details of any other treatment device arrangements or implant device arrangements disclosed herein, including without limitation any of the other arrangements of the treatment devices or systems 100, 140, 4000, 6000 or implant devices 102, 104, 4002, 6002 described herein, in any combination with any of the components, features, or details of the implant device 6102 shown in FIGS. 8A-8C. Similarly, any components, features, or other details of any of the other treatment device arrangements or implant device arrangements disclosed herein can have any of the components, features, or other details of any arrangements of the implant device 6102 disclosed herein in any combination with any of the components, features, or details of the other arrangements of the treatment device and/or implant device disclosed herein.

With reference to FIGS. 8A-8C, any arrangements of the contact member 6104 disclosed herein can have a plurality of tissue anchors or teeth 6118 (also referred to as nubs) or other similar features configured to penetrate or engage the tissue of the LAA. The tissue anchors 6118 can be configured to penetrate into a tissue within the LAA when the contact member 4004 is expanded against the tissue of the LAA and/or when the contact member 4004 is rotated or twisted within the LAA. The tissue anchors 6118 can be positioned on one side of the struts 6106 of the contact member 6104, for example, to point in the direction of intended rotation of the contact member 6104. In other arrangements, the tissue anchors 6118 can be positioned on both sides of the struts 6106 of the contact member.

In any arrangements disclosed herein, the tissue anchors or teeth 6118 of the contact member can be asymmetrical or otherwise be formed at an angle (such as angle A, shown in FIG. 8C). In some arrangements, as shown, the tissue anchors 6118 can be directed toward a proximal end 6104a of the contact member 6104 by an angle A. In this arrangement, in some arrangements, the tissue anchors can be angled toward an ostium. For example and without limitation, the anchors can have a proximal surface that is angled back toward the proximal end of the contact member by an angle A of 5° or approximately 5°, or from 2° or approximately 2° to 15° or approximately 15° or more, or from 5° or approximately 5° to 10° or approximately 10°, or of any value within the foregoing ranges or to and from any values within the foregoing ranges. In some arrangements, angling the tissue anchors toward the proximal end of the contact member can improve the engagement (e.g., grip) of the tissue anchors in the tissue of the LAA as the retention element and/or the securing element are drawn toward the contact member, which can cause the contact member to be pulled toward the ostium of the LAA. In other arrangements, the tissue anchors 6118 can have a distal surface that can be angled toward a distal end 6104b of the contact member 6104, or can have a mix of tissue anchors having a proximal surface angled toward the proximal end of the contact member, tissue anchors having a distal surface angled toward the distal end of the contact member, and/or symmetrically shaped tissue anchors.

In some arrangements, a length of any of the tissue anchors disclosed herein (for example and without limitation, the tissue anchors 6118), measured from the base of the tissue anchor to a distal tip of the tissue anchor along a centerline of the tissue anchor, can be 0.6 mm, or approximately 0.6 mm. In some arrangements, the length of the tissue anchors can be 0.5 mm, or from 0.4 mm (or approximately 0.4 mm, or less than 0.4 mm) to 0.8 mm (or approximately 0.8 mm, or more than 0.8 mm), or from 0.5 mm (or approximately 0.5 mm) to 0.7 mm (or approximately 0.7 mm), or of any value or range of values within any of the foregoing ranges.

With reference to FIGS. 8A-8C, in some arrangements, the tissue anchors 6118 can be positioned along a length of the struts 6108 of the contact member 6104 from the proximal end 6104a of the contact member 6104 to the distal end 6104b of the contact member 6104, or near or adjacent to the proximal end 6104a of the contact member 6104 to a point that is adjacent to or near to the distal end 6104b of the contact member 6104. In some arrangements, the tissue anchors 6118 can be positioned along at least 80% of a length of the struts 6108 of the contact member 6104, or from 60% (or approximately 60%, or less than 60%) to 100% (or approximately 100%) of the length of the struts 6108 of the contact member 6104, or of any values or ranges of values within the foregoing ranges.

The securing element 6110 shown in FIGS. 8A-8C is shown in an expanded state (e.g., is in the second state) and spaced apart from the contact member 6104 that is also in an expanded, second state. In some arrangements of the implant device 6102, similar to the implant device 6002 described above, the securing element 6110 can be axially secured to the retention element 6108. Some arrangements of the retention element 6108 can have a threaded shaft that can be positioned within a body portion of the securing element 6110. The threaded shaft 6109 can be permitted to rotate freely within the body portion 6111 of the securing element 6110. The threaded shaft 6109 can also be threadedly coupled with the contact member 6104. In this configuration, rotating the threaded shaft 6109 in a first direction can cause the securing element 6110 to advance axially toward the contact member 6104. Rotating the threaded shaft 6109 in a second direction which is opposite to the first direction can cause the securing element 6110 to withdraw or move axially away from the contact member 6104. With reference to FIG. 8C, the securing element 6110 can have a bend radius or radius of curvature (represented by R in FIG. 8B) near a base of the struts of the securing element 6110 that can be 1.0 mm (or approximately 1.0 mm) in size, or from 0.8 mm (or approximately 0.8 mm, or less than 0.8 mm) to 1.0 mm (or approximately 1.0 mm, or more than 1.0 mm), or from 0.6 mm (or approximately 0.6 mm, or less than 0.6 mm) to 1.4 mm (or approximately 1.4 mm, or more than 1.4 mm), or of any values or ranges of values within the foregoing ranges. In any arrangements disclosed herein, the securing element (including securing element 6110) can have an overall outside diameter (represented by D in FIG. 8C) of 13 mm (or approximately 13 mm), or from 10 mm (or approximately 10 mm, or less than 10 mm) to 20 mm (or approximately 20 mm, or more than 20 mm), or from 12 mm (or approximately 12 mm) to 17 mm (or approximately 17 mm), or of any values or ranges of values within the foregoing ranges.

In some arrangements, with reference to FIG. 8C, the space 6112 between the struts (also referred to herein as arms) of the securing element 6110 can be configured to reduce the stress in the struts and allow for a better stress and/or strain distribution along a length of the base portion of the struts of the securing element 6110. By increasing the length of the space between the struts of the securing element 6110, the struts are able to bend or flex more in the base portion of the struts, therein optimizing the stress and/or strain distribution along a length of the base portion of the struts.

In some arrangements, the retention element 6108 can have a head 6130 coupled with (e.g., integrally formed with) the threaded shaft 6109, the head 6130 being configured to couple with an end portion of an intermediate member of the catheter (not shown) so that a rotation or torque applied to the intermediate member can cause an equal rotation or torque to be applied to the head 6130 and the threaded shaft 6109 of the retention element 6108. In some arrangements, the retention element 6108 can be axially coupled with the body portion 6111 of the securing element 6110 so that the retention element 6108 and the securing element 6110 move together in either axial direction. For example and without limitation, in some arrangements, the retention element 6108 can have a first retainer 6135 that can be coupled with (e.g., welded to, press fit, or otherwise attached to) a distal end 6109b of the threaded shaft 6109 and a second retainer 6136 that can be positioned within and be axially constrained within the slot 6138 formed in the body portion 6111 of the securing element 6110.

The first retainer 6135 can prevent a proximal axial movement of the threaded shaft 6109 (i.e., in the proximal direction, away from the contact member 6104) relative to the body portion 6111 of the securing element 6110. Because the second retainer 6136 can have an opening axially therethrough that is smaller than the major diameter of the threaded portion of the threaded shaft 6108, the second retainer 6136 can prevent a distal axial movement of the threaded shaft 6109 (e.g., in the distal direction, toward the contact member 6104) relative to the body portion 6111 of the securing element 6110. In this configuration, any axial movement of the retention element 6108 will cause the simultaneous and equal axial movement of the securing element 6110. A proximal end portion of the contact member 6104 can have a collar member 6170. In some arrangements, the collar member 6170 can be used to constrain the post 6140 to the contact member 6104 so that the post 6140 cannot become disengaged from the contact member 6104.

FIGS. 9A-9J show another arrangement of a treatment system 6300 having an arrangement of an implant 6302 having a contact member 6304, a retention element 6308, and a securing element 6310. In any arrangements disclosed herein, the treatment system 6300 and/or implant device 6302 can have any of the components, features, or other details of any other treatment device arrangements or implant device arrangements disclosed herein, including without limitation any of the other arrangements of the treatment devices 100, 140, 4000, 6000, 6100 and/or implant devices 102, 104, 4002, 6002, 6102 disclosed herein, in any combination with any of the components, features, or details of the treatment system 6300 and/or the implant device 6302 shown in FIGS. 9A-9J. Similarly, any components, features, or other details of any of the other treatment device arrangements or implant device arrangements disclosed herein can have any of the components, features, or other details of any arrangements of the treatment device 6300 and/or implant device 6302 disclosed herein in any combination with any of the components, features, or details of the other arrangements of the treatment device and/or implant device disclosed herein.

Figures 9A, 9B:
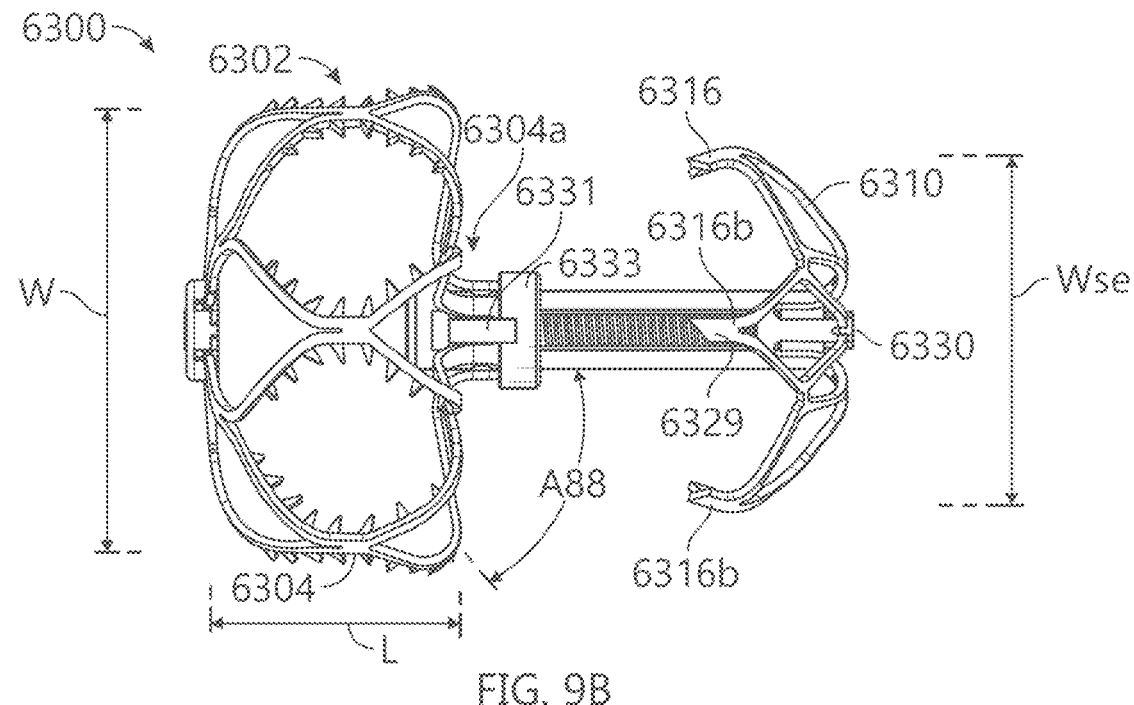
FIGS. 9A-9J show another arrangement of a treatment device for closing or occluding an LAA.
Figure 9C:
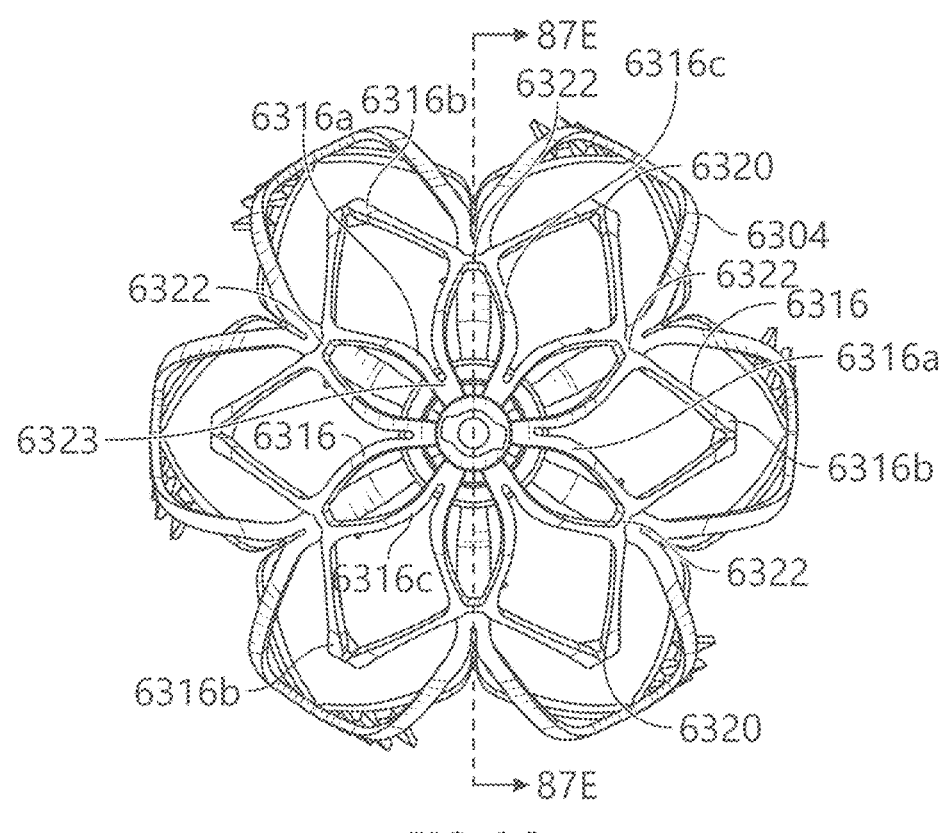
Figure 9D:
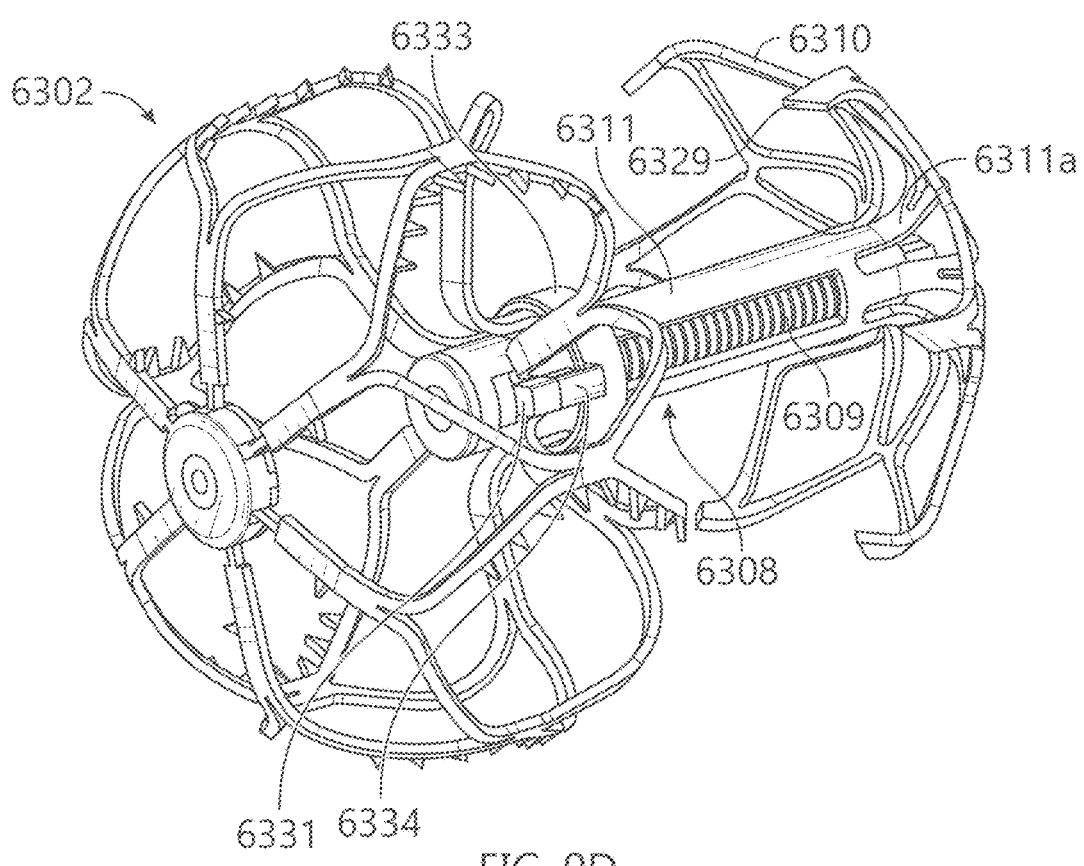

FIG. 9A shows an isometric view of the implant device 6302, in which the securing element 6310 that has been expanded (e.g., is in the second state) is spaced apart from the contact member 6304 that is also in an expanded, second state. FIG. 9B shows a side view of the implant device 6302 and the expanded securing element 6310 spaced apart from the implant device 6302. FIG. 9C shows an end view of the implant device 6302.

With reference to FIGS. 9A-9J, in some arrangements of the implant 6302, the securing element 6310 can be axially coupled with or secured to a retention element 6308. Some arrangements of the retention element 6308 can have a threaded shaft 6309 that can be positioned within a body portion 6311 of the securing element 6310 in an operable state. The body portion 6311 can have a cylindrical shape with an opening axially therethrough that can be sized and configured to receive the threaded shaft 6309 therein. In some arrangements, the threaded shaft 6309 can be permitted to rotate freely within the body portion 6311 of the securing element 6310 in either direction. The threaded shaft 6309 can also be threadedly coupled with the contact member 6304. In this configuration, rotating the threaded shaft 6309 in a first direction can cause the securing element 6310 to advance axially toward the contact member 6304 and rotating the threaded shaft 6309 in a second, opposite direction can cause the securing element 6310 to move axially away from the contact member 6304.

Figure 9E:
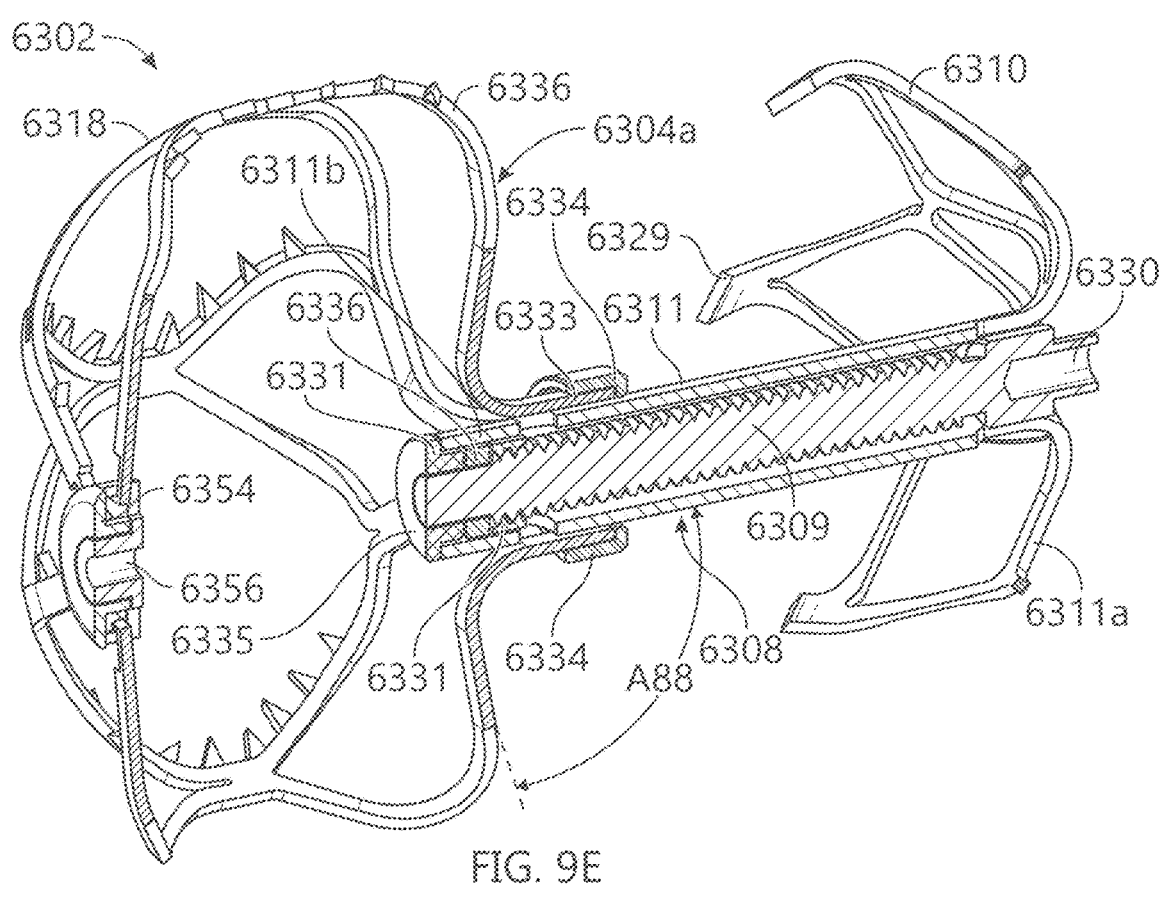
Figure 9F:
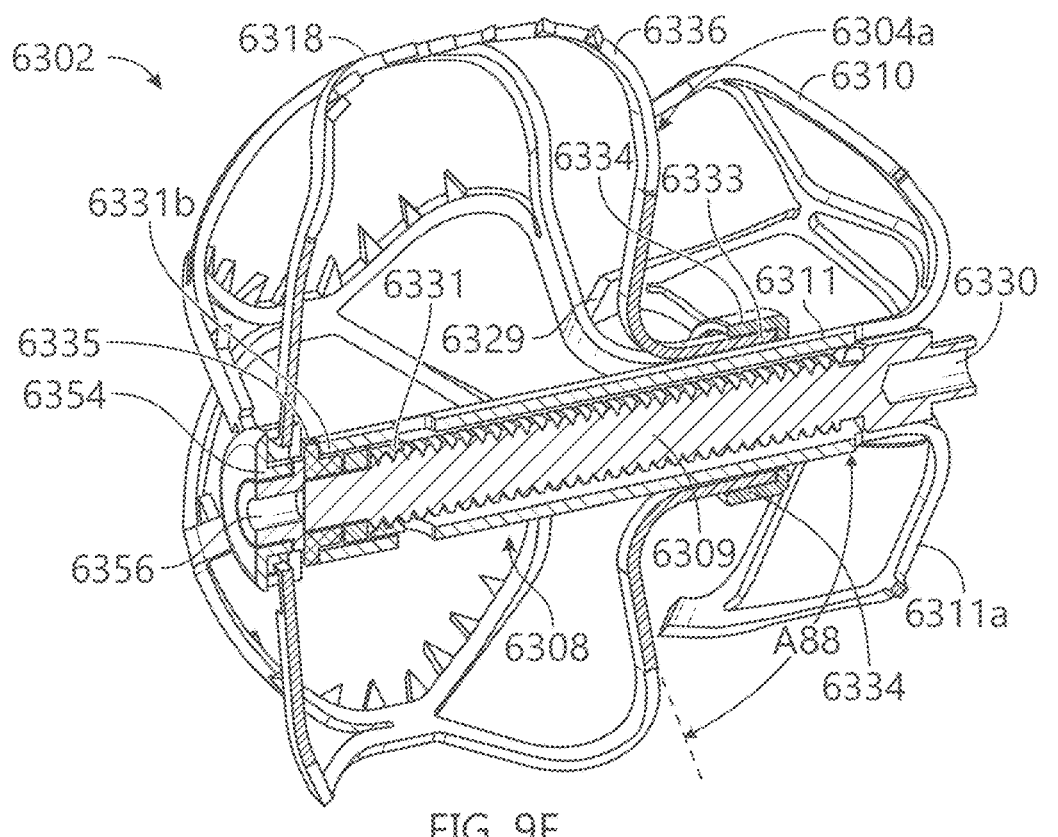
Figure 9G:
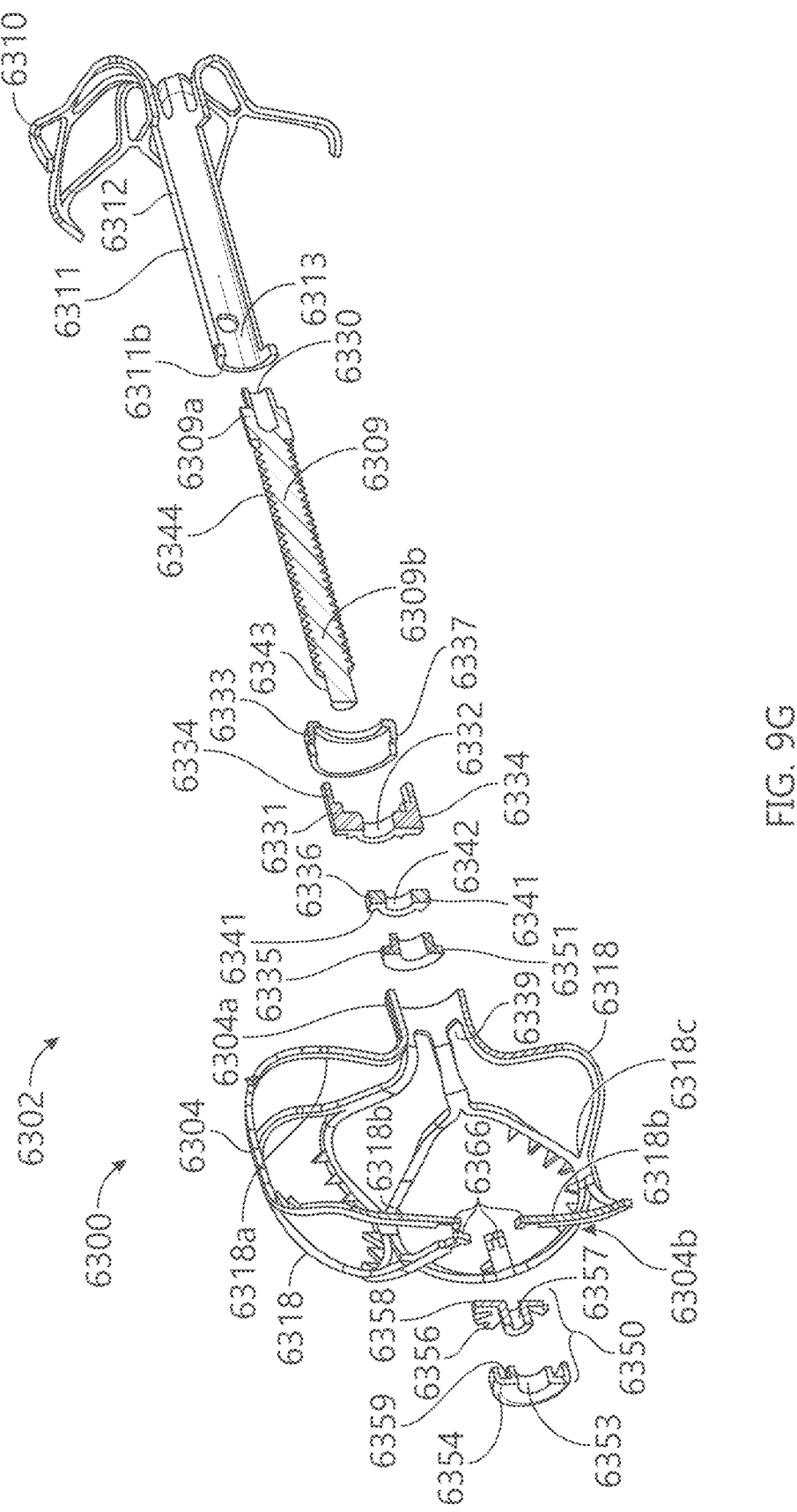
Figure 9H:
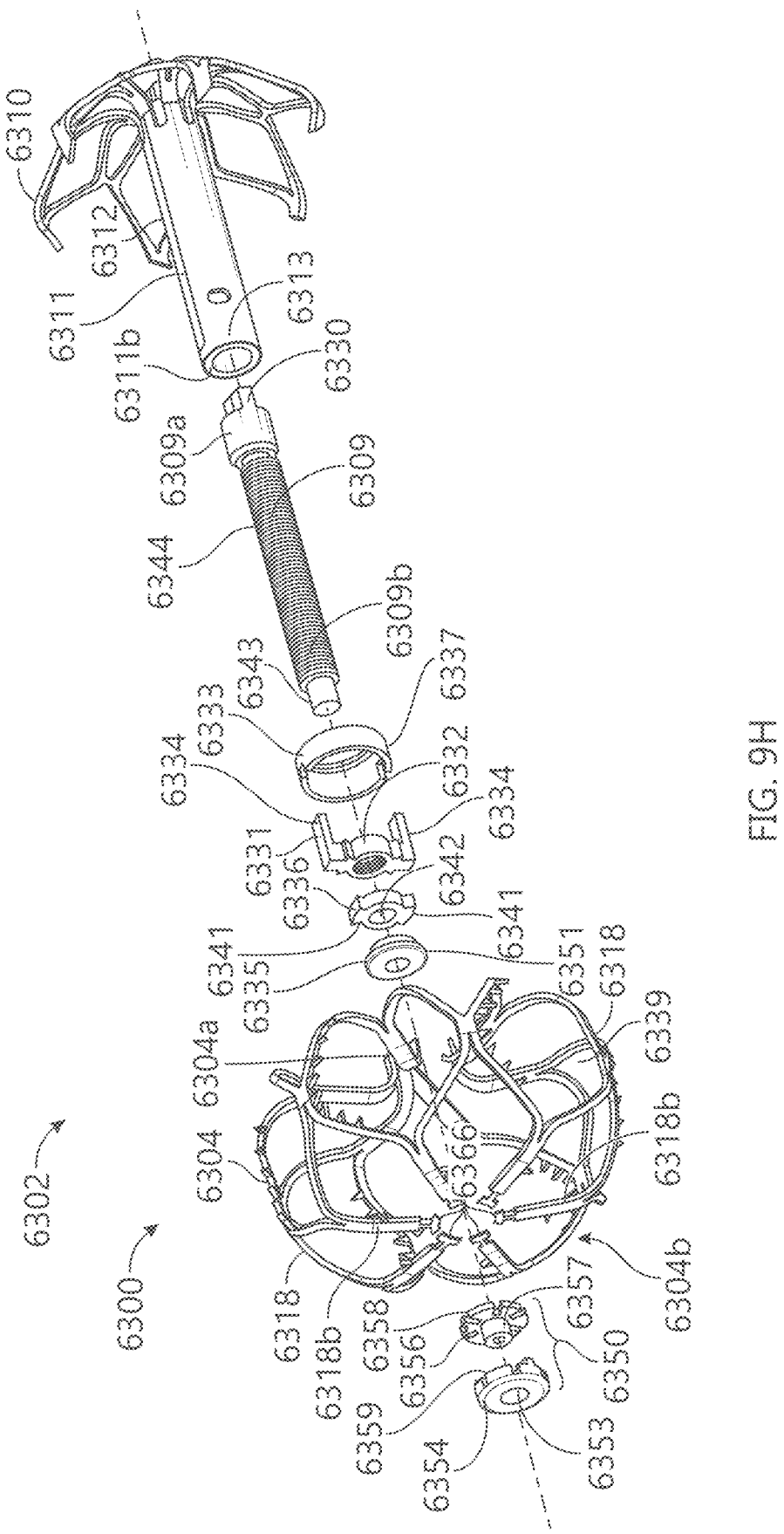
Figure 9I:
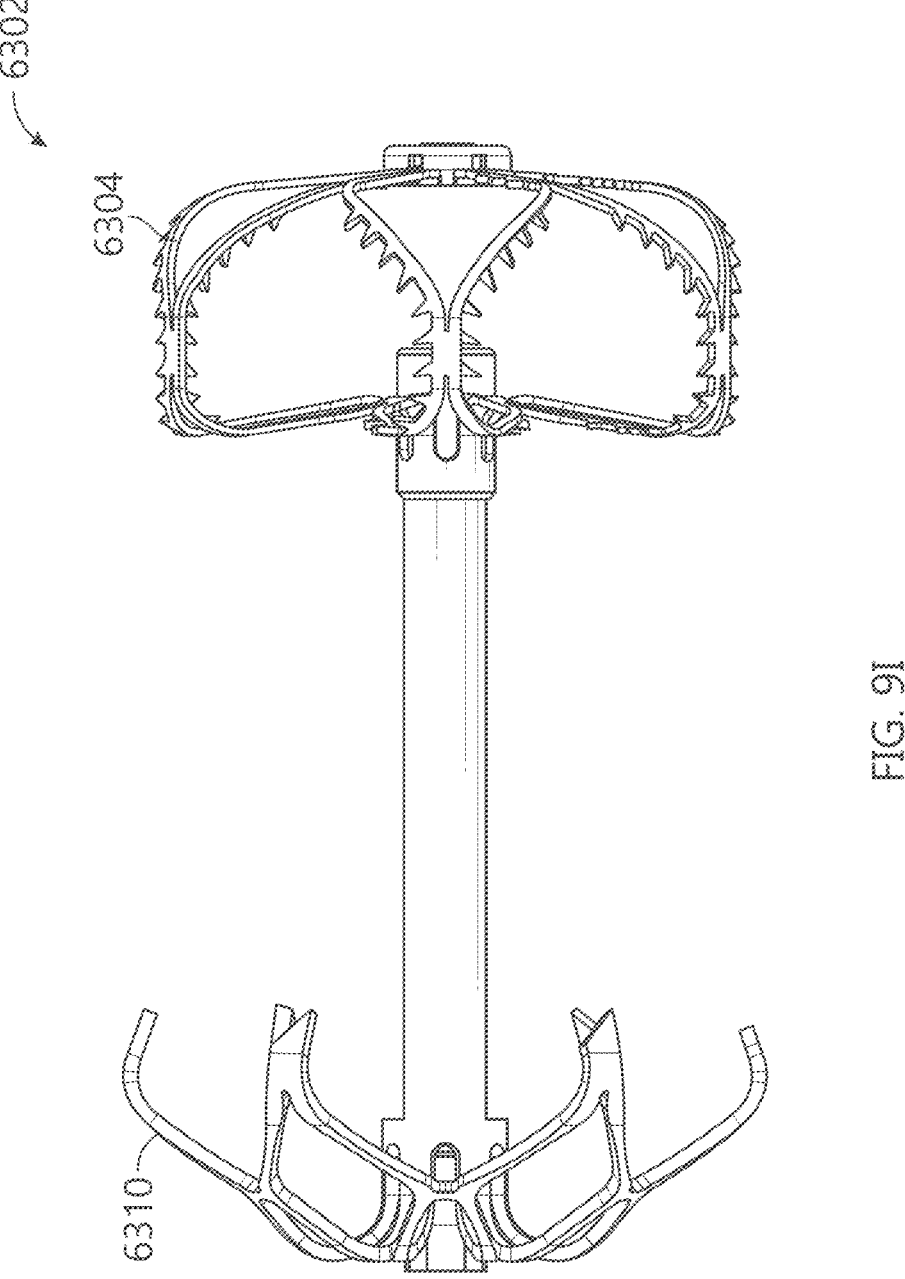
Figure 9J:
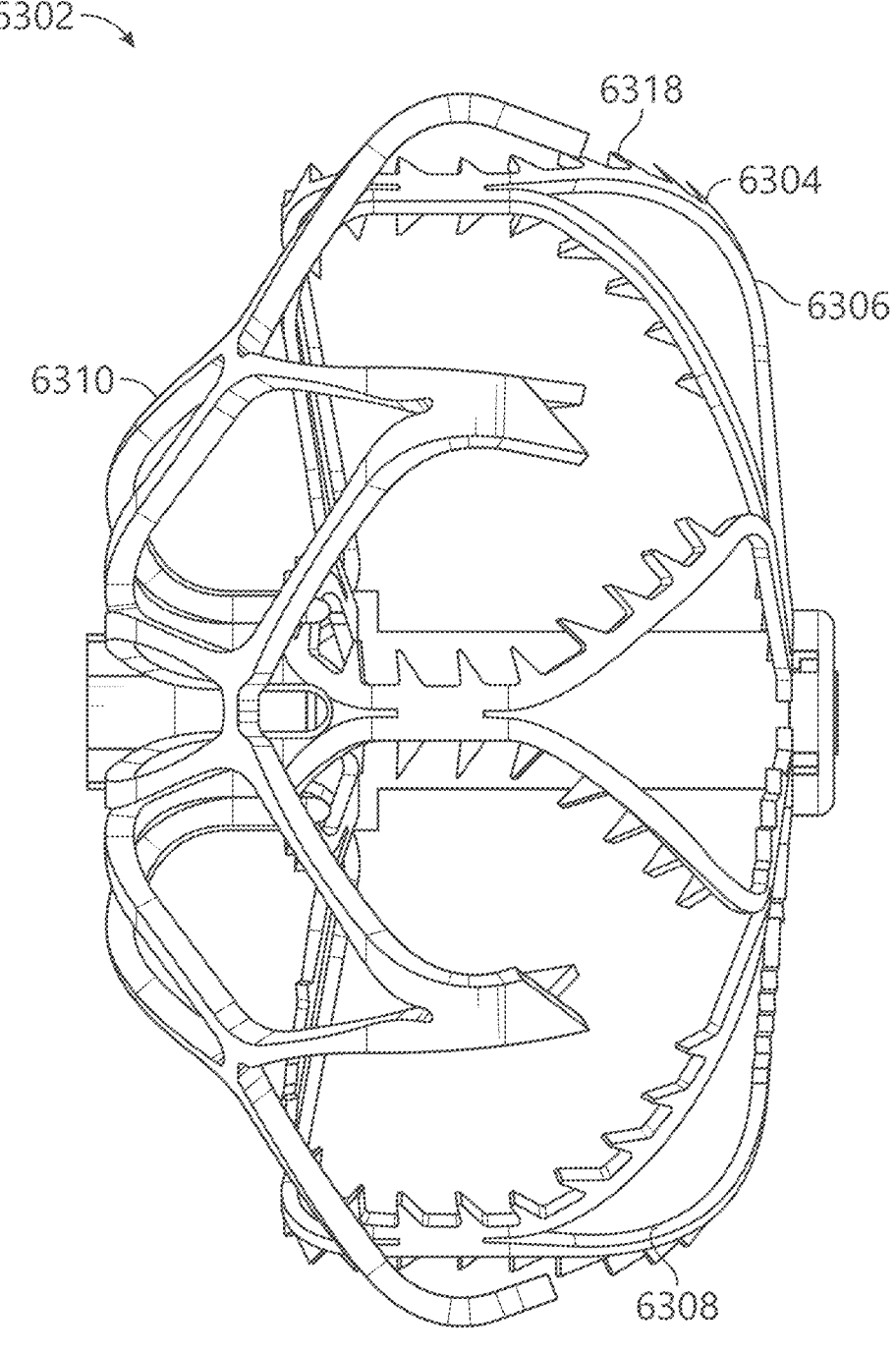

FIG. 9F is a section view of the arrangement of the implant 6302 shown in FIG. 9A, showing the securing element 6310 advanced to a position that is adjacent to the contact member 6304. FIG. 9G is an exploded section view of the arrangement of the implant 6302 shown in FIG. 9A. FIG. 9J is a side view of the arrangement of the implant shown in FIG. 9A, also showing the securing element 6310 advanced to a position that is adjacent to the contact member 6304. Though some arrangements of the implant may be configured to permit the securing element 6310 to advance to a position that is adjacent to the contact member 6304 such that the distal end portions of the securing element 6310 extend past the proximal end of the contact member 6304, as shown in FIG. 9J. However, for some arrangements, when implanted in the body, some tissue of the LA and/or the LAA may be positioned between the securing element 6310 and the contact member 6304 which may limit the range of movement of the securing element 6310 relative to the contact member 6304. As mentioned, rotating the threaded shaft 6309 in a second direction which is opposite to the first direction can cause the securing element 6310 to withdraw or move axially away from the contact member 6304. FIGS. 9E and 9H show the securing element 6310 advanced to a position that is spaced apart from the contact member 6304. In some arrangements, without limitation, the first direction can be clockwise.

In some arrangements, the securing element 6310 can have a plurality of arms or struts 6316 extending away from a proximal end portion 6311*a* of the body portion 6311 of the securing element 6310. In some arrangements, the plurality of struts 6316 can each initially bend radially outwardly at a proximal end portion 6316*a* thereof and can each have a distal end portion 6316*b* that can be, in the second or expanded state of the securing element 6310, closer to the contact member 6304 than the proximal end portion 6316*a* of the struts 6316. Each of the struts 6316 can have a middle section 6316*c* that, in a second or expanded state, can angle outwardly and forward toward the contact member. In some arrangements, the middle section 6316*c* can angle forward at an angle that is 45° (or approximately) 45° relative to an axial or longitudinal axis of the body portion 6311 of the securing element 6310, or from 35° (or approximately 35°, or less than) 35° to 60° (or approximately 60°, or more than) 60° relative to the axial or longitudinal axis of the body portion 6311.

With reference to FIG. 9J, in some arrangements, at least a distal end portion 6316*b* of some of the plurality of struts 6316 can overlap with the contact member 6304 when the securing element 6310 is advanced in the distal direction (e.g., when the securing element 6310 is moved to a position that is adjacent to the contact member 6304). For example and without limitation, in any arrangements of the implant disclosed herein, at least a distal end portion 6316*b* of some of the plurality of struts 6316 can overlap a proximal end of the contact member by 1 mm, approximately 1 mm, or less than 1 mm, or 2 mm or approximately 2 mm, or 2 mm or approximately 2 mm, or from 1 mm or less than 1 mm to 3 mm or more than 3 mm. As another nonlimiting example, in any arrangements of the implant disclosed herein, at least a distal end portion 6316*b* of some of the plurality of struts 6316 can overlap a proximal end of the contact member such that at least 20% or approximately 20%, or at least 40% or approximately 40%, or at least 50% or approximately 50%, or from 20% or approximately 20% to 50% or approximately 50% of an overall length of at least a distal end portion 6316*b* of some of the plurality of struts 6316 in a deployed state can extend past a proximal end portion of the contact member. In some arrangements, the implant can be configured such that the arms or struts of the securing elements can extend into the spaces or voids between the arms or struts of the contact member when the securing element has been advanced toward the contact member.

In any arrangements of the securing element 6310 disclosed herein, each of the struts 6316 can have one or more interconnections 6320 with adjacent struts 6316 along a length of each of the struts 6316, or a plurality of the struts 6316. For example and without limitation, with respect to FIG. 9C, each of the struts 6316 can have a first interconnection 6320 at an end portion 6316*b* of each of the struts 6316, wherein the first interconnection 6320 is an interconnection between the distal end portions 6316*b* of two adjacent struts 6316. Additionally, in some arrangements, each of the struts 6316 can also have a second interconnection 6322 in a middle portion 6316*c* of each of the struts 6316, wherein the second interconnection 6322 is an interconnection between the middle portions 6316*c* of two adjacent struts 6316. In this configuration, each of the struts 6316 of the securing element 6310 can have a first and a second interconnection along a length thereof with an adjacent strut 6316. Additionally, any arrangements of the securing element 6310 can have one or more interconnections 6323 at the proximal end portions 6316*a* of the struts 6316, or at the proximal end portions 6316*a* of a plurality of the struts 6316.

The interconnections 6320, 6322, 6323 can provide additional rigidity and strength to the entire securing element 6310. Additionally, in some arrangements, each of the interconnections 6320, 6322, 6323 can also provide an additional point of securement of each of the struts 6316 to the securing element 6310 so that, if a strut becomes fractured or broken, the first interconnection 6320 and/or the second interconnection 6322 can couple or secure the broken or fractured strut 6316 to the securing element 6310 and prevent the broken or fractured strut 6316 from breaking loose and moving into the patient's heart or blood stream. Additionally, in some arrangements, each of the struts 6316 can have a sharp distal end portion 6316*b* wherein, in some arrangements, the distal end portion 6316*b* can have two struts that are coupled together at the distal end portion 6316*b* of the struts. In some arrangements, the distal end portion 6316*b* can have a sharp point that is designed to penetrate tissue. In some arrangements, the distal end portion 6316*b* can have a point that is configured to grab or engage the tissue without penetrating the tissue. Additionally, in some arrangements, the distal end portion 6316*b* of each of the struts can have a sloped or angled surface 6329 that can assist with the penetration of the distal end portion 6316*b* into the tissue.

In some arrangements, the first and/or second interconnections 6320, 6322 can increase a rigidity of the securing element 6310, at least torsionally. In some arrangements, with the more torsionally rigid configuration having interconnections, the struts 6316 can be made thinner in cross-sectional size, which can improve tissue ingrowth into the securing element 6310 in some arrangements and/or reduce a weight of the securing element 6310. In some arrangements, without limitation, the cross-sectional area or size of the struts 6316 can be the same as or approximately the same as a 2-0 suture.

Similarly, any arrangements of the contact member 6304 disclosed herein can have one or more interconnections between adjacent struts 6318 along a length of each of the struts 6318, or a plurality of the struts 6318. For example and without limitation, with respect to FIG. 9G, each of the struts 6318 can have a first interconnection at or adjacent to an end portion 6318b of each of the struts 6318, wherein the first interconnection is an interconnection between the distal end portions 6318b of two adjacent struts 6318. Additionally, in some arrangements, each of the struts 6318 can also have a second interconnection in a middle portion 6318c of each of the struts 6318, wherein the second interconnection is an interconnection between the middle portions 6318c of two adjacent struts 6318. In this configuration, each of the struts 6318 of the contact member 6304 can have a first and a second interconnection along a length thereof with an adjacent strut 6318. Additionally, any arrangements of the contact member 6304 can have one or more interconnections at the proximal end portions 6318a of the struts 6318, or at the proximal end portions 6318a of a plurality of the struts 6318.

The interconnections can provide additional rigidity and strength to the entire contact member 6304. Additionally, in some arrangements, each of the interconnections can also provide an additional point of securement of each of the struts 6318 to the contact member 6304 so that, if a strut becomes fractured or broken, the first interconnection, the second interconnection, and/or the interconnections that can be at the proximal end portion of the contact member 6304 can couple or secure the broken or fractured strut 6318 to the contact member 6304 and prevent the broken or fractured strut 6318 from breaking loose and moving into the patient's heart or blood stream.

In some arrangements, the retention element 6308 can have a head 6330 coupled with the threaded shaft 6309, the head 6330 being configured to couple with an end portion of an intermediate member of the catheter (such as the end portion 8098b of the catheter shown in FIG. 18C) so that a rotation or torque applied to the intermediate member can cause an equal rotation or torque to be applied to the head 6330 and the threaded shaft 6309 of the retention element 6308. In some arrangements, the retention element 6308 can be axially coupled with the body portion 6311 of the securing element 6310 so that the retention element 6308 and the securing element 6310 move together in either axial direction. For example and without limitation, in some arrangements, the threaded shaft 6309 of the retention element 6308 can threadedly engage with a threaded drive element 6331 that can have a threaded opening 6332 axially therethrough that can be configured to receive the threaded shaft 6309 therethrough. As will be described, the drive element 6331 can be configured to be supported by the other components of the implant 6302 so that the drive element 6331 is prevented from rotating. Further, some arrangements of the implant 6302 can be configured to permit the drive element 6331 to move axially along the length of the body portion 6311 of the securing element 6310 as the threaded shaft 6309 is rotated. In this configuration, the drive element 6331 can be advanced axially in either direction by rotating the threaded shaft 6309.

A retainer cap 6333 can be used to couple the drive element 6331 to a proximal end 6304a of the contact member 6304. In some arrangements, the retainer cap 6333 can be coupled with (e.g., welded to, press fit with, or otherwise attached to) the drive element 6331 with a portion of the proximal end 6304a of the contact member 6304 trapped or secured between the drive element 6331 and the retainer cap 6333. For example and without limitation, drive element 6331 can be positioned within an opening 6339 in the proximal end 6304a of the contact member 6304, distal to an annular ring of the proximal end 6304a of the contact member 6304, and the retainer cap 6333 can be coupled with the drive element 6331 with the proximal end 6304a of the contact member 6304 captured between the drive element 6331 and the retainer cap 6333. In some arrangements, the drive element 6331 can have posts or tabs 6334 that can extend into the slots 6312 of the body portion 6311 of the securing element 6310 to inhibit (e.g., prevent) the drive element 6331 from rotating when the threaded shaft 6309 is rotated into the drive element 6331. Additionally, in some arrangements, the tabs 6334 can engage with recesses 6337 formed in the retainer cap 6333 to provide an overlap between the drive element 6331 and the retainer cap 6333 and thereby improve the connection between the drive element 6331 and the retainer cap 6333.

A first retainer 6335 can be coupled with (e.g., welded to, press fit, or otherwise attached to) a distal end 6309b of the threaded shaft 6309 and a second retainer 6336 can be used to capture the distal end portion 6311b of the body portion 6311 of the securing element 6310 between the first retainer 6335 and the second retainer 6336. The second retainer 6336 can have posts or tabs 6341 that can extend into the slots 6312 of the body portion 6311 of the securing element 6310 to prevent the second retainer 6336 from moving in a distal direction relative to the distal end portion 6311b of the body portion 6311. This can be achieved by sizing the opening 6342 axially through the second retainer 6336 to be slightly oversized as compared to the cylindrical end portion 6343 at the distal end portion 6309b of the threaded shaft 6309, while sizing the opening 6342 to be smaller than the threaded portion 6344 of the threaded shaft 6309 so that the threaded portion 6344 of the threaded shaft 6309 cannot extend through the opening 6342 in the second retainer 6336. In this arrangement, with the second retainer 6336 positioned around the cylindrical end portion 6343 at the distal end portion 6309b of the threaded shaft 6309, the distal end portion 631 1b of the body portion 6311 of the securing element 6310 positioned between the first retainer 6335 and the second 6336, and the first retainer 6335 non-removably coupled with the cylindrical end portion 6343 of the threaded shaft 6309, the threaded shaft 6309 can be non-removably coupled with the securing element 6310.

As mentioned, the first retainer 6335 can prevent a proximal axial movement of the threaded shaft 6309 (i.e., in the proximal direction, away from the contact member 6304) relative to the body portion 6311 of the securing element 6310. Because the second retainer 6336 can have an opening 6342 axially therethrough that is smaller than the major diameter of the threaded portion of the threaded shaft 6308, the second retainer 6336 can prevent a distal axial movement of the threaded shaft 6309 (i.e., in the distal direction, toward the contact member 6304) relative to the body portion 6311 of the securing element 6310. An outside diameter or a flange 6351 of the first retainer 6335 can be greater than the diameter of the opening 6313 at the distal end portion 6311b of the body portion 6311 of the securing element 6310 to prevent the first retainer 6335, which is coupled with an end portion 6309b of the threaded shaft 6309, from passing through the opening 6313. In this configuration, any axial movement of the retention element 6308 (e.g., caused by a rotation of the threaded shaft 6309) will cause the simultaneous and equal axial movement of the securing element 6310 relative to the contact member 6304.

In this configuration, as the threaded shaft 6309 is rotated in a first direction, the drive element 6331 can move axially in a first direction (e.g., a distal axial direction) relative to the securing element 6310 and so that, as the threaded shaft 6309 is rotated in a second direction, which is opposite to the first direction, the drive element 6331 can move axially in a second direction (e.g., a proximal axial direction) that is opposite to the first direction relative to the securing element 6310. As mentioned, the drive element 6331 can be coupled with a proximal end portion 6304*a* of the contact member 6304 such that, as the drive element 6331 is moved axially relative to the securing element 6310, the securing element 6310 can simultaneously and equally move in an axial direction relative to the contact member 6304. In this configuration, the securing element 6310 can be moved toward or away from the contact member 6304 by rotating the head portion 6330 of the threaded shaft 6309 of the retention element 6308.

With reference to FIG. 9G, some arrangements of the contact member 6304 can have a hub 6350 at a distal end portion 6304*b* of the contact member 6304 that can couple with the distal end portions 6318*b* of the struts 6318. The hub 6350 can couple with the distal end portions 6318*b* of the struts 6318 so as to secure the hub 6350 with the distal end portions 6318*b* of the struts 6318 in an axial direction. The hub 6350 can be configured to permit the distal end portions 6318*b* of the struts 6318 to rotate relative to the hub 6350. In some arrangements, the hub 6350 can include a first retention element 6354 and a second retention element 6356. The first retention element 6354 and a second retention element 6356 can have openings 6353 and 6357, respectively, axially therethrough for a guidewire or other instrument to pass through and can be configured to constrain the distal end portions 6318*b* of the struts 6318 in an assembled state. For example and without limitation, the first retention element 6354 can have an annular recess therein that can be sized and configured to receive the distal end portions 6318*b* of the struts 6318 therein and the second retention element 6356 can have slots 6358 formed in the second retention element 6354 that extend in a radial direction and are sized and configured so that the thinned or narrow portion of the distal end portions 6318*b* of the struts 6318 can pass therethrough, but the wider portion at the distalmost end portion of the distal end portions 6318*b* of the struts 6318 cannot pass therethrough. In other words, the slots 6358 can be configured to engage with the tabs or other T-shaped features 6366 formed on the distal end portion 6318*b* of the struts 6318 and to permit the distal end portions 6318*b* to rotate relative to the hub 6350. The second retention element 6356 can also have slots or recesses therein that are configured to engage with tabs formed on the first retention element 6354 to provide a more secure coupling between the first retention element 6354 and the second retention element 6356.

In this configuration, as the threaded shaft 6309 is rotated in a first direction, the securing element 6310 can be advanced toward the contact member 6304 so as to engage with and/or compress any tissue that has constricted or closed as a result of the twisting of the contact member 6304 or the LAA and/or any tissue that is adjacent to the tissue that has constricted or closed as a result of the twisting of the contact member 6304 or the LAA. The distal tips 6316*b* of the arms 6316 of the securing element 6310 can penetrate into the tissue that has been compressed or otherwise inhibit (e.g., without limitation, prevent) the tissue that has constricted around a body of the implant 6302 from opening back up or expanding.

In some arrangements and as described above, the proximal end portion 6304*a* of the contact member 6304 and distal end portion 6304*b* of the contact member 6304 can be formed by struts. In some arrangements, for example and without limitation, the proximal portion of the contact member 6304 or any contact member disclosed herein can be configured to bias any folds or overlapped tissue of the LAA that has formed around the contact member 6304 as a result of the twisting of the contact member 6304 to slide off or move away from the contact member 6304, so that only a minimal amount of folds or overlapped tissue, if any, will be formed around the outside of the contact member 6304. For example and without limitation, in some arrangements, the proximal end portion 6304*a* of the contact member 6304 or any struts thereof can be angled (see angle A88 shown in FIG. 9B) at 85° or approximately 85° relative to a longitudinal axis of the contact member 6304, or at 90° or approximately 90° relative to a longitudinal axis of the contact member 6304, or from 80° or approximately 80° to 100° or approximately 100° relative to a longitudinal axis of the contact member 6304. In any arrangements, the proximal end portion 6304*a* of the contact member 6304 or any struts thereof and/or the distal end portion 6304*b* of the contact member 6304 or any struts thereof can be angled within 30° or approximately 30°, or within from 10° or approximately 10° to 30° or approximately 30°, of an angle that is normal to the longitudinal axis or longitudinal centerline of the contact member 6304. Further, in any arrangements, the mid portion of the contact member 6304 and/or any struts thereof can be approximately parallel with the longitudinal centerline axis of the contact member 6304, or within 30° or approximately 30°, or within from 10° or approximately 10° to 30° or approximately 30°, of parallel with the longitudinal axis of the contact member 6304

Accordingly, in some arrangements, the contact member 6304 can be configured so as to bias the folds or overlapping tissue to occur around the outside of the proximal end portion 6304*a* of the contact member 6304 and/or the body portion 6311 of the retention element 6308, at least after a threshold degree of rotation of the contact member 6304 relative to the LAA (e.g., after 90° or approximately 90° of rotation of the contact member 6304, or from 70° (or approximately) 70° to 110° (or approximately) 110° of rotation of the contact member 6304. In some arrangements, this can be achieved by using a contact member 6304 that has a lateral width or diameter that is equal to or only a little less than an inside size or diameter of the LAA at or adjacent to an end portion of the LAA. For example and without limitation, in any arrangements of the implants disclosed herein, the contact member can have an outer size or diameter that is 80% or approximately 80%, or at least 80%, of an inside size or diameter of the LAA at or adjacent to an end portion of the LAA, or from 70% or approximately 70% to 100% or approximately 100% or greater than 100% of the inside size or diameter of the LAA at or adjacent to an end portion of the LAA, or from 80% or approximately 80% to 90% or approximately 90% of the inside size or diameter of the LAA at or adjacent to an end portion of the LAA.

Further, in any arrangements of the contact member disclosed herein, a length of the contact member along an outer surface of the contact member can be significantly less than a width or diameter of an outer surface of the contact member. Having a shorter length, in some arrangements, can enable the body of the implant (e.g., the body portion of the retention element, for example and without limitation) to have a greater length about which the tissue of the LAA can constrict to occlude or substantially occlude the LAA. In some arrangements, for example and without limitation, a length of the contact member along an outer surface of the contact member (e.g., without limitation, as represented by length L in FIGS. 9B, 10, and 11) can be 50%, or approximately 50%, or less than 50% of a width or a diameter of an outer surface of the contact member (e.g., without limitation, as represented by width W in FIGS. 9B, 10, and 11), or from 40%, or approximately 40% to 60% or approximately 60% of a width or a diameter of an outer surface of the contact member.

Figure 10:
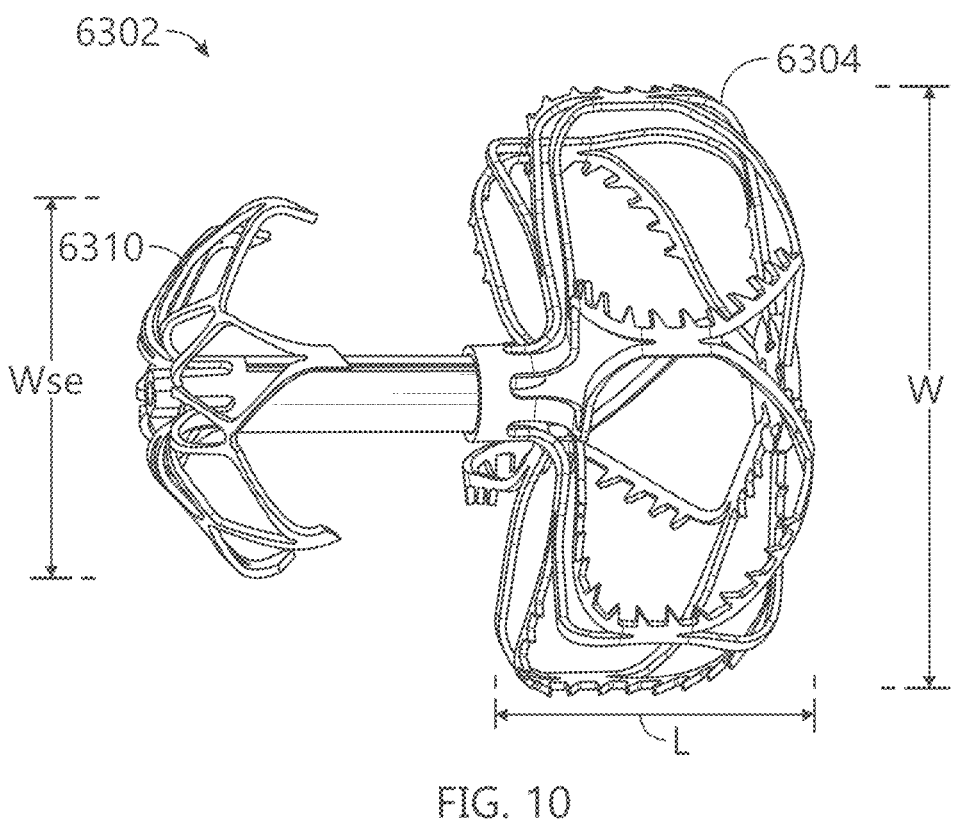
FIG. 10 shows another arrangement of a treatment device for closing or occluding an LAA.
Figure 11:
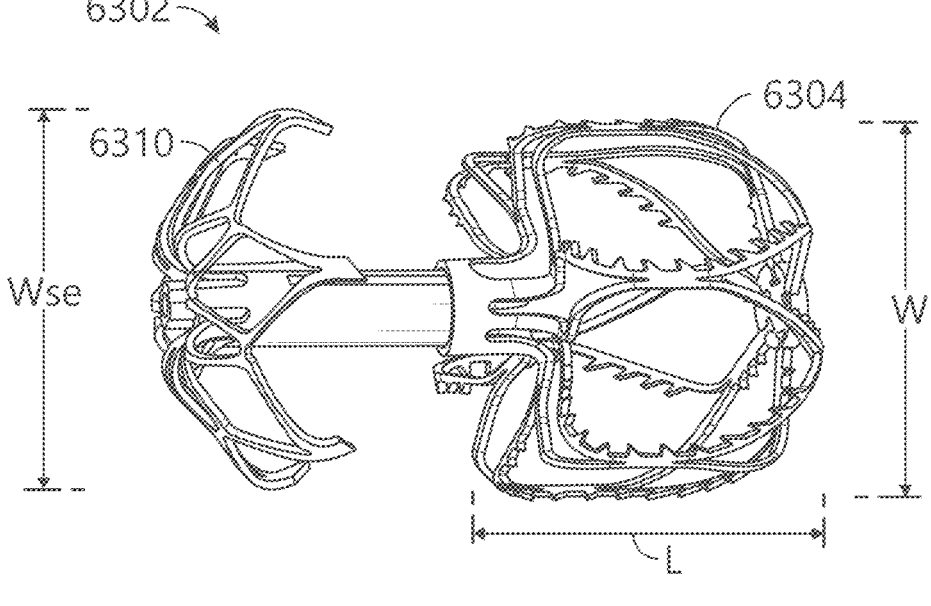
FIG. 11 shows another arrangement of a treatment device for closing or occluding an LAA.

In some arrangements, the width or diameter of the outer surface of the contact member (e.g., without limitation, as represented by width W in FIGS. 9B, 10, and 11) can be greater than a width or a diameter of an outer surface of the securing element (e.g., without limitation, as represented by width Wse in FIGS. 9B, 10, and 11). For example and without limitation, in some arrangements, the width or diameter W of the outer surface of the contact member can be from 50% or approximately 50% to 100% or approximately 100% greater than the width or diameter Wse of an outer surface of the securing element.

In any arrangements disclosed herein, the width or diameter W of the outer surface of the contact member can be 12 mm (0.47 inch) or approximately 12 mm (0.47 inch), or can be 16 mm (0.63 inch) or approximately 16 mm (0.63 inch), or from 10 mm (0.39 in), approximately 10 mm (0.39 in), or less than 10 mm (0.39 in) to 18 mm (0.71 in), approximately 18 mm (0.71 in), or more than 18 mm (0.71 in), or any value or range of values in the foregoing range. In any arrangements disclosed herein, the width or diameter Wse of the outer surface of the securing element can be 13 mm (0.51 inch) or approximately 13 mm (0.51 inch), or can be from 10 mm (0.39 in), approximately 10 mm (0.39 in), or less than 10 mm (0.39 in) to 16 mm (0.63 in), approximately 16 mm (0.63 in), or more than 16 mm (0.63 in), or any value or range of values in the foregoing range.

Figure 12:
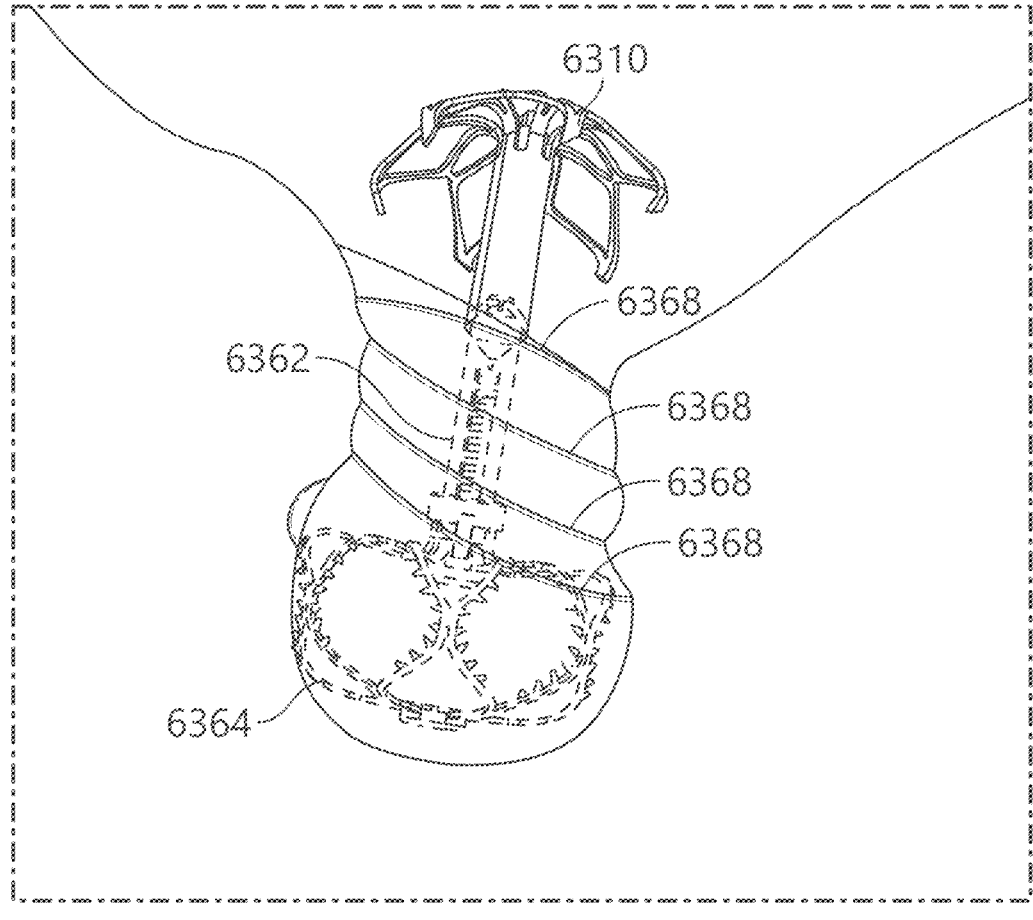
FIG. 12 shows an experimental setup for demonstrating an arrangement of a treatment device for closing or occluding an LAA.

FIG. 10 shows an arrangement of a contact member (which can be the arrangement of the contact member 6360 disclosed above) having a lateral width or diameter that is a little less than (e.g., 10% or approximately 10% less than) an inside size or diameter of the LAA at or adjacent to an end portion of the LAA and a length along an outer surface of the contact member that is significantly less than the width or diameter of the outer surface of the contact member. FIG. 12 shows the tissue of the LAA gathered around a body portion 6362 of the implant after the implant has been rotated approximately 360°. The simulated LAA has multiple folds 6368 in it around the body portion 6362 of the implant, but has far less folds, if any, in the simulated LAA tissue around the contact member 6364. In this arrangement, folds can begin forming in the LAA tissue in this arrangement or similarly sized and configured arrangements before the contact member is rotated 180°.

In any arrangements disclosed herein, the implant can be configured so that rotating the contact member 90° or approximately 90°, or from 60° or approximately 60° to 100° or approximately 100°, or from 70° or approximately 70° to 90° or approximately 90° from a first or initial position of the contact member can cause the contact member to contact and rotate at least an end portion of the tissue of the left atrial appendage (in some arrangements, for example and without limitation, without forming any overlaps or folds or without forming a significant number of overlaps or folds in the tissue of the left atrial appendage around the contact member) and so that rotating the contact member from 90° or approximately 90° to 180° or approximately 180°, or from between 60° or approximately 60° and 100° or approximately 100° to between 160° or approximately 160° and 200° or approximately 200°, will cause the tissue of the left atrial appendage to twist around the implant at least between the contact member and the securing element. In some arrangements, the implant can be configured so that rotating the contact member past 180° or past approximately 180°, or past between 160° or approximately 160° to 200° or approximately 200°, can cause the tissue of the left atrial appendage to continue to twist and constrict around the implant mainly between the contact member and the securing element.

With some arrangements of the implant disclosed herein and in some procedures, as the tissue is wrapped around the ball, the tissue can form one or more helical patterns of tissue which can present one or more potential leak channels 6368. This potential "folding" of the tissue is illustrated in FIG. 12, as discussed above. In some arrangements or procedures, the helical patterns can present leak channels after the wrapped tissue has been collapsed in an axial direction, which can cause the tissue to loosen around the outside surface of the implant. These leak channels, if present, and the angle of the leak channels relative to the axis of the contact member and delivery catheter, can be further compressed and reduced, respectively, with axial motion to change the angle of the channels to be closer to perpendicular relative to the longitudinal axis of the contact member and the delivery catheter and/or additional rotation of the contact member to further tighten the tissue around the outside surface of the implant. The additional rotation can cause the tissue to create a tighter seal around the implant device. A nonlimiting example arrangement of steps that can be taken to achieve tighter compression of the tissue and a reduced angle of the folds relative to the longitudinal axis includes at least the following steps.

In any arrangements of the method of treatment or delivery disclosed herein, the procedure can include all or any of the following steps, in combination with any of the other steps or procedures disclosed herein. After the contact member has been advanced axially to the desired position within the LAA, the contact member can be rotated in a first direction by a first predetermined angle. For some arrangements, this can be done by rotating a second dial 8084 on the handle of the delivery catheter. In any arrangements disclosed herein, the first predetermined angle can be greater than or equal to 180 degrees, or greater than approximately 180 degrees, or can be greater than or equal to 180 degrees, or greater than approximately 180 degrees, or can be 270 degrees, approximately 270 degrees, from 200 degrees or less than 200 degrees to 330 degrees or more than 330 degrees, from 230 degrees to 300 degrees, from 250 degrees to 290 degrees, or any value or range of values in any of the foregoing ranges. The user can then proximally withdraw (e.g., pull back) the contact member 6304 by a first predetermined distance. In some arrangements, the predetermined distance can be greater than or equal to 0.5 cm, or can be 1 cm, approximately 1 cm, from 0.25 cm to 1.75 cm, from 0.5 cm to 1.5 cm, from 0.75 cm to 1.25 cm, or any value or range of values in any of the foregoing ranges.

After the contact member has been withdrawn as described above, the contact member can then be rotated in the first direction by a second predetermined angle. For example and without limitation, the second predetermined angle can be greater than or equal to 15 degrees, or can be greater than or equal to 30 degrees, or can be 65 degrees, approximately 65 degrees, from 30 degrees or less than 30 degrees to 90 degrees or more than 90 degrees, from 45 degrees to 150 degrees, from 30 degrees to 120 degrees, from 30 degrees to 90 degrees, or any value or range of values in any of the foregoing ranges. Thereafter, the securing element can be deployed and advanced toward the contact member.

Alternatively, in some arrangements, after rotating the contact member in the first direction by the second predetermined angle but before deploying the securing element, the user can proximally withdraw (e.g., pull back) the contact member by a second predetermined distance. For example and without limitation, the second predetermined distance can be 1 cm, approximately 1 cm, from 0.25 cm to 1.75 cm, from 0.5 cm to 1.5 cm, from 0.75 cm to 1.25 cm, or any value or range of values in any of the foregoing ranges. In some arrangements, the securing element can then be deployed and advanced toward the contact member.

Alternatively, after withdrawing the contact member by the second predetermined distance and before deploying the securing element, the contact member can then be rotated in the first direction by a third predetermined angle. For example and without limitation, the third predetermined angle can be 30 degrees, approximately 30 degrees, from 15 degrees or less than 15 degrees to 60 degrees or more than 60 degrees, from 15 degrees to 100 degrees, from 15 degrees to 60 degrees, from 15 degrees to 45 degrees, or any value or range of values in any of the foregoing ranges. Thereafter, the securing element can be deployed and advanced toward the contact member.

Figure 13A:
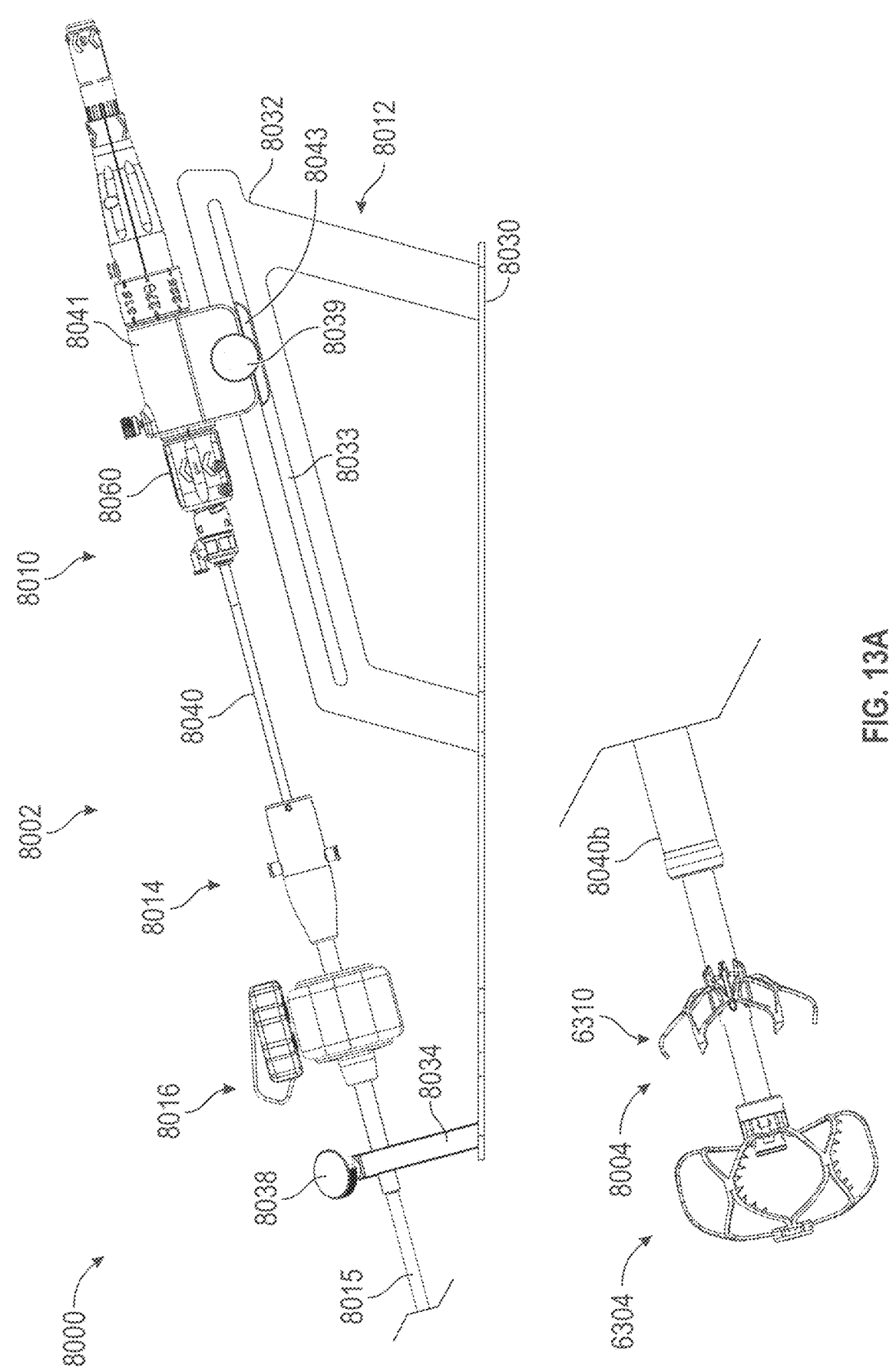
FIG. 13A shows an arrangement of a system for closing or occluding an LAA including a delivery system and an implant.
Figure 13B:
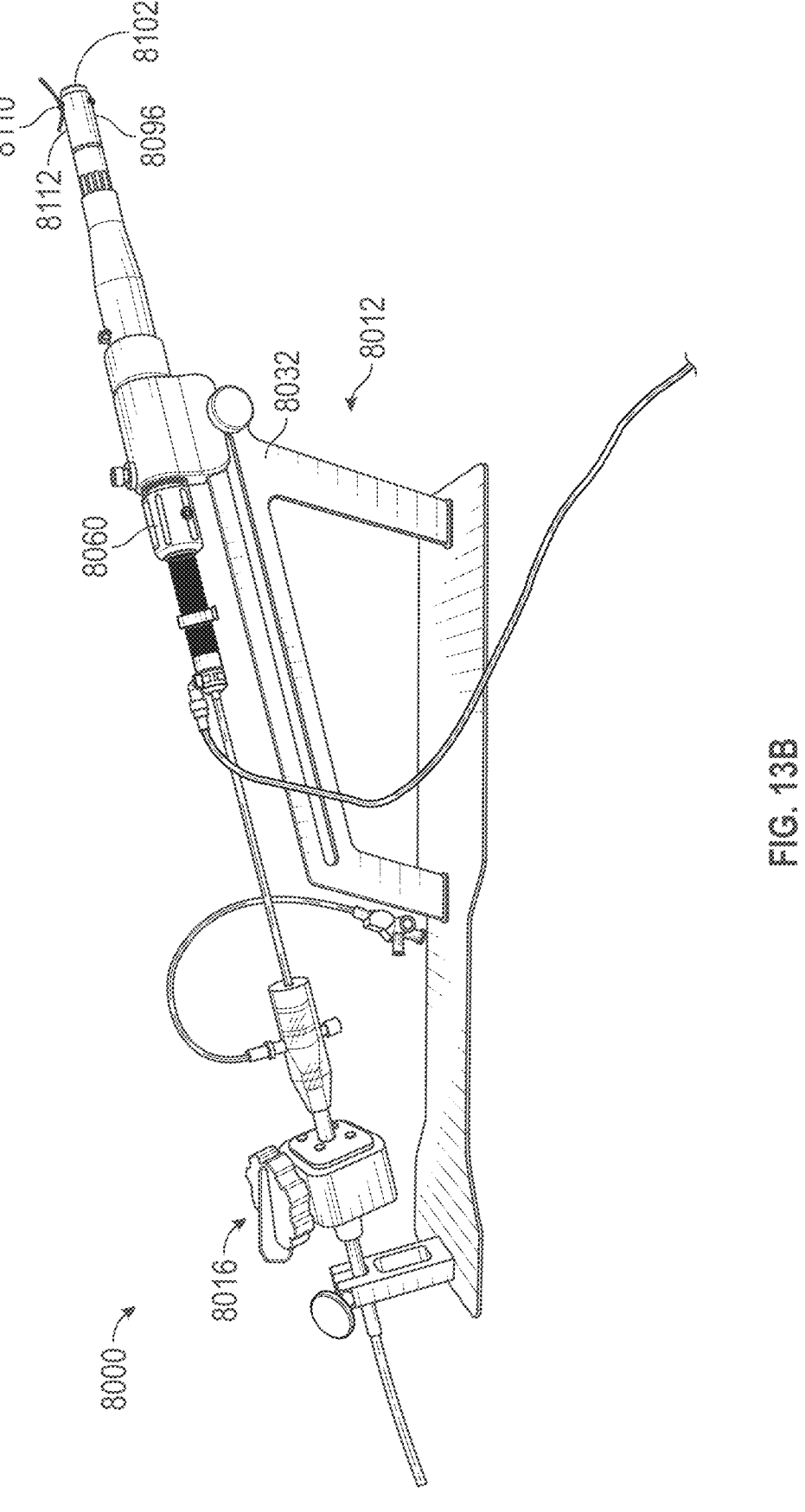
FIG. 13B shows a portion of the arrangement of a system for closing or occluding an LAA shown in FIG. 13A.

Delivery System and Method of Use of Delivery System:

FIG. 13A shows an arrangement of a system 8000 for closing or occluding an LAA including an arrangement of a delivery system 8002 and an arrangement of an implant 8004. FIG. 13B shows the arrangement of the delivery system 8002 shown in FIG. 13A, including additional components for saline and contrast media injection, etc. In any arrangements of the system 8000 disclosed herein, the implant 8004 can be the same as or can have any combination of the features as any other arrangements of the implant disclosed herein, including without limitation implant device 6102, 6302. For reference, the arrangement of the implant 6302 is illustrated in FIG. 13A. As shown in FIGS. 13A and 13B, the delivery system 8002 can include a catheter device 8010 and a support stand 8012. The delivery system 8002 can include a guide catheter 8014 and a dilator. In some arrangements, the guide catheter can optionally include a steerable sheath and the delivery system 8002 can optionally include a steering device 8016 having a steering knob 8020 to steer a steerable sheath. In other arrangements, the delivery system can include a non-steerable guide catheter.

Figures 14A, 14B:
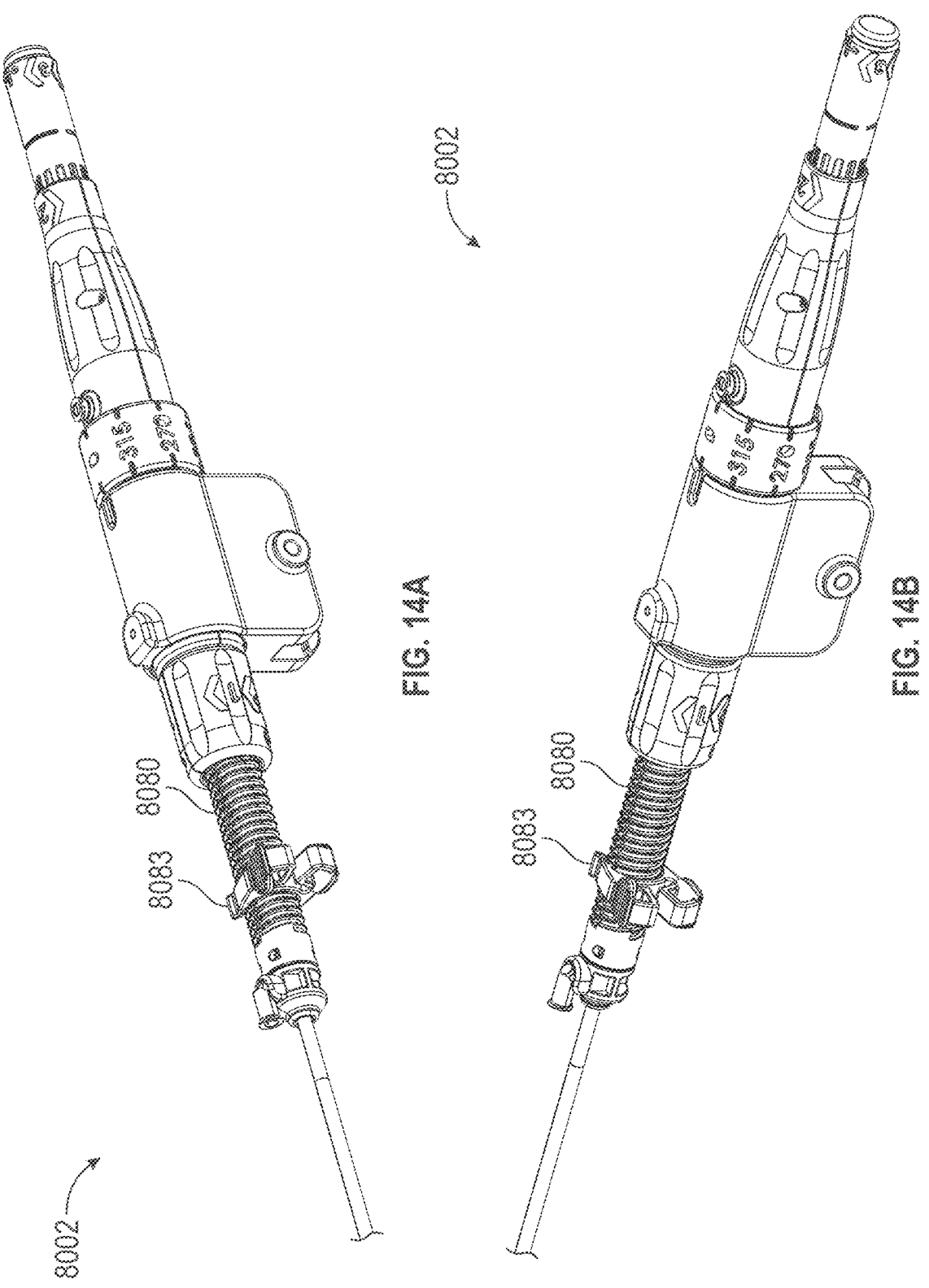
FIG. 14A shows a first isometric view of a portion of an arrangement of a delivery catheter that can be used with any arrangements of the implant disclosed herein.
FIG. 14B shows a second isometric view of the arrangement of the delivery catheter shown in FIG. 14A.
Figures 14C, 14D:
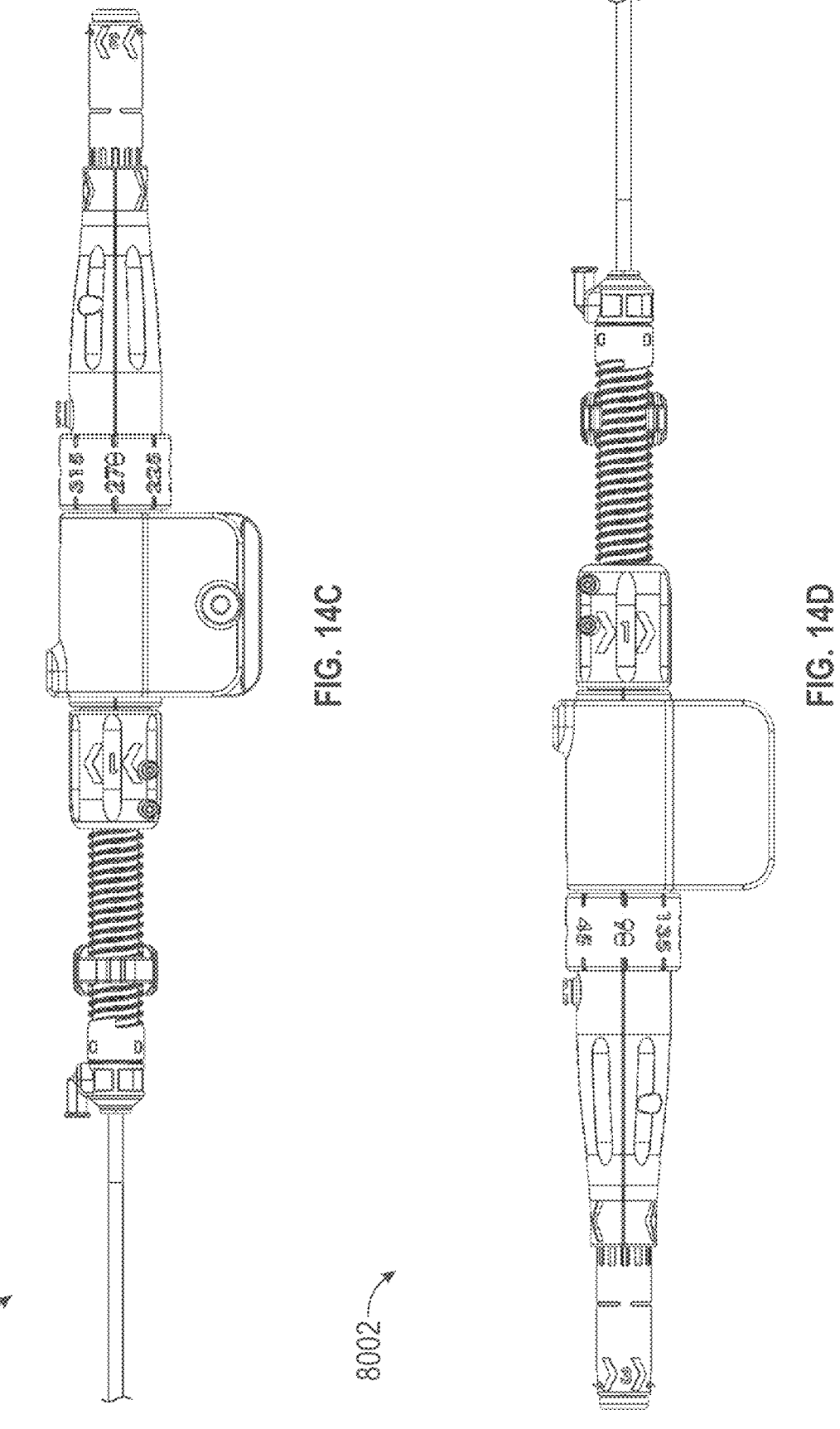
FIG. 14C shows a first side view of the arrangement of the delivery catheter shown in FIG. 14A.
FIG. 14D shows a second side view of the arrangement of the delivery catheter shown in FIG. 14A.
Figures 14E, 14F:
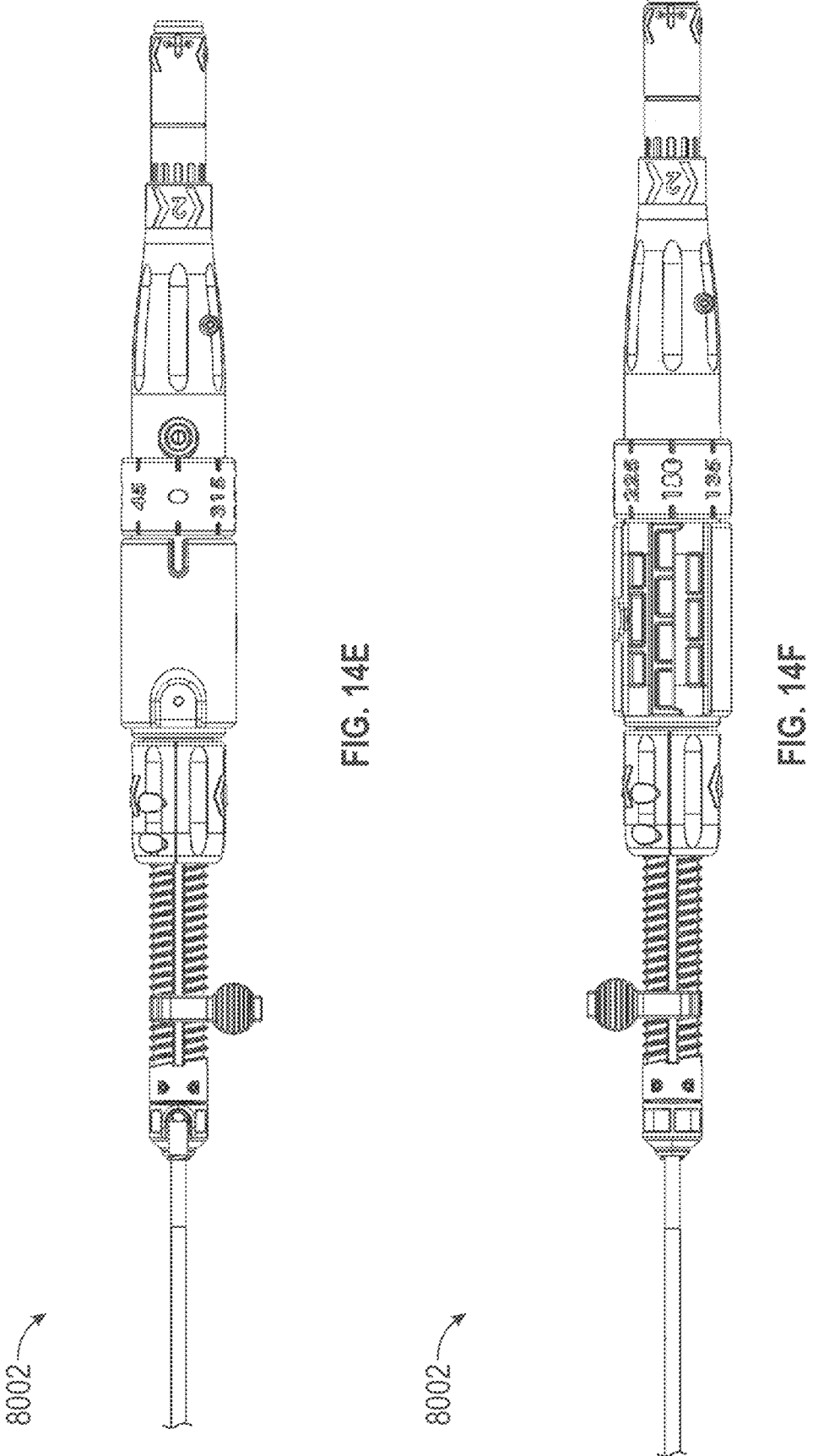
FIG. 14E shows a top view of the arrangement of the delivery catheter shown in FIG. 14A.
FIG. 14F shows a bottom view of the arrangement of the delivery catheter shown in FIG. 14A.
Figure 14H:
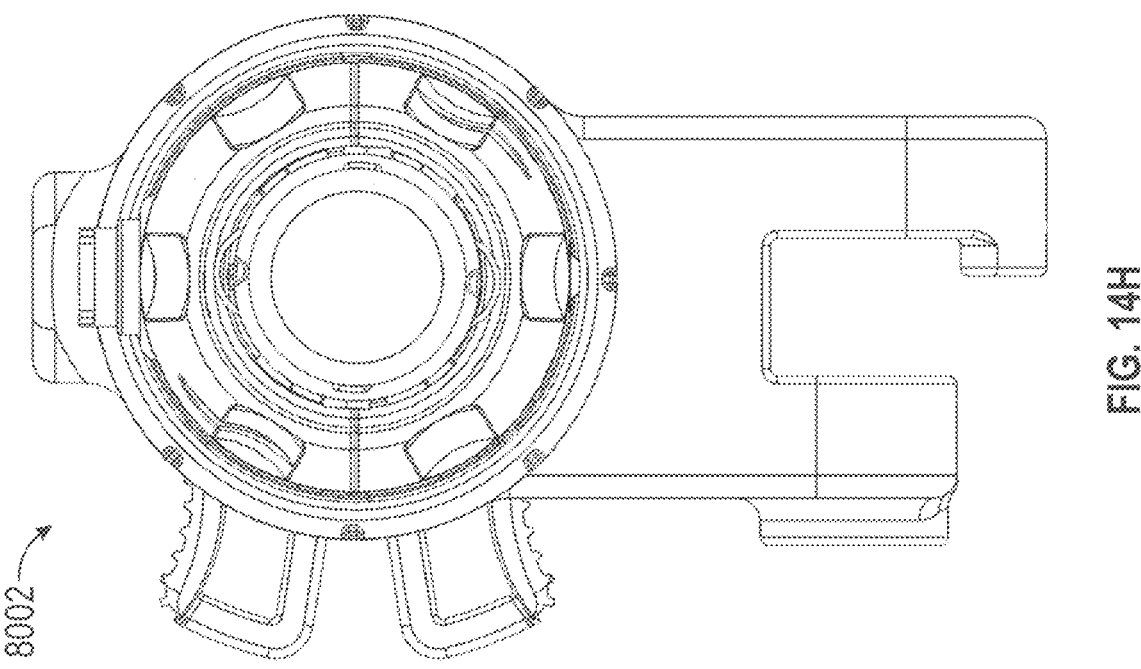
FIG. 14H shows a back view of the arrangement of the delivery catheter shown in FIG. 14A.
Figure 14G:
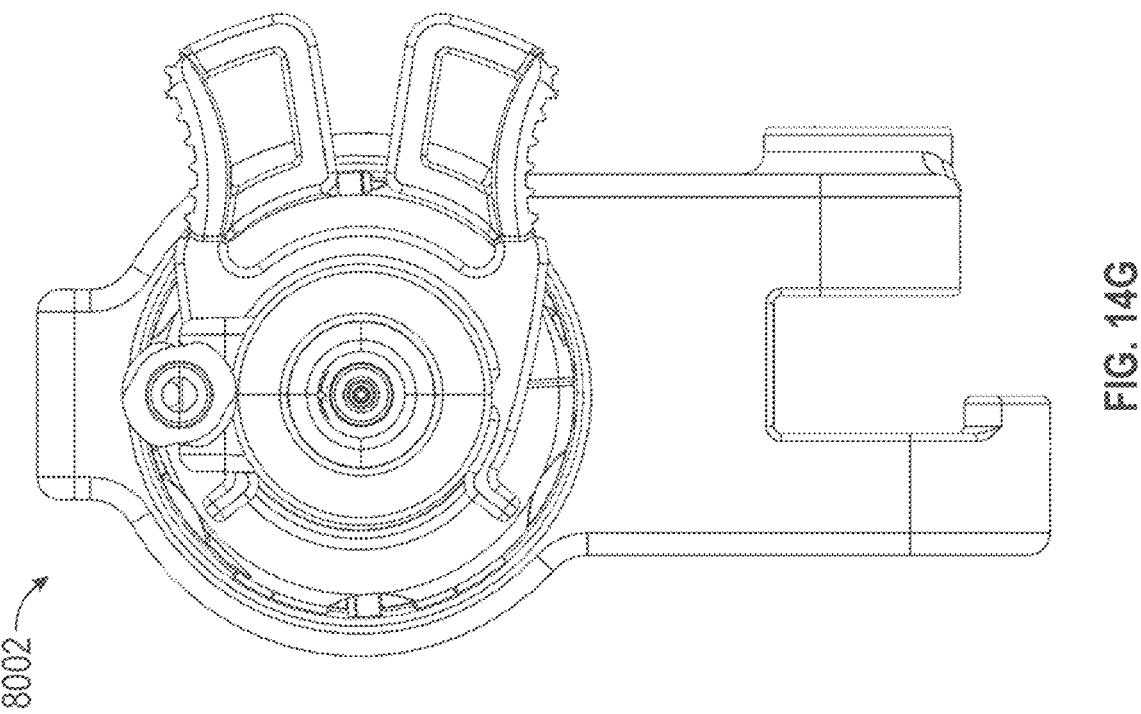
FIG. 14G shows a front view of the arrangement of the delivery catheter shown in FIG. 14A.
Figures 15A, 15B:
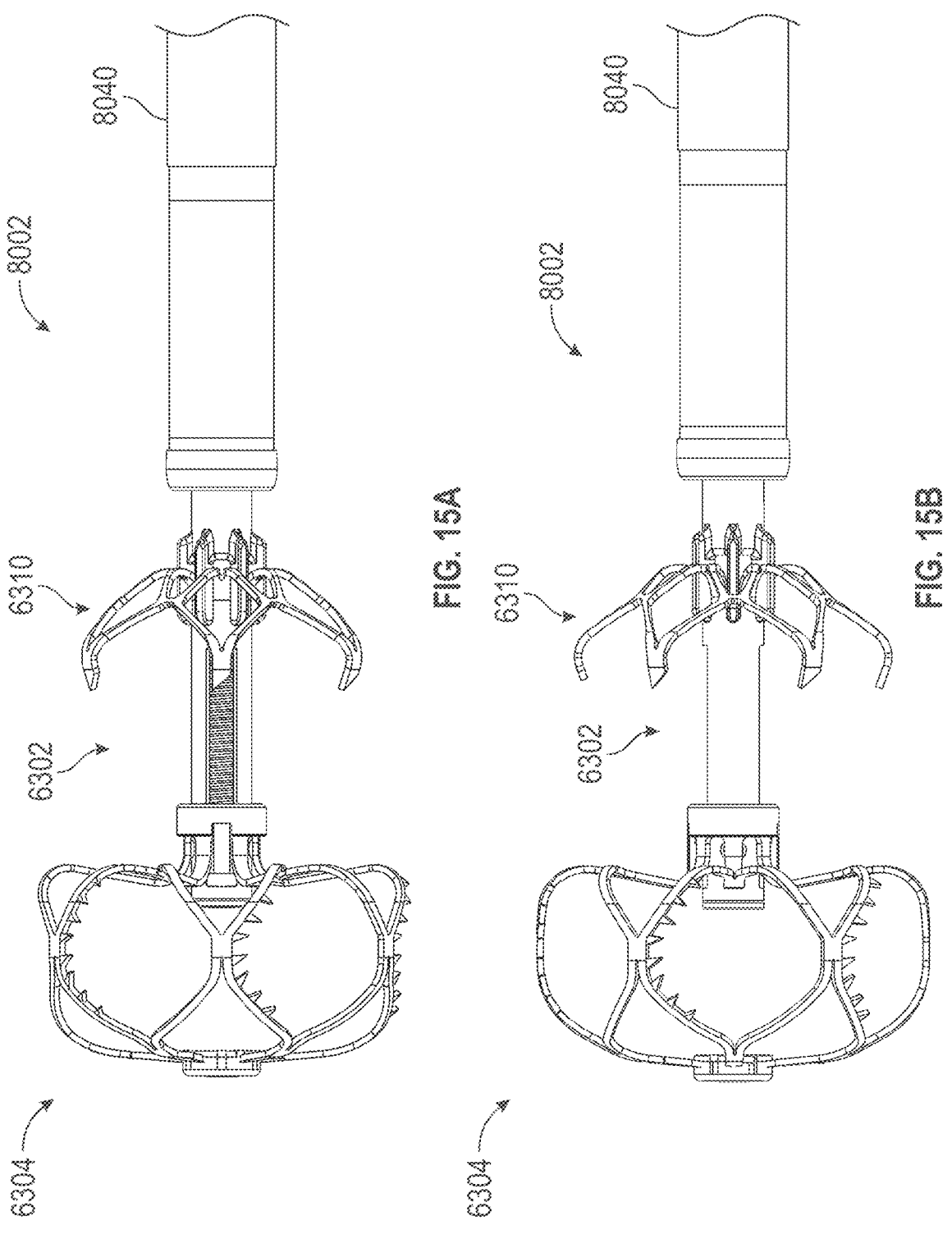
FIG. 15A shows a side view of the arrangement of the implant and distal end portion of the delivery catheter.
FIG. 15B shows a top view of the arrangement of the implant and distal end portion of the delivery catheter shown in FIG. 15A.
Figure 15C:
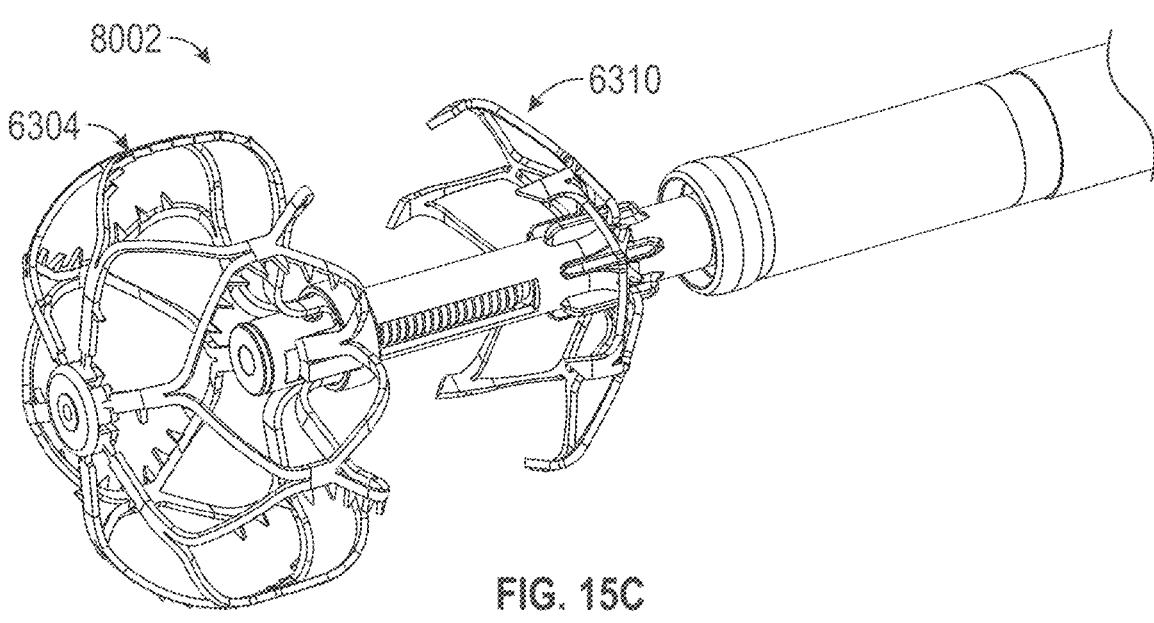
FIG. 15C shows an isometric view of the arrangement of the implant and distal end portion of the delivery catheter shown in FIG. 15A.

FIGS. 14A-14H shows a portion of an arrangement of a delivery catheter 8002 that can be used with any arrangements of the implant disclosed herein. FIGS. 15A-15C show a side view of the arrangement of the implant 6304 and distal end portion of the delivery catheter 8002, showing the outer sheath 8040 partially withdrawn and the contact member 6304 and the securing element 6310 each in an expanded state. With reference to FIG. 13A, the support stand 8012 can be positioned on a support surface, such as a bed or table, or can be positioned on a patient's body. In some arrangements, the support stand 8012 can have a low slip surface on the bottom thereof, or can be positioned on a low slip material or surface such as a low-slip mat. As will be discussed, the support stand 8012 can be used to removably support the delivery catheter 8010 (also referred to herein as a procedure catheter). Some arrangements of the support stand 8012 can include a base portion 8030, a first support portion 8032 having a slot 8033 therein, and a second support 8034 having a first locking element 8038 coupled therewith. Some arrangements of the support stand 8012 can have a scale used to measure or provide a measurement reference to a user of the system to determine how far the delivery catheter 8002 is moved along the slot 8033. The scale can provide millimeter and/or centimeter markings. For example and without limitation, this can assist the user in determining how far the implant is being moved relative to the user's anatomy during the procedure. In some arrangements, the delivery catheter 8010 can have a clamp element 8041 having a tab or projection 8043 extending therefrom that is sized and configured to extend into the slot 8033 to help maintain an alignment of the delivery catheter 8010 to the first support portion 8032.

The second support portion 8034 can be configured to support the guide catheter and dilator, and the first locking element 8038 can be selectively adjusted or tightened to secure a guide sheath of the guide catheter in a desired axial and/or rotational position after the guide sheath has been advanced to the target location using the steering device 8016. Using standard percutaneous techniques, a guidewire (e.g., a 0.035 in guidewire) and an introducer (e.g., a 6-8 Fr introducer) can be advanced into the patient's vasculature (e.g., the femoral vein, contralateral femoral artery, or a radial artery) and the guidewire and dilator can be advanced into the left atrium. An accepted or suitable transeptal procedure can be performed to achieve transeptal access.

The steerable guide catheter 8014 can be advanced over the guidewire and supported by or coupled with the second support 8034. In some arrangements, the metal tubing of the guide catheter 8014 can be secured to the second support 8034. A second locking element 8039 can be used to secure the guide catheter 8014 in the desired position relative to the guide catheter 8014 and the support stand 8012. With the dilator removed, a distal end of the outer sheath 8040 of the delivery catheter 8010 can be inserted into the guide sheath and advanced to the target location. FIG. 13 illustrates this system after the outer sheath 8040 of the delivery catheter 8010 has been advanced into the guide catheter 8014. Angiograms or other suitable imaging techniques can be performed at any step in the process for baseline purposes and for visualization during the procedure.

The outer sheath 8040 of the delivery catheter 8010 can be advanced and withdrawn axially relative to the guide sheath 8015 by sliding the delivery catheter 8010 distally and proximally, respectively, along the slot 8033 in the first support portion 8032 of the support stand 8012. By distally translating the delivery catheter 8010 toward the guide catheter 8014, the outer sheath 8040 of the delivery catheter 8010 can be advanced past a distal end of the guide sheath 8015. FIG. 13 shows the implant 8004 after the implant 8004 has been advanced past a distal end 8040b of the outer sheath 8040. As described, by proximally withdrawing the outer sheath 8040 relative to the implant 6302, the contact member 6304 and/or the securing element 6310 of the implant 6302 can self-expand, depending on how far the outer sheath 8040 is withdrawn relative to the implant 6302. The outer sheath 8040 can be advanced or withdrawn by rotating a first dial 8060 of the delivery catheter 8010 in either a first direction (e.g., clockwise) or a second direction (e.g., counterclockwise), respectively. Alternatively, in any arrangements, the contact member 6304 and/or the securing element 6310 of the implant 6302 can be advanced past a distal end 8040b of the outer sheath 8040 by distally advancing the implant 6302 relative to the outer sheath 8040. FIG. 13 shows both the contact member 6302 and the securing element 6304 advanced past the distal end 8040b of the outer sheath 8040 and in an expanded state.

Figure 17A:
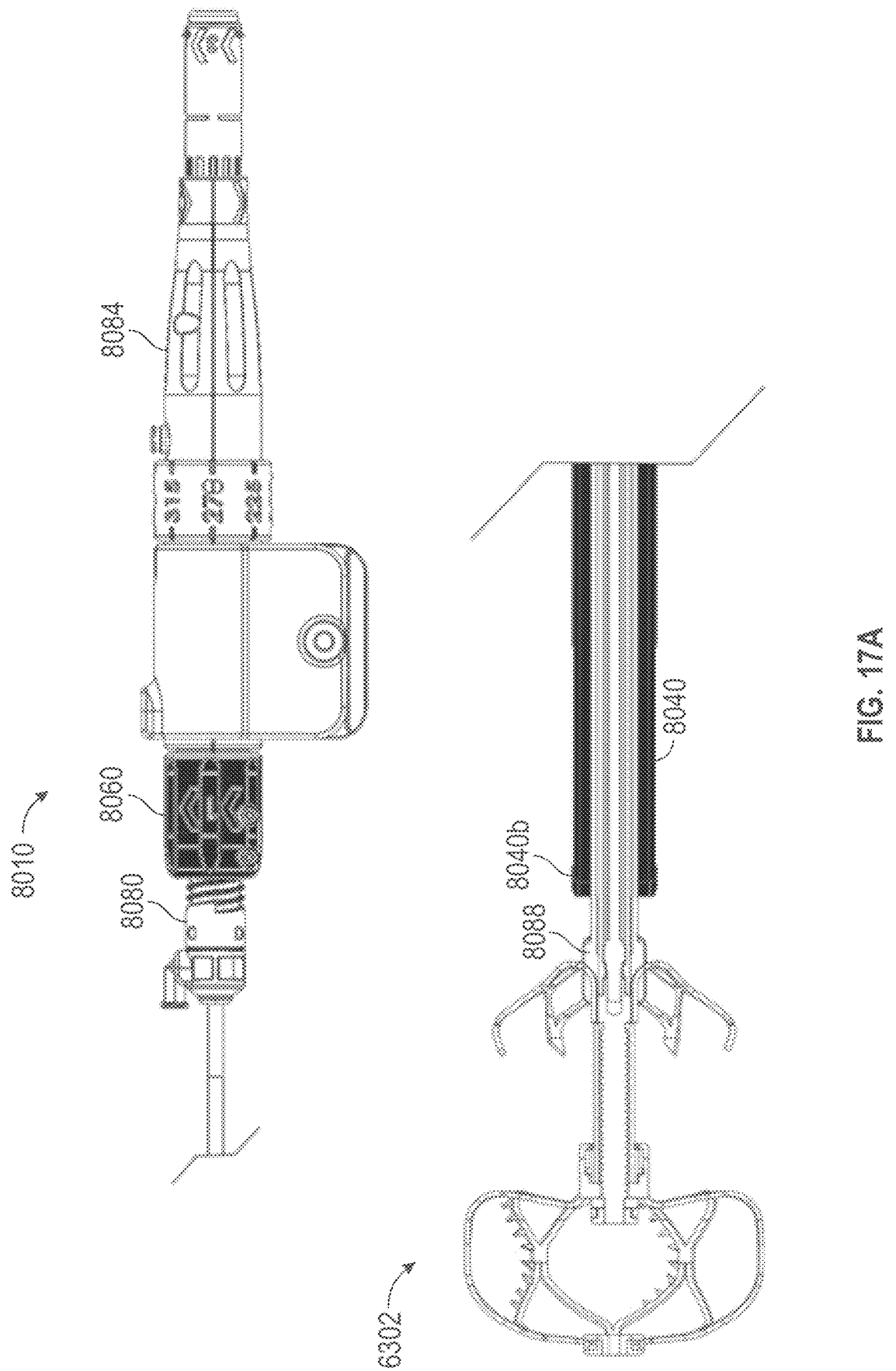
FIGS. 17A-17D show a side view of the arrangement of the delivery catheter and a partial cutaway view of the distal end portion of the outer sheath and the implant in various stages of deployment of the implant.
Figure 18A:
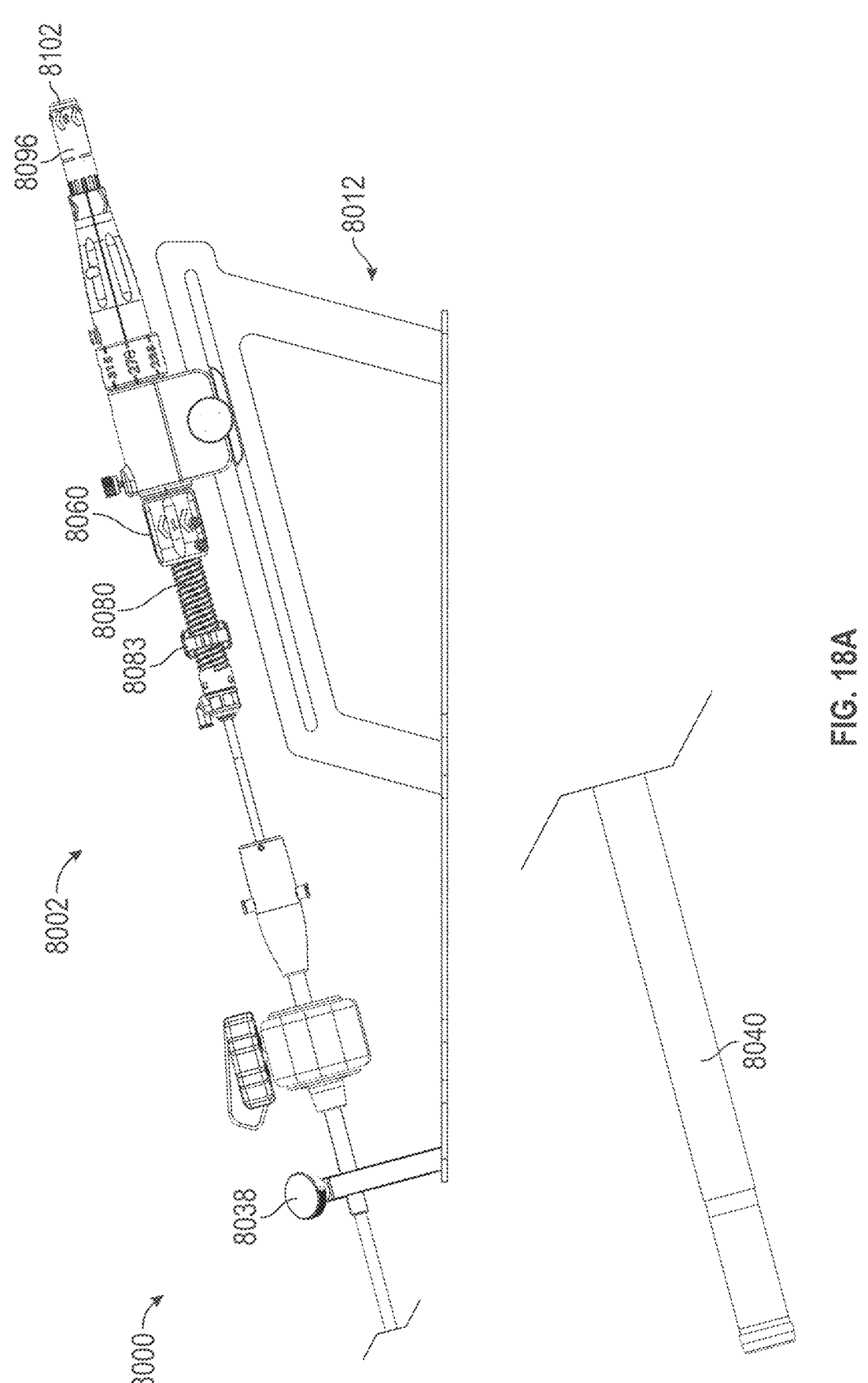
FIGS. 18A-18E show a side view of the arrangement of the delivery system and a side view of the outer sheath and the implant in various stages of deployment of the implant.
Figure 18B:
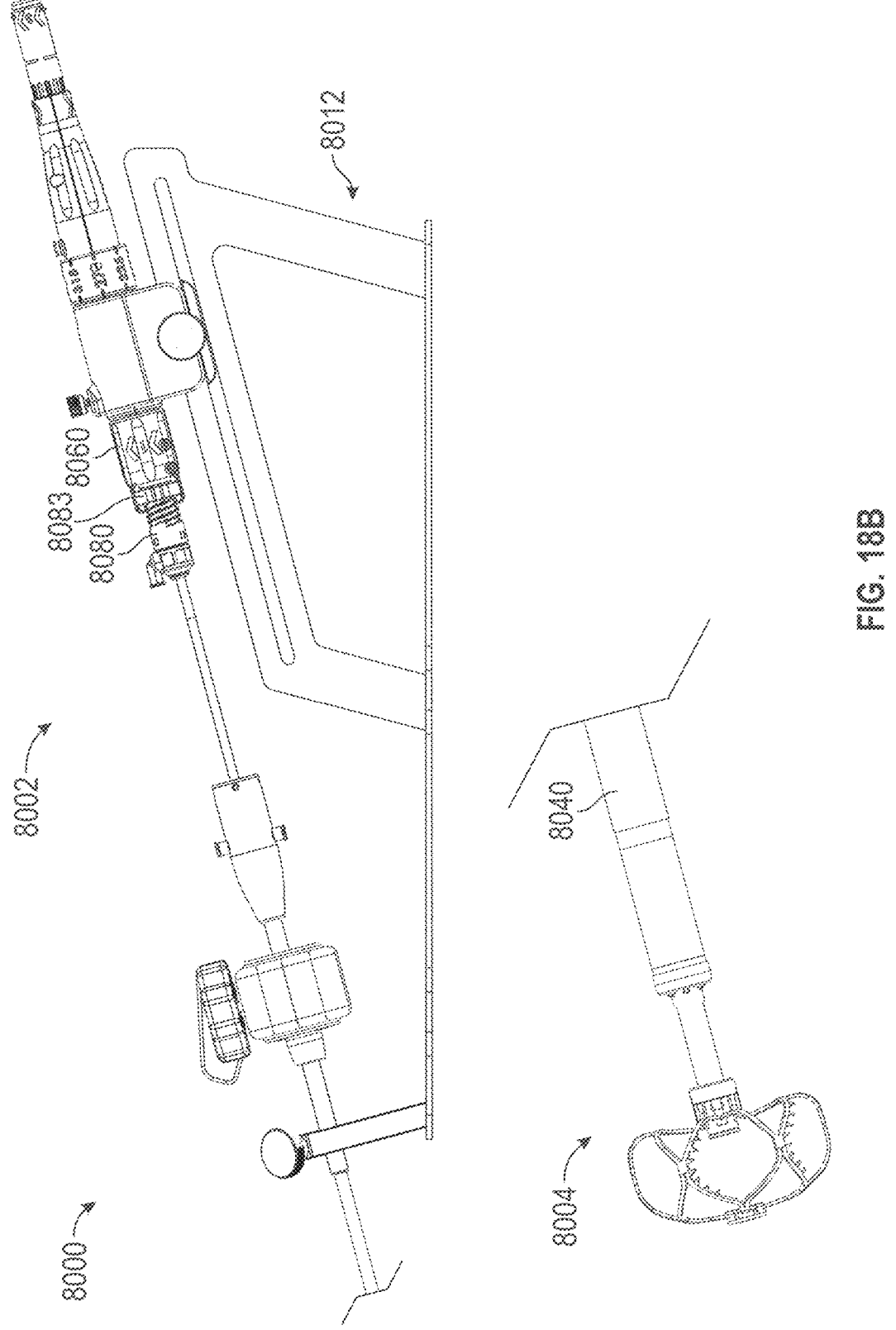

For reference, FIG. 17A illustrates the delivery system 8002 and the implant 6302, showing the outer sheath 8040 and the first dial 8060 which is rotationally coupled with the outer sheath 8040, in solid black shading. In some arrangements, the delivery system 8002 can be configured such that a rotation of the first dial 8060 in a first direction (e.g., clockwise) can cause a threaded connector 8080 that can be coupled with the outer sheath 8040 to thread into a threaded opening in the first dial 8060 (e.g., moving the threaded connector 8080 from a first position as shown in FIG. 18A to a second position as shown in FIG. 18B), thereby causing the outer sheath 8040 to move in the proximal direction. Similarly, the delivery system 8002 can be configured such that a rotation of the first dial 8060 in a second direction (e.g., counterclockwise) can cause a threaded connector 8080 that can be coupled with the outer sheath 8040 to thread out of the opening in the first dial 8060, thereby causing the outer sheath 8040 to move in the distal direction. This movement of the outer sheath 8040 can result in the distal end 8040b of the outer sheath 8040 moving relative to the implant 6302 to unrestrain the implant 6302.

Figure 16A:
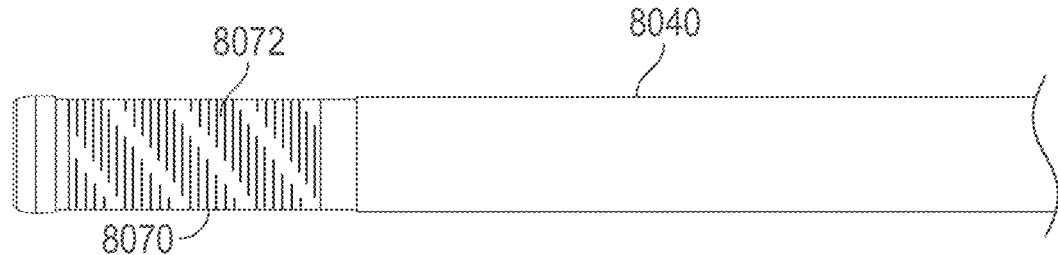
FIG. 16A shows a side view of an arrangement of a distal end portion of the outer sheath, wherein the implant is positioned within the outer sheath of the delivery catheter.
Figure 16B:
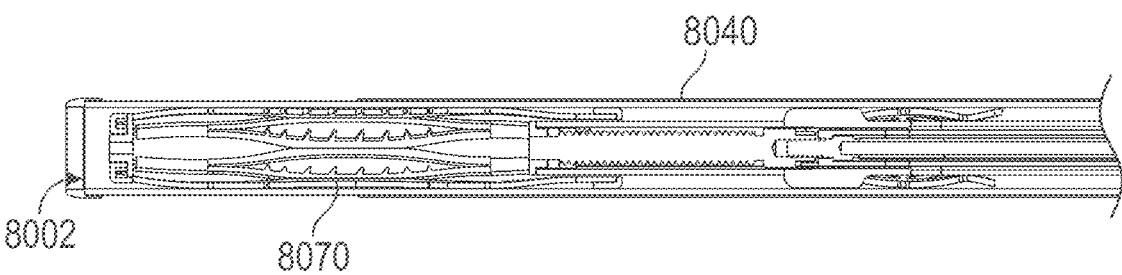
FIG. 16B shows a cutaway view of a portion of the arrangement of the distal end portion of the outer sheath shown in FIG. 16A, wherein the implant is positioned within the outer sheath of the delivery catheter.
Figure 16C:
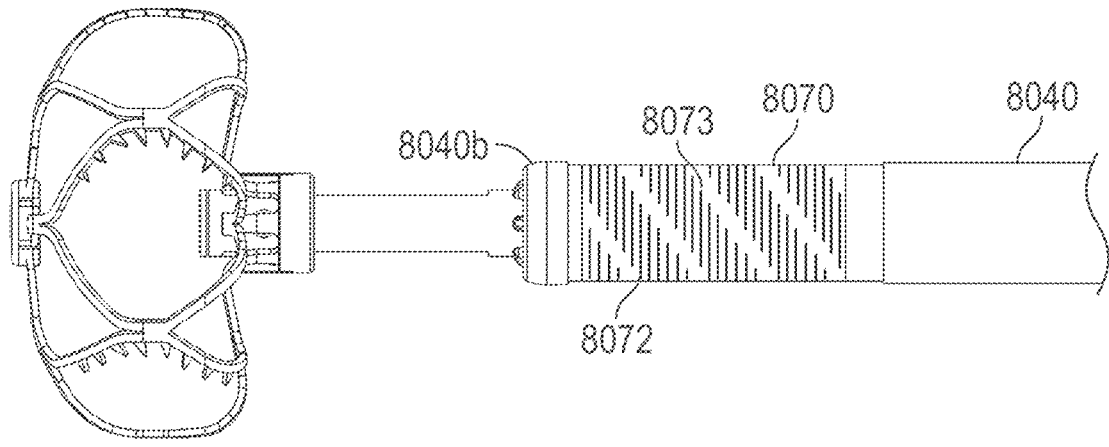
FIG. 16C shows a side view of the arrangement of the distal end portion of the outer sheath shown in FIG. 16A, wherein the implant is positioned partially past the distal end of the outer sheath such that the securing element is positioned within the outer sheath and the contact member is positioned past the distal end of the outer sheath.
Figure 16D:
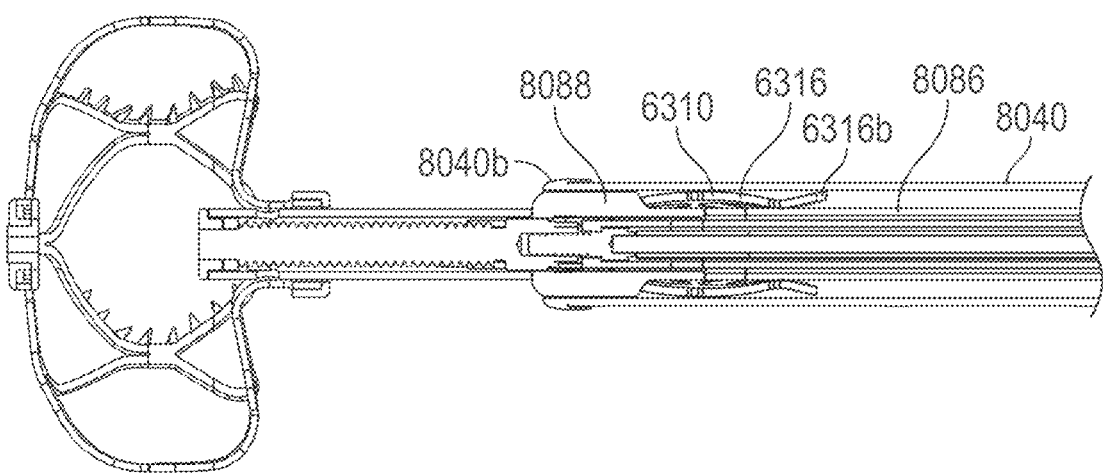
FIG. 16D shows a cutaway view of the arrangement of the distal end portion of the outer sheath shown in FIG. 16A, wherein the implant is positioned partially past the distal end of the outer sheath such that the securing element is positioned within the outer sheath and the contact member is positioned past the distal end of the outer sheath.
Figures 16E, 16F:
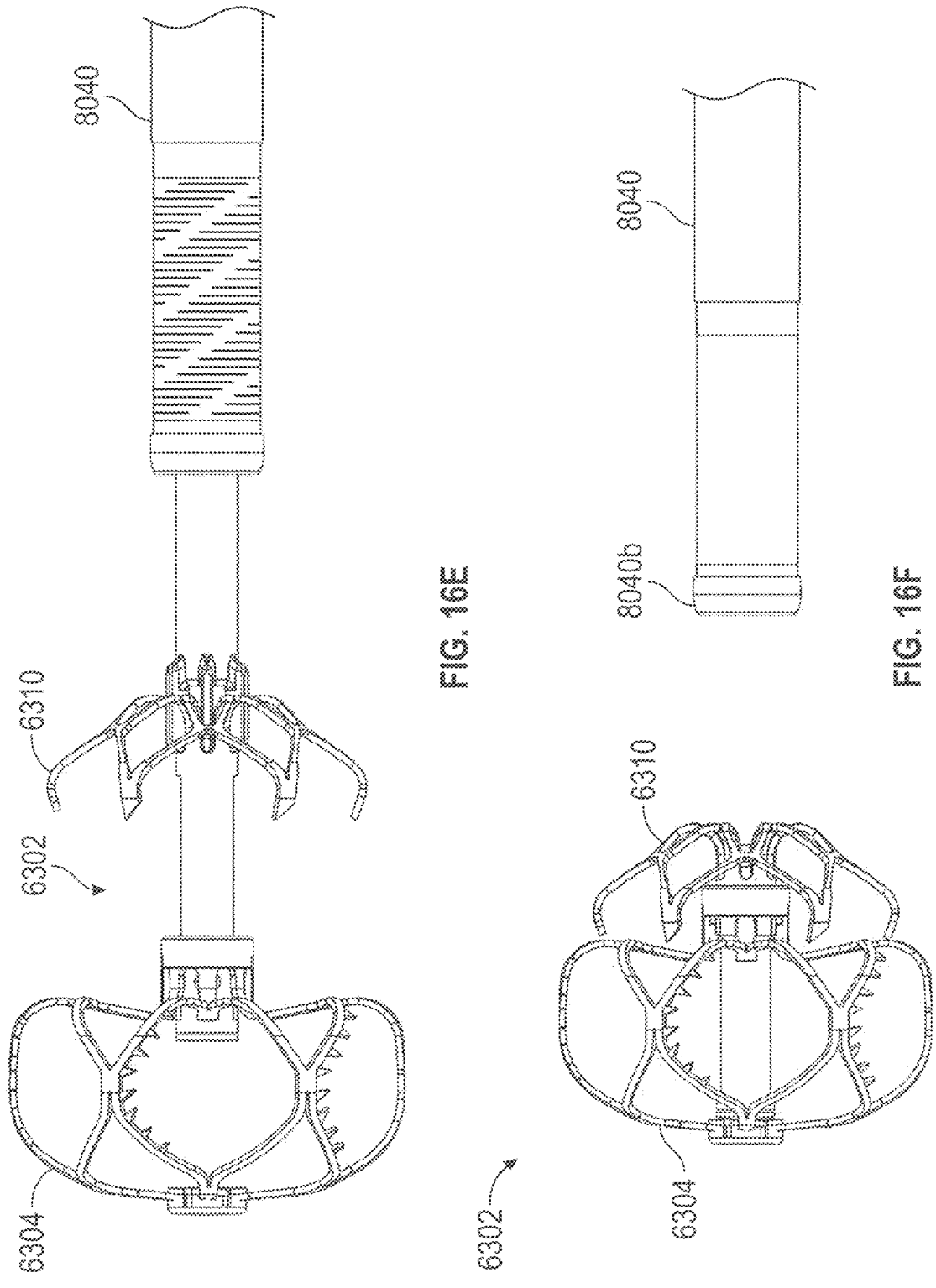
FIG. 16E shows a side view of the arrangement of the distal end portion of the outer sheath shown in FIG. 16A, wherein the implant is positioned past the distal end of the outer sheath and the contact member and the securing element are in the expanded state, but are spaced apart.
FIG. 16F shows a side view of the arrangement of the distal end portion of the outer sheath shown in FIG. 16A, wherein the implant is positioned past the distal end of the outer sheath, the contact member and the securing element are in the expanded state and are positioned close together.
Figure 18C:
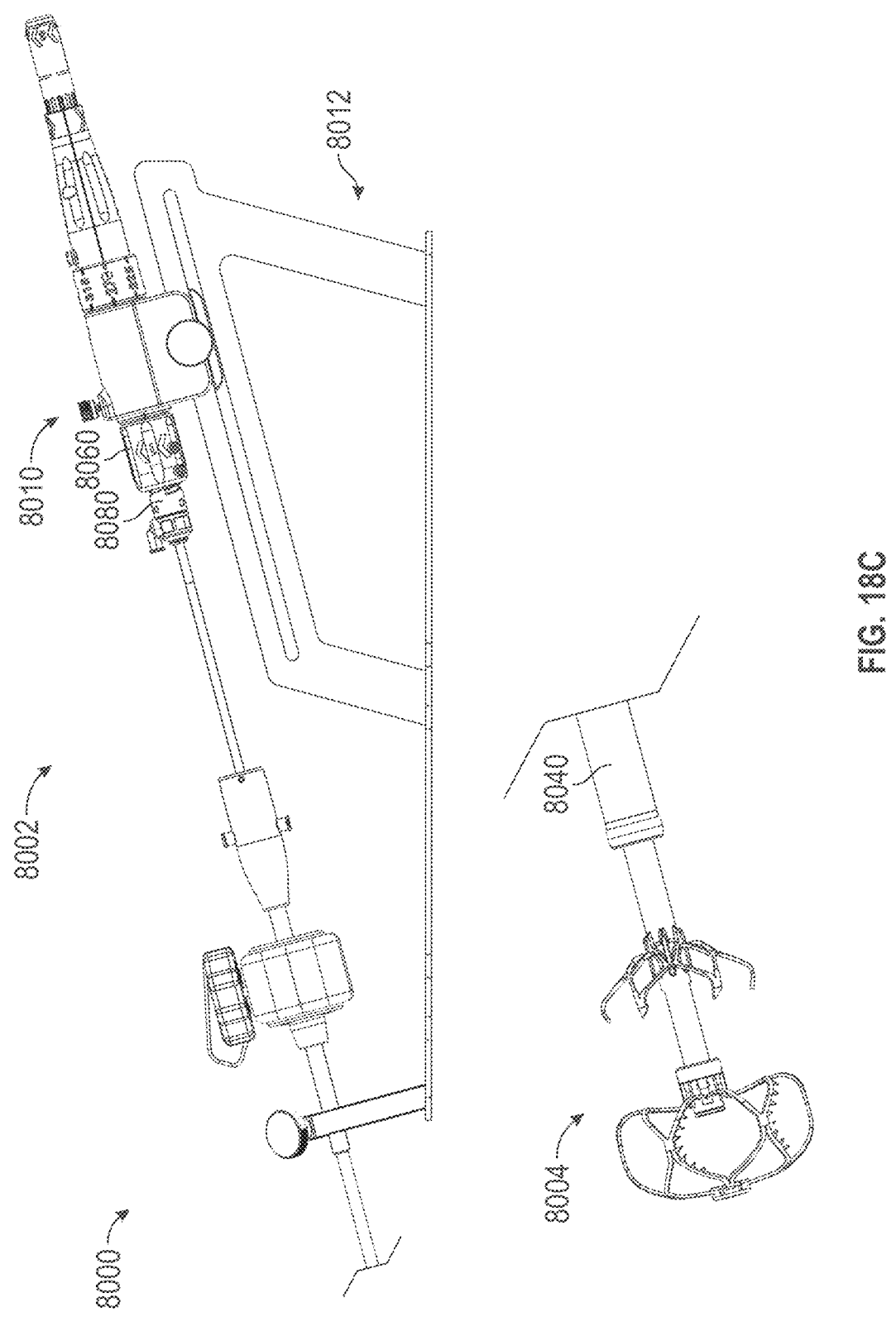
Figure 18D:
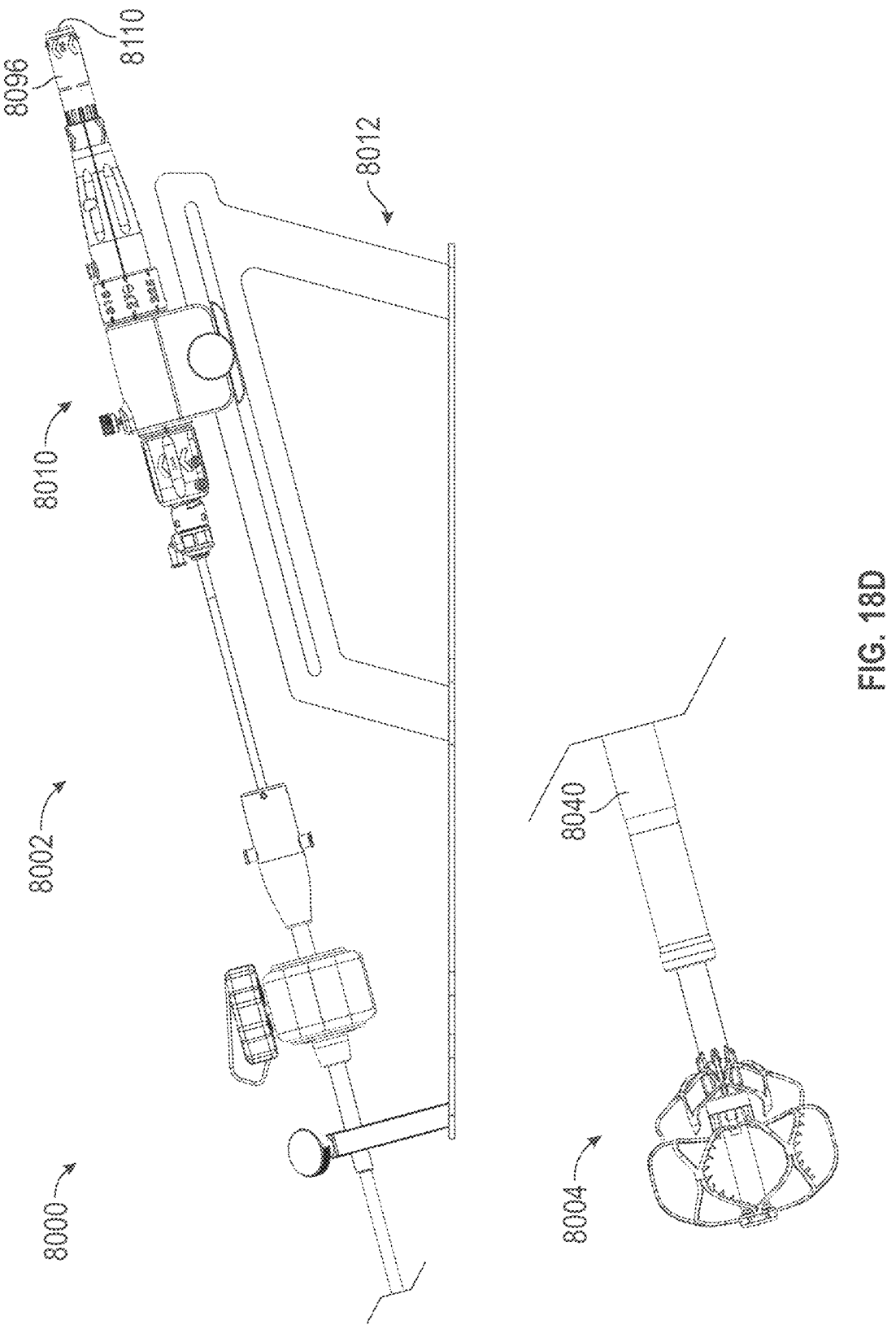

In any arrangements disclosed herein, the delivery system 8002 can be configured to selectively limit an amount of rotation of the first dial 8060 relative to the threaded connector 8080. This can be done to inhibit (e.g., prevent) the user from inadvertently releasing the securing element 6310 from the outer sheath 8040 before the user is ready to. For example and without limitation, some arrangements of the delivery system 8002 can have a stop element (e.g., a clip) 8083 that can be removably coupled with the threaded connector 8080 at any desired position on the threaded connector 8080. The stop element 8083 can be coupled with the threaded connector 8080 at a position such that, when the stop element 8083 abuts a distal end of the first dial 8060, the first dial 8060 is inhibited (e.g., prevented) from rotating further in the direction that would cause the threaded connector 8080 to thread into the first dial 8060, thereby preventing further retraction of the outer sheath 8040 until the clip is moved distally or, more commonly, removed from the outer sheath 8040. In some arrangements, stop element 8083 positioned as shown in FIG. 14A can abut the distal end of the first dial 8060 when the outer sheath 8040 is positioned as shown in FIG. 16D (where the securing element 6310 is position completely or nearly completely within the outer sheath 8040). The stop element 8083 can be removed from the threaded connector 8080 to continue rotation of the first dial 8060 in the direction that causes further retraction of the outer sheath 8040, as shown in FIG. 18C.

Figure 17B:
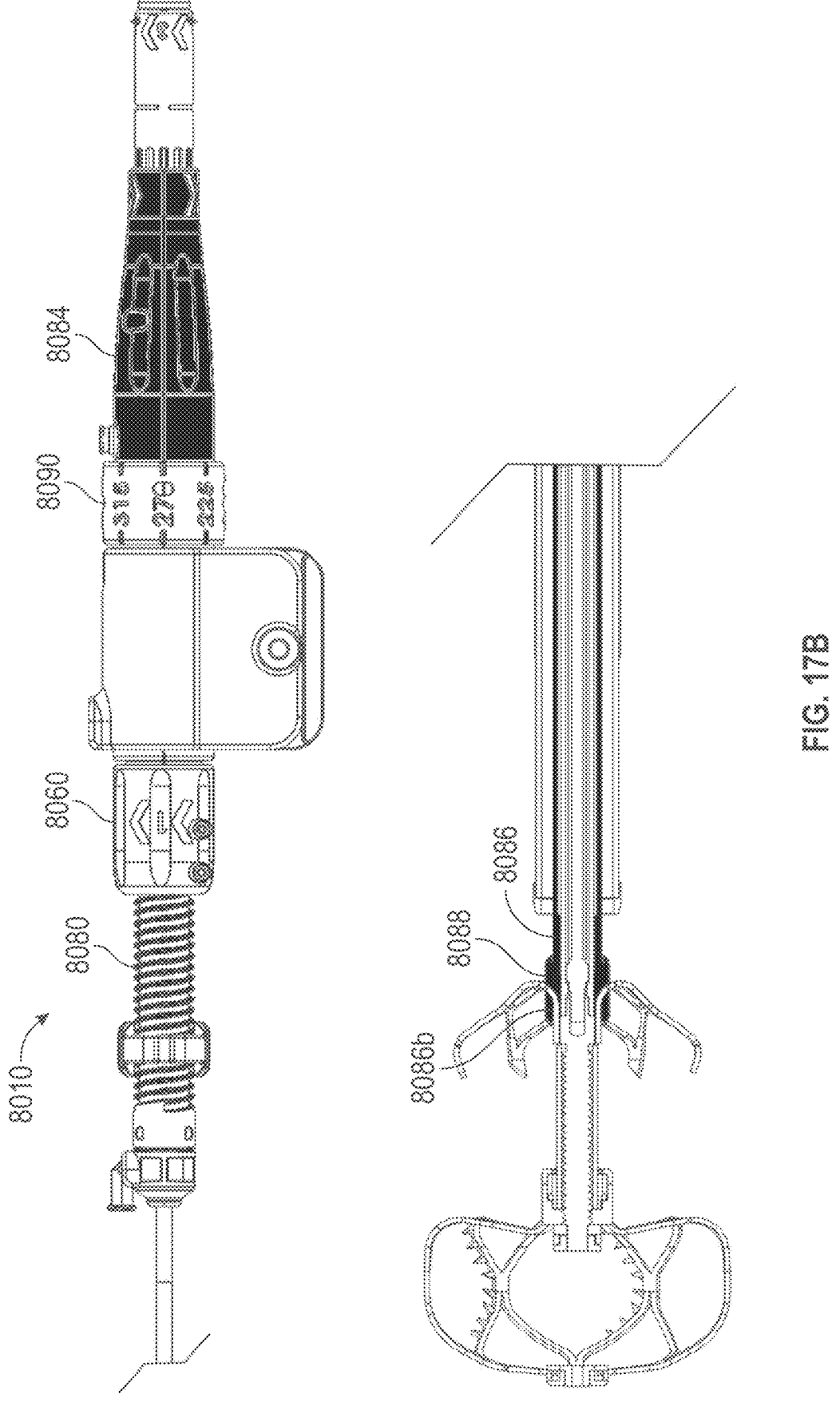

FIG. 17B illustrates the delivery system 8002 and the implant 6302, showing an inner catheter 8086 (also referred to herein as a first inner catheter or inner catheter member) having one or a plurality of fins 8088 at a distal end 8086b of the inner catheter 8086 (also referred to herein as an inner tube), and a second dial 8084 which is rotationally coupled with the inner catheter 8086, in solid black shading. An axial translation in a first direction and/or a rotation of the second dial 8084 (along with the entire handle of the delivery system 8002) in a first direction will cause a commensurate axial translation and/or rotation of the inner catheter 8086, respectively, which will cause a commensurate axial translation and/or rotation of the implant 6302, respectively, when the implant 6302 is engaged with the inner catheter 8086. In some arrangements, the inner catheter 8086 can have one or more or a plurality of fins 8088 extending in a radial direction at a distal end 8086 of the inner catheter 8086. The fins 8088 can be configured to fit between the struts 6316 of the securing element 6310 at least when the securing element 6310 is in a restrained position within the outer sheath 8040. In this arrangement, the user can rotate the contact member and/or the securing element by rotating the second dial 8084 and, hence, the inner catheter 8086.

In some arrangements, the delivery system 8002 can have an angle gauge 8090 configured to rotate with the second dial 8084 so that a user can measure or track an angle of rotation of the second dial 8084. This can provide visual feedback to the user of generally how much the implant is being rotated during the procedure. In some arrangements, the angle gauge 8090 can be configured to be adjustable or selectively rotatable relative to the second dial 8084. For example and without limitation, in some arrangements, the user can disengage the coupling mechanism that selectively rotationally couples the angle gauge 8090 to the second dial 8084 so that the user can rotate the angle gauge 8090 relative to the second dial 8084—e.g., to reset the angle gauge 8090 to a zero reading relative to an indicator on the delivery system 8002. In some arrangements, the coupling mechanism can be a ball and detent or detents, or a plurality of balls and detents, that can be configured to bias the angle gauge 8090 to be rotationally coupled with the second dial 8084 but can be overcome by exerting a threshold torque on the angle gauge 8090 relative to the second dial 8084. The angle gauge 8090 can have readings at 45 degrees, or 30 degrees, or 15 degrees. The optional ball and detent mechanism can be configured to have a detent every 45 degrees, or 30 degrees, or 15 degrees that can be sized and configured to receive the ball so that the user can selectively rotate the angle gauge 8090 relative to the second dial 8084 and then recouple the angle gauge 8090 to the second dial 8084 at such increment (e.g., at 45 degrees, or 30 degrees, or 15 degrees). Other selective rotational coupling mechanisms can also be used to bias or selectively rotationally couple the angle gauge 8090 to the second dial 8084.

Figure 17C:
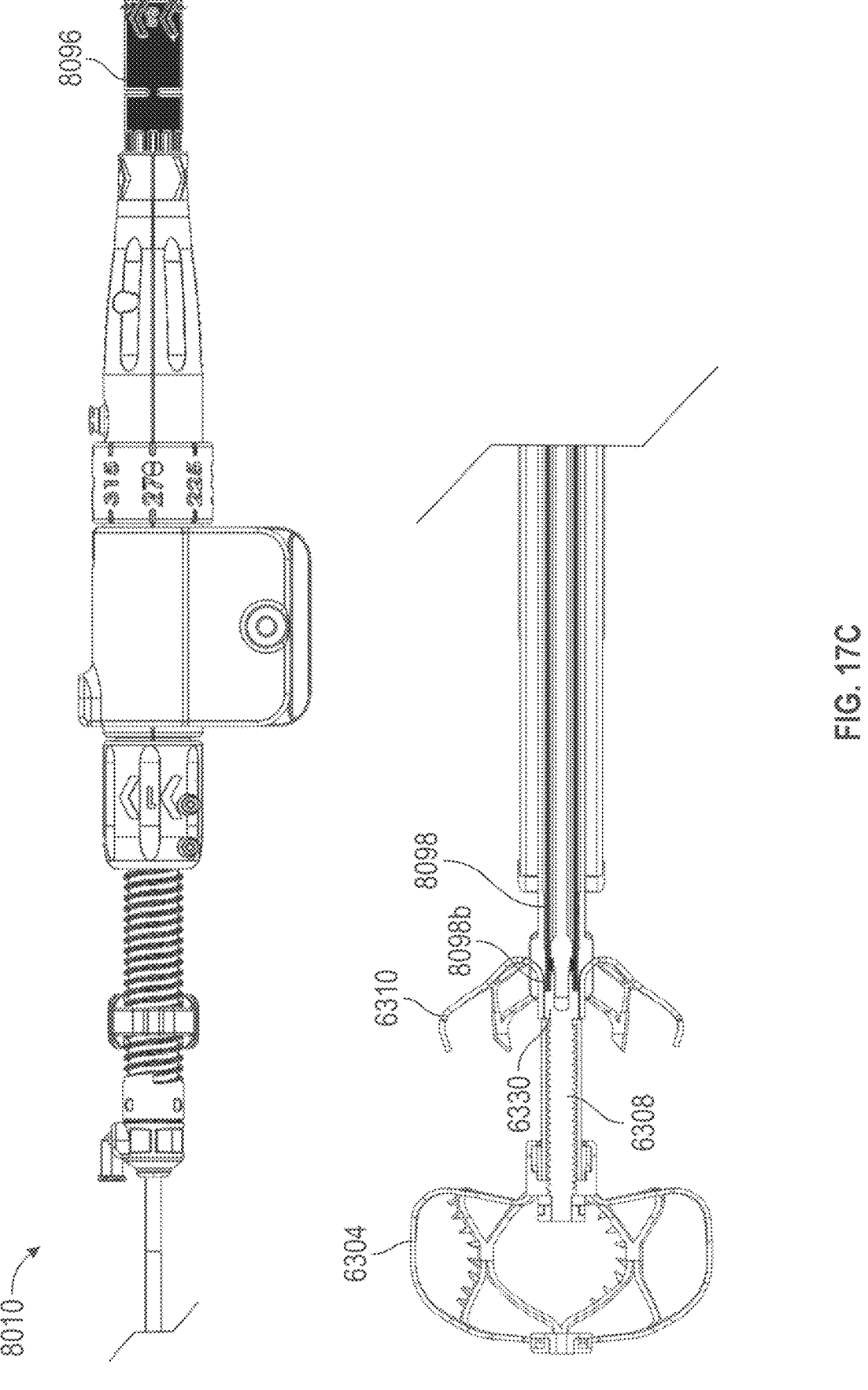

With reference to FIG. 17C, after the contact member has been rotated and/or translated as desired such that the tissue of the LAA and/or the LA has constricted around the implant, the user can then advance the securing element 6310 toward the contact member 6304 by rotating a linking element 8096 (also referred to herein as a sleeve) of the delivery system 8002. The sleeve 8096 can be rotationally coupled with or otherwise keyed with a third dial 8097 (not shown in FIG. 17C) and a fourth dial 8102 with one or a plurality of splines, teeth, and/or other engagement features when the sleeve 8096 is in a first position (as shown in FIG. 17C). The third dial 8097 can be axially and rotationally coupled with a second inner catheter 8098 (also referred to herein as a second inner catheter member) positioned inside the inner catheter 8086. The sleeve 8096 and the second inner catheter 8098 are shown in solid black shading in FIG. 17C for reference.

Figure 18E:
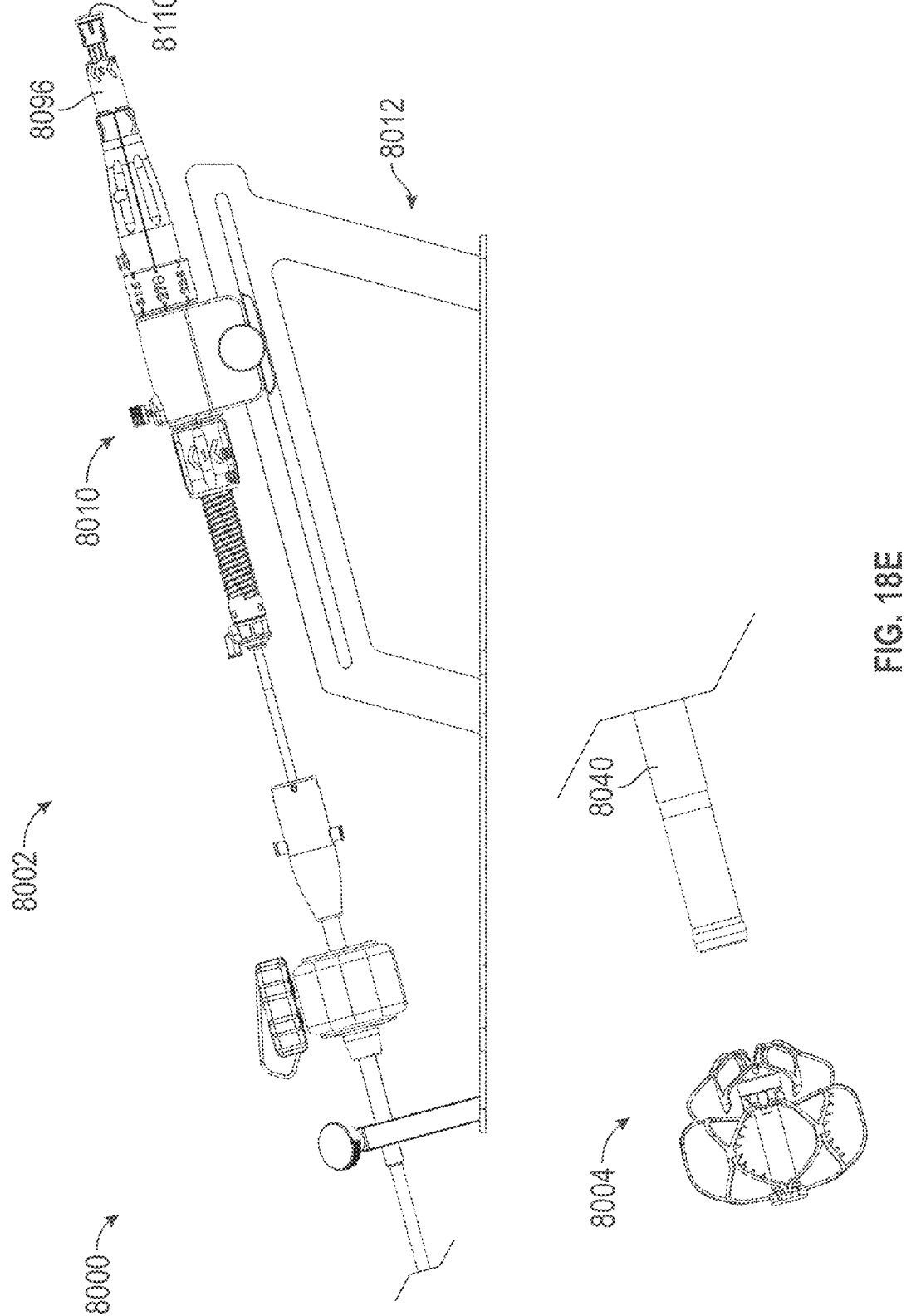

A distal end 8098b of the second inner catheter 8098 can be rotationally coupled with the head 6330 that is coupled with the threaded shaft 6309 of the retention element 6308 when the distal end 8098b of the second inner catheter 8098 is engaged with the head 6330 such that, when the sleeve 8096 is in the first position, a rotation of the sleeve 8096 will cause the simultaneous and equal rotation of the third dial 8097 and the second inner catheter 8098 so as to rotate the retention element 6308. In this state, a rotation of the sleeve 8096 in a first direction can cause the retention element 6308 to rotate in a first direction and move the securing element 6310 toward the contact member 6304 (e.g., to a position as shown in FIG. 18E) and a rotation of the sleeve 8096 in a second, opposite direction can cause the retention element 6308 to rotate in a second direction and move the securing element 6310 away from the contact member 6304. By rotating the sleeve 8096 in the first direction, the user can advance the securing element 6310 toward the tissues of the LAA and/or LA that has been constricted by the rotation of the contact member 6304 to bias the tissue of the LAA and/or the LA in the closed or occluded state.

Some arrangements of the delivery device 8002 can have a fourth dial 8102 that can be used to release the implant from the delivery catheter 8002, as shown in FIG. 18E. The fourth dial 8102 can be positioned at a proximal end of the handle portion of the delivery catheter 8002 and can be coupled with an inner core 8106 (also referred to herein as a third inner catheter member) that is positioned inside of the second inner catheter 8098. The fourth dial 8102 and the inner core 8106 are shown in solid black shading in FIG. 17D for reference. The inner core 8106 can have a threaded end portion 8108 having external threads thereon that can be threadedly engaged with a threaded opening 6315 having internal threads. The threaded end portion 8108 can be used to selectively couple the inner core 8106 with the retention element 6308. The threaded portion 8108 can be removed from the retention element 6308 by rotating the threaded portion 8108 relative to the retention element 6308 in a first direction (e.g., counter clockwise) that causes the threaded portion 8108 to unthread from the retention element 6308. In some arrangements, the retention element 6308 can be held in a fixed rotational position with the inner catheter 8086, e.g., while the fourth dial 8102 is turned to remove the inner core 8106 from the retention element 6308. Thus, in some arrangements, when the user is ready to release the implant from the delivery catheter, the user can unthread the threaded portion 8108 from the retention element 6308 and then axially withdraw the entire 8002, with the implant remaining in the deployed position within the LAA/LA.

Figure 17D:
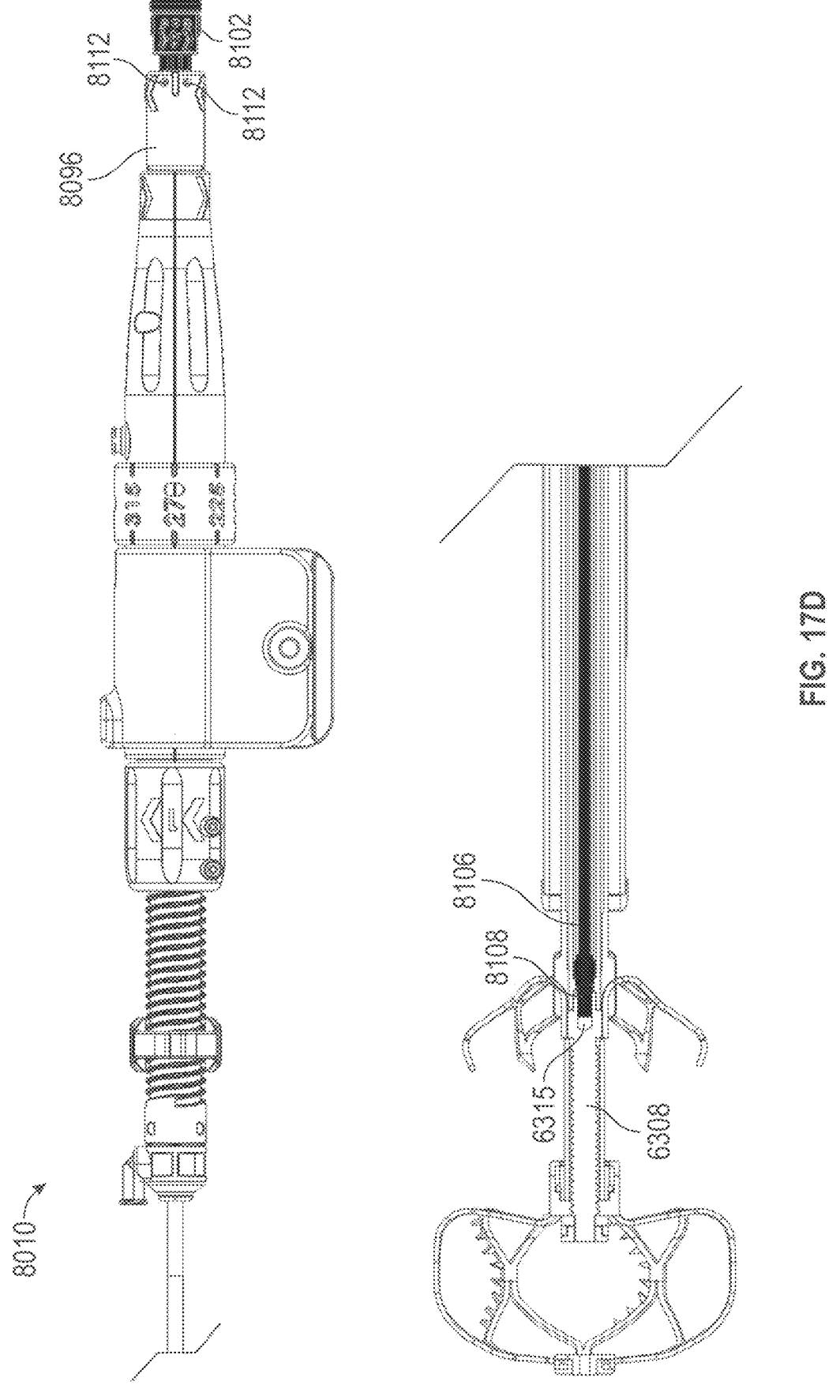

With reference to FIG. 17D, in some arrangements, the sleeve 8096 can be selectively axially coupled with the fourth dial 8102. The sleeve 8096, when axially coupled with the fourth dial 8102, can prevent the independent rotation of the fourth dial 8102 relative to other components of the delivery system 8002, including without limitation the third dial 8097. In some arrangements, the sleeve 8096 can be rotationally coupled with a fourth dial 8102 with one or a plurality of splines, teeth, and/or other engagement features when the sleeve 8096 is in the first position (as shown in FIG. 17C)—e.g., when the sleeve 8096 is overlapping the fourth dial 8102 sufficient to engage the complementary splines, teeth, and/or other engagement features of the sleeve 8096 and the fourth dial 8102. When the sleeve 8096 is slid in an axial position so that the splines, teeth, and/or other engagement features of the sleeve 8096 are not engaged with the complementary splines, teeth, and/or other engagement features of the fourth dial 8102 (e.g., to a second position, as shown in FIG. 17D), the fourth dial 8102 can then be rotated in the first direction to remove the threaded portion 8108 from the retention element 6308, as discussed above.

In some arrangements, the sleeve 8096 can be selectively inhibited (e.g., selectively prevented) from moving axially from the first position of the sleeve 8096 to the second position of the sleeve 8096. For example and without limitation, a removable locking element 8110 can be used to selectively inhibit the sleeve 8096 from moving axially from the first position to the second position. In some arrangements, the removable locking element 8110 can be a suture, as shown in FIG. 13B that passes through one, two, or more openings 8112 in the sleeve 8096 that are aligned with one, two, or more openings in the fourth dial 8102 that are aligned with the one, two, or more openings 8112 in the sleeve 8096 when the sleeve 8096 is in the first position. In this state, the removable locking element 8110 prevents the axial movement of the sleeve 8096 relative to the fourth dial 8102. In this state, with the sleeve 8096 coupled with the fourth dial 8102, the delivery system 8002 can therefore prevent the user from inadvertently releasing the implant from the delivery catheter. In some arrangements, the user can remove the removable locking element 8110 to permit the sleeve 8096 to be moved to the second position of the sleeve 8096 and to thereafter rotate the fourth dial 8102 to release the implant. For example and without limitation, where the removable locking element 8110 is a suture, the user can cut and withdraw the suture from the delivery device 8002, move the sleeve 8096 in the axial direction to the second position, and then rotate the fourth dial 8102 to release the implant from the delivery system 8002.

FIGS. 16A-16D show an arrangement of a distal end portion of the outer sheath 8040. In any arrangements of the system, the outer sheath 8040 can be used to restrain the implant, including the contact member and the securing element. Additionally, in any arrangements disclosed herein, the contact member and the securing element can be self-expanding such that when the contact member and/or the securing element are advanced past a distal end of the outer sheath, the contact member and the securing element can each expand from a first state to a second, enlarged or expanded state. In the initial configuration of some arrangements of the system 8000, to ensure that the arms or struts of the securing element can expand and ensure that the distal and portions of the struts of the securing element are not within tissue that has constricted or collapsed around the implant or the outer sheath, the securing element can be arranged in the system so that the distal end portions of the arms or struts are pointing in the proximal direction when the securing element is restrained within the outer sheath in the initial configuration. Any arrangements of the implant can be configured such that, after the contact member and the securing element have been expanded to the second, expanded state, the contact member and/or the securing element can be collapsed or returned to the collapsed state within the outer sheath by distally advancing the outer sheath. In this configuration, distally advancing the outer sheath can cause the securing element to collapse such that the distal end portions of the struts or arms of the securing element are pointing in a distal direction. Further advancement of the outer sheath can also cause the distal end of the outer sheath to move against the contact member and cause the contact member to collapse to the initial collapsed state within the outer sheath. This can be beneficial for recapturing the implant or repositioning the contact member and/or the securing element.

In some arrangements, the distal end portion of the outer sheath 8040 can have a distal section 8070 having a plurality of openings 8072 therein. In some arrangements, the openings 8072 can be laser cut into the distal section 8070. In some arrangements, the openings 8072 can be 0.001 inch in width, or approximately 0.001 inch in width. The openings 8072 can be configured to permit a fluid (e.g., a contrast media) to flow therethrough when a pressure differential between the inside the outer sheath and the outside of the outer sheath reach a predetermined or threshold value. Additionally, the openings 8072 can be positioned to permit a user to determine a location of the tissue of the LAA and/or the LA that has been constricted by the implant 6302. For example and without limitation, when the implant has been rotated and the tissue of the LAA and/or the LA has been wrapped around a portion of the implant, it is helpful for the user to determine where such wrapped tissue is positioned or where an end portion of the tissue is on the implant. The tissue may be difficult or impossible to view in fluoroscopy. In this situation, contrast medial can be advanced through the outer sheath 8040 and through the openings 8072 when the openings 8072 are not covered by tissue. When the tissue covers the openings 8072, the tissue can block a passage of or inhibit a passage of a fluid (e.g., the contrast media) through the openings 8072. Therefore, if contrast media flows through the openings 8072, the openings 8072 that the contrast media flows through are not covered by tissue. In some arrangements, the openings 8072 can in this manner be used to determine generally a position of the tissue relative to the distal end 8040*b* of the outer sheath 8040, which can also be configured to be visible in fluoroscopy. A radiopaque band, coating, marker, or otherwise can be used to provide visibility in fluoroscopy.

In some arrangements, the securing element 6310 can also be configured to be visible in fluoroscopy and therefore can be visualized by a user. Therefore, a user can use the openings 8072 to determine a position of the constricted tissue that surrounds the outer sheath 8040 relative to the securing element 6310 to determine if the securing element 6310 can be expanded and deployed. If the distal end portion 6316*b* of each of the struts 6316 of the securing element 6310 is distal to the constricted tissue that surrounds the outer sheath 8040 when the implant is axially positioned as shown in FIG. 16D (e.g., so that a distal end 8086*b* of the inner catheter 8086 is positioned adjacent or within a predetermined distance from a distal end 8040*b* of the outer sheath 8040), then the securing element 6310 is not in an optimal position for deployment by withdrawal of the outer sheath 8040. The user may release and reengage the LAA or otherwise adjust a position of the implant relative to the constricted tissue to ensure that at least the distal end portion 6316*b* of each of the struts 6316 of the securing element 6310 is distal to the constricted tissue that surrounds the outer sheath 8040 when the implant is axially positioned as shown in FIG. 16D.

In some arrangements, the openings 8072 may be a plurality of circumferentially extending slits that extend circumferentially around the distal section 8070. For example without limitation, each of the slits can have a length that is 10% or approximately 10% of a circumference of the distal section 8070, or from 10%, approximately 10%, or less than 10% to 50%, approximately 50%, or more than 50%, or from 15% or approximately 15% to 40% or approximately 40%, or from 15% or approximately 15% to 20% or approximately 20% of the circumference of the distal section 8070, or any value or range of values within any of the foregoing ranges. In some arrangements, the distal section 8070 can have a space 8073 between each of the openings 8072 in the circumferential direction. In some arrangements, the space 8073 between each of the openings 8072 can form a helical or angled pattern on the distal section 8070.

In any arrangements disclosed herein, any of the tubes, catheters, or sheaths (including, without limitation, the outer sheath 8040, the inner catheter 8086, and the second inner catheter 8098 described in greater detail below) can be made from metal, which can be stainless steel. In any arrangements, the tubes, catheters, or sheaths can be laser cut, which can improve flexibility of the tube, catheter, or sheath. Some arrangements of the outer sheath 8040 can include a laser cut, stainless steel tube and a polymer (e.g., Pebax) jacket over at least a portion thereof. For example and without limitation, for the outer sheath 8040, a polymer jacket can extend from a proximal end of the outer sheath 8040 to a proximal end of the distal section 8070 so as to not cover the openings 8072 in the distal section 8070. In some arrangements, the openings 8072 can extend along an entire length or substantially an entire length of the metal layer of the outer sheath 8040 and the polymer jacket can extend from a proximal end of the outer sheath 8040 to a proximal end of the distal section 8070 so as to not cover the openings 8072 in the distal section 8070. In some arrangements, a distal end portion of the jacket can be heat melted to the metal tube. For this purpose, so that the jacket does not flow through the openings 8072, a band or section without openings can be formed that can be aligned with the distal end of the jacket.

In any arrangements of the system 8000, a size, pattern, and angular orientation of the openings can vary along a length of the metal tube to provide variations in the flexibility of the tube, catheter, or sheath. For example, an angle of the spaces 8073 between the openings 8072 relative to a longitudinal centerline axis of the sheath can be greater at a distal end of the sheath to provide greater flexibility at the distal end thereof. A proximal end portion of the sheath can be designed to be stiffer, such as by angling the spaces between the openings at a lower angle relative to the longitudinal axis of the sheath, and a medium stiffness portion can extend between the proximal and distal portions.

In some arrangements, the delivery catheter 8010 can have one or more biasing elements (e.g., spring or springs) to bias some of the components of the delivery catheter 8010 to move relative to one another or to exert a force on one or more of the components of the delivery catheter 8010. For example and without limitation, in some arrangements, one or more springs can be used to pull the fourth dial 8102 and the inner core 8106 in a proximal direction relative to the second inner catheter 8098. This can bias the second inner catheter 8098 to remain in contact and engagement with the retention element 6308 and/or the screw head 6330 of the retention element 6308. Additionally, in some arrangements, one or more springs can be used to pull the fourth dial 8102, the inner core 8106 and/or the second inner catheter 8098 in a proximal direction relative to the inner catheter 8088. This can bias the inner catheter 8088 to remain in contact and engagement with the securing element 6310.

In some arrangements, one or more or all of the components of the implant device and/or delivery device can be provided in a sterile condition. For example and without limitation, one or more or all of the components of the implant device and/or delivery device can be provided in a sterile container or pouch, and can be double pouched. In some arrangements, some of the components of the delivery system can be provided non-sterile, and can be intended to be positioned and used on the non-sterile side of a sterile barrier in the operating room.

While certain arrangements of the inventions have been described, these arrangements have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, arrangement, or example are to be understood to be applicable to any other aspect, arrangement or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing arrangements. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some arrangements, the actual steps taken in the processes illustrated and/or disclosed may differ from those shown in the figures. Depending on the arrangement, certain of the steps described above may be removed, others may be added. Furthermore, the features and attributes of the specific arrangements disclosed above may be combined in different ways to form additional arrangements, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular arrangement. Thus, for example, those skilled in the art will recognize that the disclosure may be embodied or carried out in a manner that achieves one advantage or a group of advantages as taught herein without necessarily achieving other advantages as may be taught or suggested herein.

The foregoing description provides detailed embodiments of a left atrial appendage (LAA) device configured for LAA elimination using a twisting mechanism; however, the principles of the invention are not limited to this particular approach. The concepts described herein, including the integration of ablation functionality, electrode placement for unipolar and bipolar configurations, and hybrid localization techniques, can be equally applied to other types of intracardiac LAA occlusion devices. For example, LAA occlusion devices such as the Watchman™ (Boston Scientific), WaveCrest™ (Coherex, Inc.), and Amulet™ (Medtronic) may be adapted within the scope of the invention to incorporate the electrode configurations, energy delivery mechanisms, and multi-modal navigation techniques described herein. Any such modifications, whether applied to a twisting-based LAA elimination device or an occlusion-based implant, remain within the spirit and scope of the invention as set forth in the claims.

Conditional language, such as "can," "could," "might," or "may," unless specifically stated otherwise, or otherwise understood within the context as used, is generally intended to convey that certain arrangements include, while other arrangements do not include, certain features, elements, and/or steps. Thus, such conditional language is not generally intended to imply that features, elements, and/or steps are in any way required for one or more arrangements or that one or more arrangements necessarily include logic for deciding, with or without user input or prompting, whether these features, elements, and/or steps are included or are to be performed in any particular arrangement.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain arrangements require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain arrangements, the terms "generally parallel" and "substantially parallel" refer to a value, amount, or characteristic that departs from exactly parallel by less than or equal to 15°, 10°, 5°, 3°, 1 degree, or 0.1 degree. The ranges disclosed herein also encompass any and all overlap, sub-ranges, and combinations thereof, and any specific values within those ranges. Language such as "up to," "at least," "greater than," "less than," "between," and the like includes the number recited. Numbers and values used herein preceded by a term such as "about" or "approximately" include the recited numbers. For example, "approximately 7 mm" includes "7 mm" and numbers and ranges preceded by a term such as "about" or "approximately" should be interpreted as disclosing numbers and ranges with or without such a term in front of the number or value such that this application supports claiming the numbers, values and ranges disclosed in the specification and/or claims with or without the term such as "about" or "approximately" before such numbers, values or ranges such, for example, that "approximately two times to approximately five times" also includes the disclosure of the range of "two times to five times." The scope of the present disclosure is not intended to be limited by the specific disclosures of preferred arrangements in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A left atrial appendage ("LAA") treatment device, comprising:
    an expandable frame comprising one or more conductive elements configured to ablate cardiac tissue at a location in or proximate a heart, the location being distinct from an ostium of an LAA and an interior of the LAA,
    the expandable frame further configured for at least partial insertion into the LAA ostium to effect an occlusion or elimination of the LAA.

2. The LAA treatment device of claim 1, wherein the one or more conductive elements comprise one or more electrodes.

3. The LAA treatment device of claim 2, wherein a body of the expandable frame is configured to serve as an electrode.

4. The LAA treatment device of claim 2, wherein at least one of the one or more electrodes of the expandable frame serves as a first electrode in a pair of electrodes for performing bipolar ablation.

5. The LAA treatment device of claim 4, further comprising a securing element comprising one or more electrodes.

6. The LAA treatment device of claim 5, wherein at least one of the one or more electrodes of the securing element serves as a second electrode in the pair of electrodes for performing bipolar ablation.

7. The LAA treatment device of claim 1, wherein the cardiac tissue comprises tissue of a ventricle or an atrium.

8. An implantable cardiac ablation device, comprising:
    an expandable frame comprising one or more electrodes for ablating cardiac tissue of an atrium at a location distinct from a left atrial appendage ("LAA") ostium and an interior of the LAA,
    the one or more electrodes configured for implantation at least partially within the LAA.

9. The implantable cardiac ablation device of claim 8, wherein the one or more electrodes of the expandable frame are configured to perform RF ablation, PFA, or cryoablation.

10. The implantable cardiac ablation device of claim 8, wherein the one or more electrodes of the expandable frame are configured to perform unipolar ablation.

11. The implantable cardiac ablation device of claim 8, wherein the expandable frame comprises a material including one or more of nitinol, cobalt chromium, stainless steel, titanium, or combinations thereof.

12. The implantable cardiac ablation device of claim 8, wherein the one or more electrodes are coupled to the expandable frame.

13. The implantable cardiac ablation device of claim 12, wherein the one or more electrodes comprise one or more of stainless steel, cobalt chromium, gold, platinum, palladium, or alloys thereof.

14. The implantable cardiac ablation device of claim 8, the expandable frame comprising a plurality of struts, the one or more electrodes each coupled to a strut.

15. A method for performing cardiac ablation using an implant device, comprising:
    positioning an expandable frame comprising one or more electrodes at a first ablation site located outside a left atrial appendage ("LAA") of a heart;
    ablating cardiac tissue at the first ablation site by the one or more electrodes; and
    re-positioning the expandable frame at an implant site located at least partially within the LAA.

16. The method of claim 15, wherein the first ablation site is selected from one or more of: a pulmonary vein ostia, a left atrial posterior wall, a left atrial roof, a mitral isthmus, a coronary sinus, or a right atrium.

17. The method of claim 15, further including expanding the expandable frame before the ablating at the first ablation site.

18. The method of claim 17, wherein re-positioning the expandable frame comprises positioning a distal end of the expandable frame at least partially within the LAA.

19. The method of claim 18, further including expanding a securing member of the implant device, the securing member configured to cooperate with the expandable frame at the implant site.

20. The method of claim 15, further including ablating cardiac tissue using the one or more electrodes of the expandable frame at a second ablation site distinct from the first ablation site, the second ablation site located within the LAA or an ostium of the LAA.

* * * * *